United States Patent
Tsui et al.

(10) Patent No.: US 11,767,369 B2
(45) Date of Patent: Sep. 26, 2023

(54) MOLECULES WITH ALTERED NEONATE FC RECEPTOR BINDING HAVING ENHANCED THERAPEUTIC AND DIAGNOSTIC PROPERTIES

(71) Applicant: MEDIMMUNE, LLC, Gaithersburg, MD (US)

(72) Inventors: Ping Tsui, Gaithersburg, MD (US); Martin Borrok, Gaithersburg, MD (US); William Dall'Acqua, Gaithersburg, MD (US); Yanli Wu, Gaithersburg, MD (US); Nurten Beyaz-Kavuncu, Gaithersburg, MD (US)

(73) Assignee: MedImmune, LLC, Gaithersburg, MD (US)

( * ) Notice: Subject to any disclaimer, the term of this patent is extended or adjusted under 35 U.S.C. 154(b) by 665 days.

(21) Appl. No.: 16/566,280

(22) Filed: Sep. 10, 2019

(65) Prior Publication Data
US 2020/0071423 A1 Mar. 5, 2020

Related U.S. Application Data

(63) Continuation of application No. 15/310,196, filed as application No. PCT/US2015/030964 on May 15, 2015, now abandoned.

(60) Provisional application No. 61/994,379, filed on May 16, 2014.

(51) Int. Cl.
| | |
|---|---|
| C07K 16/00 | (2006.01) |
| C12P 21/08 | (2006.01) |
| C07K 16/40 | (2006.01) |
| C07K 16/10 | (2006.01) |
| C07K 16/28 | (2006.01) |
| A61K 47/68 | (2017.01) |
| A61K 39/00 | (2006.01) |

(52) U.S. Cl.
CPC .............. *C07K 16/40* (2013.01); *A61K 47/68* (2017.08); *C07K 16/00* (2013.01); *C07K 16/005* (2013.01); *C07K 16/1027* (2013.01); *C07K 16/2887* (2013.01); *A61K 2039/505* (2013.01); *C07K 2317/24* (2013.01); *C07K 2317/52* (2013.01); *C07K 2317/524* (2013.01); *C07K 2317/77* (2013.01); *C07K 2317/92* (2013.01); *C07K 2317/94* (2013.01); *C07K 2319/00* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 5,843,708 A | 12/1998 | Hardman et al. | |
| 7,658,921 B2* | 2/2010 | Dall'Acqua | C07K 16/00 |
| | | | 424/139.1 |
| 2006/0275282 A1 | 6/2006 | Moore et al. | |
| 2007/0148164 A1 | 6/2007 | Farrington et al. | |
| 2013/0131319 A1 | 5/2013 | Igawa et al. | |

FOREIGN PATENT DOCUMENTS

| | | |
|---|---|---|
| WO | WO02/060919 A2 | 8/2002 |
| WO | 2005047327 A2 | 5/2005 |
| WO | 2006020114 A2 | 2/2006 |
| WO | WO2006/053301 A2 | 5/2006 |
| WO | WO2009/058492 A2 | 5/2009 |
| WO | 2011122011 A2 | 10/2011 |
| WO | 2013093809 A1 | 6/2013 |

OTHER PUBLICATIONS

Yeung Yik Andy et al, "Engineering Human IgG1 Affinity to Human Neonatal Fc Receptor: Impact of Affinity Improvement on Pharmacokinetics in Primates". The Journal of Immunology, The American Association of Immunologists, US, vol. 182, No. 12, Jun. 1, 2009, pp. 7663-7671.
Carlos Vaccaro et al, "Engineering the Fc region of immunoglobulin G to modulate in vivo antibody levels", Nature Biotechnology, vol. 23, No. 10, Oct. 1, 2005, pp. 1283-1288.
W. F. D. Acqua et al, "Increasing the Affinity of a Human IgG1 for the Neonatal Fc Receptor: Biological Consequences", The Journal of Immunology, vol. 169, No. 9, Nov. 1, 2002.
R. Deng et al: "Pharmacokinetics of Humanized Monoclonal Anti-Tumor Necrosis Factor—Antibody and its Neonatal Fc Receptor Variants in Mice and Cynomolgus Monkeys", Drug Metabolism and Disposition, vol. 38, No. 4, Apr. 1, 2010.
Timothy T. Kuo et al, "Neonatal Fc receptor and IgG-based therapeutics", MABS, Sep. 1, 2011.
M. Jack Borrok et al: "Ph-dependent Binding Engineering Reveals an FcRn Affinity Threshold That Governs IgG Recycling", Journal of Biological Chemistry, vol. 290, No. 7, Dec. 23, 2014.

* cited by examiner

Primary Examiner — Chun W Dahle

(57) ABSTRACT

The present invention provides molecules, including proteins, more particularly, immunoglobulins whose in vivo half-lives are altered (increased or decreased) by the presence of an IgG constant domain, or FcRn binding fragment thereof (e.g., an Fc region or hinge-Fc region) (e.g., from a human IgG, e.g., human IgG1), that have modifications of one or more amino acid residues in at least the CH3 domain.

26 Claims, 16 Drawing Sheets
Specification includes a Sequence Listing.

Figure 1A

| EU | 118 | 119 | 120 | 121 | 122 | 123 | 124 | 125 | 126 | 127 | 128 | 129 | 130 | 131 | 132 | 133 | 134 | 135 | 136 | 137 |
|---|---|---|---|---|---|---|---|---|---|---|---|---|---|---|---|---|---|---|---|---|
| IgG1 | A | S | T | K | G | P | S | V | F | P | L | A | P | S | S | K | S | T | S | G |
| IgG2 | A | S | T | K | G | P | S | V | F | P | L | A | P | C | S | R | S | T | S | E |
| IgG3 | A | S | T | K | G | P | S | V | F | P | L | A | P | C | S | R | S | T | S | G |
| IgG4 | A | S | T | K | G | P | S | V | F | P | L | A | P | C | S | R | S | T | S | E |

| EU | 138 | 139 | 140 | 141 | 142 | 143 | 144 | 145 | 146 | 147 | 148 | 149 | 150 | 151 | 152 | 153 | 154 | 155 | 156 | 157 |
|---|---|---|---|---|---|---|---|---|---|---|---|---|---|---|---|---|---|---|---|---|
| IgG1 | G | T | A | A | L | G | C | L | V | K | D | Y | F | P | E | P | V | T | V | S |
| IgG2 | S | T | A | A | L | G | C | L | V | K | D | Y | F | P | E | P | V | T | V | S |
| IgG3 | G | T | A | A | L | G | C | L | V | K | D | Y | F | P | E | P | V | T | V | S |
| IgG4 | S | T | A | A | L | G | C | L | V | K | D | Y | F | P | E | P | V | T | V | S |

| EU | 158 | 159 | 160 | 161 | 162 | 163 | 164 | 165 | 166 | 167 | 168 | 169 | 170 | 171 | 172 | 173 | 174 | 175 | 176 | 177 |
|---|---|---|---|---|---|---|---|---|---|---|---|---|---|---|---|---|---|---|---|---|
| IgG1 | W | N | S | G | A | L | T | S | G | V | H | T | F | P | A | V | L | Q | S | S |
| IgG2 | W | N | S | G | A | L | T | S | G | V | H | T | F | P | A | V | L | Q | S | S |
| IgG3 | W | N | S | G | A | L | T | S | G | V | H | T | F | P | A | V | L | Q | S* | S |
| IgG4 | W | N | S | G | A | L | T | S | G | V | H | T | F | P | A | V | L | Q | S | S |

| EU | 178 | 179 | 180 | 181 | 182 | 183 | 184 | 185 | 186 | 187 | 188 | 189 | 190 | 191 | 192 | 193 | 194 | 195 | 196 | 197 |
|---|---|---|---|---|---|---|---|---|---|---|---|---|---|---|---|---|---|---|---|---|
| IgG1 | G | L | Y | S | L | S | S | V | V | T | V | P | S | S | S | L | G | T | Q | T |
| IgG2 | G | L | Y | S | L | S | S | V | V | T | V | P* | S | S | N* | F* | G | T | Q | T |
| IgG3 | G | L | Y | S | L | S | S | V | V | T | V | P | S | S | S* | L* | G | T | Q | T |
| IgG4 | G | L | Y | S | L | S | S | V | V | T | V | P | S | S | S | L | G | K | Q | T |

*site of known allelic variation

Figure 1B

| EU   | 198 | 199 | 200 | 201 | 202 | 203 | 204 | 205 | 206 | 207 | 208 | 209 | 210 | 211 | 212 | 213 | 214 | 215 | 216 | 217 |
|------|-----|-----|-----|-----|-----|-----|-----|-----|-----|-----|-----|-----|-----|-----|-----|-----|-----|-----|-----|-----|
| IgG1 | Y   | I   | C   | N   | V   | N   | H   | K   | P   | S   | N   | T   | K   | V   | D   | K   | K*  | V   | E   | P   |
| IgG2 | Y   | T   | C   | N   | V   | D   | H   | K   | P   | S   | N   | T   | K   | V   | D   | K   | T   | V   | E   | R   |
| IgG3 | Y   | T   | C   | N   | V   | N   | H   | K   | P   | S   | N   | T   | K   | V   | D   | K   | R   | V   | E   | L   |
| IgG4 | Y   | T   | C   | N   | V   | D   | H   | K   | P   | S   | N   | T   | K   | V   | D   | K   | R   | V   | E   | S   |

| EU   | 218 | 219 | 220 | 221 | 222 | 223 | 224 | 225 | 226 | 227 | 228 |
|------|-----|-----|-----|-----|-----|-----|-----|-----|-----|-----|-----|
| IgG1 | K   | S   | C   | D   | K   | T   | H   | T   | C   | P   | P   |
| IgG2 | K   |     | C   | C   | V   |     | E   |     | C   | P   | P   |
| IgG3 | K   | T   | P   | L   | T   | D   | H   | T   | C   | P   | R   |
| IgG4 | K   | Y   | G   |     |     |     | P   | P   | C   | P   | S   |

| EU   | | | | | | | | | | | | |
|------|---|---|---|---|---|---|---|---|---|---|---|---|
| IgG1 | | | | | | | | | | | | |
| IgG2 | | | | | | | | | | | | |
| IgG3 | D | T | P | P | P | C | P | R | C | P | E | P K S C D T P P P |
| IgG4 | | | | | | | | | | | | |

| EU   | 229 | 230 | | | |
|------|-----|-----|---|---|---|
| IgG1 | C   | P   | | | |
| IgG2 | C   | P   | | | |
| IgG3 | C P R C P | P | | | |
| IgG4 | C   | P   | | | |

*site of known allelic variation

Figure 1C

| EU  | 231 | 232 | 233 | 234 | 235 | 236 | 237 | 238 | 239 | 240 | 241 | 242 | 243 | 244 | 245 | 246 | 247 | 248 | 249 | 250 | 251 | 252 |
|-----|-----|-----|-----|-----|-----|-----|-----|-----|-----|-----|-----|-----|-----|-----|-----|-----|-----|-----|-----|-----|-----|-----|
| IgG1| A   | P   | E   | L   | L   | G   | G   | P   | S   | V   | F   | L   | F   | P   | P   | K   | P   | K   | D   | T   | L   | M   |
| IgG2| A   | P   | P   | V   | A   | G   | G   | P   | S   | V   | F   | L   | F   | P   | P   | K   | P   | K   | D   | T   | L   | M   |
| IgG3| A   | P   | E   | L   | L   | G   | G   | P   | S   | V   | F   | L   | F   | P   | P   | K   | P   | K   | D   | T   | L   | M   |
| IgG4| A   | P   | E   | F   | L   | G   | G   | P   | S   | V   | F   | L   | F   | P   | P   | K   | P   | K   | D   | T   | L   | M   |

| EU  | 253 | 254 | 255 | 256 | 257 | 258 | 259 | 260 | 261 | 262 | 263 | 264 | 265 | 266 | 267 | 268 | 269 | 270 | 271 | 272 | 273 | 274 |
|-----|-----|-----|-----|-----|-----|-----|-----|-----|-----|-----|-----|-----|-----|-----|-----|-----|-----|-----|-----|-----|-----|-----|
| IgG1| I   | S   | R   | T   | P   | E   | V   | T   | C   | V   | V   | V   | D   | V   | S   | H   | E   | D   | P   | E   | V   | K   |
| IgG2| I   | S   | R   | T   | P   | E   | V   | T   | C   | V   | V   | V   | D   | V   | S   | H   | E   | D   | P   | E   | V   | Q   |
| IgG3| I   | S   | R   | T   | P   | E   | V   | T   | C   | V   | V   | V   | D   | V   | S   | H   | E   | D   | P   | E   | V   | Q   |
| IgG4| I   | S   | R   | T   | P   | E   | V   | T   | C   | V   | V   | V   | D   | V   | S   | Q   | E   | D   | P   | E   | V   | Q   |

| EU  | 275 | 276 | 277 | 278 | 279 | 280 | 281 | 282 | 283 | 284 | 285 | 286 | 287 | 288 | 289 | 290 | 291 | 292 | 293 | 294 | 295 | 296 |
|-----|-----|-----|-----|-----|-----|-----|-----|-----|-----|-----|-----|-----|-----|-----|-----|-----|-----|-----|-----|-----|-----|-----|
| IgG1| F   | N   | W   | Y   | V   | D   | G   | V   | E   | V   | H   | N   | A   | K   | T   | K   | P   | R   | E   | E   | Q   | Y   |
| IgG2| F   | N   | W   | Y   | V   | D   | G   | V*  | E   | V   | H   | N   | A   | K   | T   | K   | P   | R   | E   | E   | Q   | F   |
| IgG3| F   | K   | W   | Y   | V   | D   | G   | V   | E   | V   | H   | N   | A   | K   | T   | K   | P*  | R*  | E   | E   | Q   | Y*  |
| IgG4| F   | N   | W   | Y   | V   | D   | G   | V   | E   | V   | H   | N   | A   | K   | T   | K   | P   | R   | E   | E   | Q   | F   |

| EU  | 297 | 298 | 299 | 300 | 301 | 302 | 303 | 304 | 305 | 306 | 307 | 308 | 309 | 310 | 311 | 312 | 313 | 314 | 315 | 316 | 317 | 318 |
|-----|-----|-----|-----|-----|-----|-----|-----|-----|-----|-----|-----|-----|-----|-----|-----|-----|-----|-----|-----|-----|-----|-----|
| IgG1| N   | S   | T   | Y   | R   | V   | V   | S   | V   | L   | T   | V   | L   | H   | Q   | D   | W   | L   | N   | G   | K   | E   |
| IgG2| N   | S   | T   | F   | R   | V   | V   | S   | V   | L   | T   | V   | V   | H   | Q   | D   | W   | L   | N   | G   | K   | E   |
| IgG3| N   | S   | T   | F   | R   | V   | V   | S   | V   | L   | T   | V   | L*  | H   | Q   | D   | W   | L   | N   | G   | K   | E   |
| IgG4| N   | S   | T   | Y   | R   | V   | V   | S   | V   | L   | T   | V   | L   | H   | Q   | D   | W   | L   | N   | G   | K   | E   |

| EU  | 319 | 320 | 321 | 322 | 323 | 324 | 325 | 326 | 327 | 328 | 329 | 330 | 331 | 332 | 333 | 334 | 335 | 336 | 337 | 338 | 339 | 340 |
|-----|-----|-----|-----|-----|-----|-----|-----|-----|-----|-----|-----|-----|-----|-----|-----|-----|-----|-----|-----|-----|-----|-----|
| IgG1| Y   | K   | C   | K   | V   | S   | N   | K   | A   | L   | P   | A   | P   | I   | E   | K   | T   | I   | S   | K   | A   | K   |
| IgG2| Y   | K   | C   | K   | V   | S   | N   | K   | G   | L   | P   | A   | P   | I   | E   | K   | T   | I   | S   | K   | T   | K   |
| IgG3| Y   | K   | C   | K   | V   | S   | N   | K   | A   | L   | P   | A   | P   | I   | E   | K   | T   | I   | S   | K   | T   | K   |
| IgG4| Y   | K   | C   | K   | V   | S   | N   | K   | G   | L   | P   | S   | S   | I   | E   | K   | T   | I   | S   | K   | A   | K   |

*site of known allelic variation

Figure 1D

| EU | 341 | 342 | 343 | 344 | 345 | 346 | 347 | 348 | 349 | 350 | 351 | 352 | 353 | 354 | 355 | 356 | 357 | 358 | 359 | 360 | 361 | 362 |
|---|---|---|---|---|---|---|---|---|---|---|---|---|---|---|---|---|---|---|---|---|---|---|
| IgG1 | G | Q | P | R | E | P | Q | V | Y | T | L | P | P | S | R | D* | E | L* | T | K | N | Q |
| IgG2 | G | Q | P | R | E | P | Q | V | Y | T | L | P | P | S | R | E | E | M | T | K | N | Q |
| IgG3 | G | Q | P | R | E | P | Q | V | Y | T | L | P | P | S | R | E* | E | M* | T | K | N | Q |
| IgG4 | G | Q | P | R | E | P | Q | V | Y | T | L | P | P | S | Q | E | E | M | T | K | N | Q |

| EU | 363 | 364 | 365 | 366 | 367 | 368 | 369 | 370 | 371 | 372 | 373 | 374 | 375 | 376 | 377 | 378 | 379 | 380 | 381 | 382 | 383 | 384 |
|---|---|---|---|---|---|---|---|---|---|---|---|---|---|---|---|---|---|---|---|---|---|---|
| IgG1 | V | S | L | T | C | L | V | K | G | F | Y | P | S | D | I | A | V | E | W | E | S | N |
| IgG2 | V | S | L | T | C | L | V | K | G | F | Y | P | S | D | I | S* | V | E | W | E | S | N |
| IgG3 | V | S | L | T | C | L | V | K | G | F | Y | P | S | D | I | A | V | E | W | E | S | S* |
| IgG4 | V | S | L | T | C | L | V | K | G | F | Y | P | S | D | I | A | V | E | W | E | S | N |

| EU | 385 | 386 | 387 | 388 | 389 | 390 | 391 | 392 | 393 | 394 | 395 | 396 | 397 | 398 | 399 | 400 | 401 | 402 | 403 | 404 | 405 | 406 |
|---|---|---|---|---|---|---|---|---|---|---|---|---|---|---|---|---|---|---|---|---|---|---|
| IgG1 | G | Q | P | E | N | N | Y | K | T | T | P | P | V | L | D | S | D | G | S | F | F | L |
| IgG2 | G | Q | P | E | N | N | Y | K | T | T | P | P | M* | L | D | S | D | G | S | F | F | L |
| IgG3 | G | Q | P | E | N | N | Y | N* | T | T | P | P | M* | L | D | S | D | G | S | F | F | L |
| IgG4 | G | Q | P | E | N | N | Y | K | T | T | P | P | V | L | D | S | D | G | S | F | F | L |

| EU | 407 | 408 | 409 | 410 | 411 | 412 | 413 | 414 | 415 | 416 | 417 | 418 | 419 | 420 | 421 | 422 | 423 | 424 | 425 | 426 | 427 | 428 |
|---|---|---|---|---|---|---|---|---|---|---|---|---|---|---|---|---|---|---|---|---|---|---|
| IgG1 | Y | S | K | L | T | V | D | K | S | R | W | Q | Q | G | N | V | F | S | C | S | V | M |
| IgG2 | Y | S | K | L | T | V | D | K | S | R | W | Q | Q | G | N | V | F | S | C | S | V | M |
| IgG3 | Y | S | K* | L | T | V | D | K | S | R | W | Q | Q* | G | N | I* | F | S | C | S | V | M |
| IgG4 | Y | S | R* | L | T | V | D | K | S | R | W | Q | E | G | N | V | F | S | C | S | V | M |

| EU | 429 | 430 | 431 | 432 | 433 | 434 | 435 | 436 | 437 | 438 | 439 | 440 | 441 | 442 | 443 | 444 | 445 | 446 | 447 |
|---|---|---|---|---|---|---|---|---|---|---|---|---|---|---|---|---|---|---|---|
| IgG1 | H | E | A | L | H | N | H | Y | T | Q | K | S | L | S | L | S | P | G | K |
| IgG2 | H | E | A | L | H | N | H | Y | T | Q | K | S | L | S | L | S | P | G | K |
| IgG3 | H | E | A | L | H | N | R | F | T | Q | K | S | L | S | L | S | P | G | K |
| IgG4 | H | E | A | L | H | N | H | Y | T | Q | K | S | L | S | L | S | L | G | K |

*site of known allelic variation

Figure 1E

```
Met Gly Val Pro Arg Pro Gln Pro Trp Ala Leu Gly Leu Leu Leu Phe
1               5               10                  15
Leu Leu Pro Gly Ser Leu Gly Ala Glu Ser His Leu Ser Leu Leu Tyr
            20              25                  30
His Leu Thr Ala Val Ser Ser Pro Ala Pro Gly Thr Pro Ala Phe Trp
        35              40              45
Val Ser Gly Trp Leu Gly Pro Gln Gln Tyr Leu Ser Tyr Asn Ser Leu
    50              55              60
Arg Gly Glu Ala Glu Pro Cys Gly Ala Trp Val Trp Glu Asn Gln Val
65              70              75                      80
Ser Trp Tyr Trp Glu Lys Glu Thr Thr Asp Leu Arg Ile Lys Glu Lys
                85              90                  95
Leu Phe Leu Glu Ala Phe Lys Ala Leu Gly Gly Lys Gly Pro Tyr Thr
                100             105             110
Leu Gln Gly Leu Leu Gly Cys Glu Leu Gly Pro Asp Asn Thr Ser Val
            115             120             125
Pro Thr Ala Lys Phe Ala Leu Asn Gly Glu Glu Phe Met Asn Phe Asp
130             135             140
Leu Lys Gln Gly Thr Trp Gly Gly Asp Trp Pro Glu Ala Leu Ala Ile
145             150             155                     160
Ser Gln Arg Trp Gln Gln Gln Asp Lys Ala Ala Asn Lys Glu Leu Thr
                165             170                 175
Phe Leu Leu Phe Ser Cys Pro His Arg Leu Arg Glu His Leu Glu Arg
            180             185             190
Gly Arg Gly Asn Leu Glu Trp Lys Glu Pro Pro Ser Met Arg Leu Lys
            195             200             205
Ala Arg Pro Ser Ser Pro Gly Phe Ser Val Leu Thr Cys Ser Ala Phe
    210             215             220
Ser Phe Tyr Pro Pro Glu Leu Gln Leu Arg Phe Leu Arg Asn Gly Leu
225             230             235                     240
Ala Ala Gly Thr Gly Gln Gly Asp Phe Gly Pro Asn Ser Asp Gly Ser
            245             250             255
Phe His Ala Ser Ser Ser Leu Thr Val Lys Ser Gly Asp Glu His His
                260             265             270
Tyr Cys Cys Ile Val Gln His Ala Gly Leu Ala Gln Pro Leu Arg Val
        275             280             285
Glu Leu Glu Ser Pro Ala Lys Ser Ser Val Leu Val Val Gly Ile Val
    290             295             300
Ile Gly Val Leu Leu Leu Thr Ala Ala Ala Val Gly Gly Ala Leu Leu
305             310             315                     320
Trp Arg Arg Met Arg Ser Gly Leu Pro Ala Pro Trp Ile Ser Leu Arg
                325             330             335
Gly Asp Asp Thr Gly Val Leu Leu Pro Thr Pro Gly Glu Ala Gln Asp
            340             345             350
Ala Asp Leu Lys Asp Val Asn Val Ile Pro Ala Thr Ala
            355             360             365
```

Human neonatal Fc receptor (FcRn); SEQ ID NO:5

Figure 1F

```
Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
            20                  25                  30

His Pro Ala Glu Asn Gly Lys Ser Asn Phe Leu Asn Cys Tyr Val Ser
            35                  40                  45

Gly Phe His Pro Ser Asp Ile Glu Val Asp Leu Leu Lys Asn Gly Glu
        50                  55                  60

Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
            100                 105                 110

Val Lys Trp Asp Arg Asp Met
            115
``` beta-2-microglobulin (p14 subunit of FcRn complex): SEQ ID NO:6

Figure 7A

Mean test protein-induced Stimulation Index (SI) over the test population

| Product | Mean SI | P-value* |
|---|---|---|
| Buffer | 1.00 | 0.6908 |
| KLH | 4.20 | <0.0001 |
| MOTA WT | 0.98 | 0.0940 |
| MOTA N3 | 0.91 | <0.0001 |

* The p-value related to the single sample t-test hypothesis that the frequency distribution of SI for a given antigen represents a distribution with a mean SI value of 1

Figure 7B

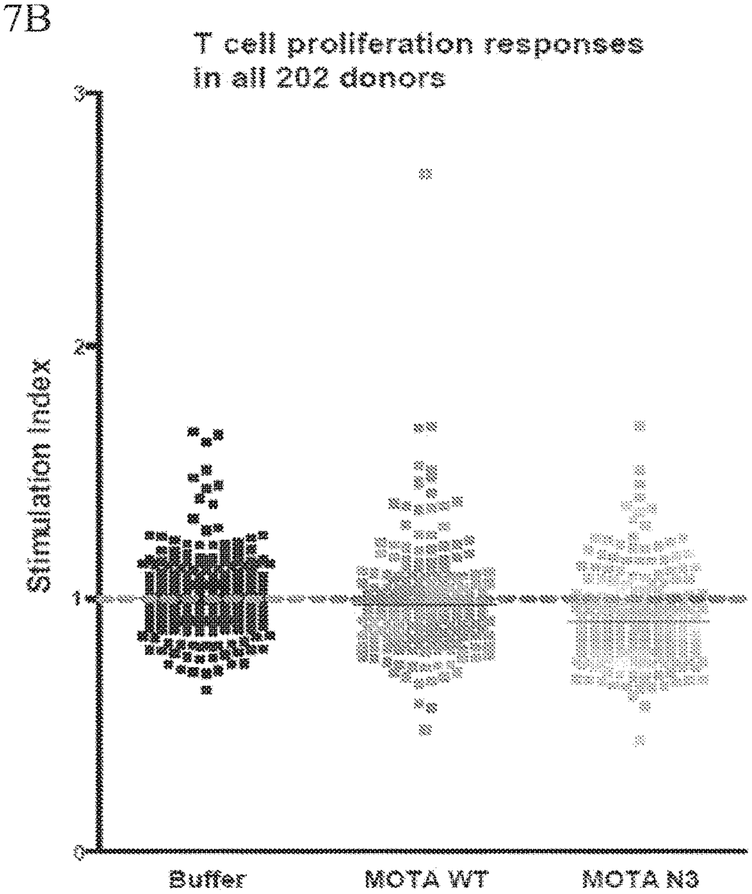

Classic antigen clearance with antibody with pH-dependent antigen binding

Antigen clearance with antibody with pH-dependent antigen binding and high affinity to FcRn at both pH 6.0 and 7.4

```
                           SEQUENCE LISTING

<160> NUMBER OF SEQ ID NOS: 59

<210> SEQ ID NO 1
<211> LENGTH: 110
<212> TYPE: PRT
<213> ORGANISM: Homo sapiens

<400> SEQUENCE: 1

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 2
<211> LENGTH: 107
<212> TYPE: PRT
<213> ORGANISM: Homo sapiens

<400> SEQUENCE: 2

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 3
<211> LENGTH: 15
<212> TYPE: PRT
<213> ORGANISM: Homo sapiens

<400> SEQUENCE: 3

Glu Pro Lys Ser Cys Asp Lys Thr His Thr Cys Pro Pro Cys Pro
1               5                   10                  15

<210> SEQ ID NO 4
```

```
<211> LENGTH: 232
<212> TYPE: PRT
<213> ORGANISM: Homo sapiens

<400> SEQUENCE: 4

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Lys
225                 230

<210> SEQ ID NO 5
<211> LENGTH: 365
<212> TYPE: PRT
<213> ORGANISM: Homo sapiens

<400> SEQUENCE: 5

Met Gly Val Pro Arg Pro Gln Pro Trp Ala Leu Gly Leu Leu Leu Phe
1               5                   10                  15

Leu Leu Pro Gly Ser Leu Gly Ala Glu Ser His Leu Ser Leu Leu Tyr
            20                  25                  30

His Leu Thr Ala Val Ser Ser Pro Ala Pro Gly Thr Pro Ala Phe Trp
        35                  40                  45

Val Ser Gly Trp Leu Gly Pro Gln Gln Tyr Leu Ser Tyr Asn Ser Leu
50                  55                  60

Arg Gly Glu Ala Glu Pro Cys Gly Ala Trp Val Trp Glu Asn Gln Val
65                  70                  75                  80

Ser Trp Tyr Trp Glu Lys Glu Thr Thr Asp Leu Arg Ile Lys Glu Lys
                85                  90                  95

Leu Phe Leu Glu Ala Phe Lys Ala Leu Gly Gly Lys Gly Pro Tyr Thr
            100                 105                 110
```

Leu Gln Gly Leu Leu Gly Cys Glu Leu Gly Pro Asp Asn Thr Ser Val
            115                 120                 125

Pro Thr Ala Lys Phe Ala Leu Asn Gly Glu Glu Phe Met Asn Phe Asp
    130                 135                 140

Leu Lys Gln Gly Thr Trp Gly Gly Asp Trp Pro Glu Ala Leu Ala Ile
145                 150                 155                 160

Ser Gln Arg Trp Gln Gln Asp Lys Ala Ala Asn Lys Glu Leu Thr
                165                 170                 175

Phe Leu Leu Phe Ser Cys Pro His Arg Leu Arg Glu His Leu Glu Arg
            180                 185                 190

Gly Arg Gly Asn Leu Glu Trp Lys Glu Pro Pro Ser Met Arg Leu Lys
            195                 200                 205

Ala Arg Pro Ser Ser Pro Gly Phe Ser Val Leu Thr Cys Ser Ala Phe
            210                 215                 220

Ser Phe Tyr Pro Pro Glu Leu Gln Leu Arg Phe Leu Arg Asn Gly Leu
225                 230                 235                 240

Ala Ala Gly Thr Gly Gln Gly Asp Phe Gly Pro Asn Ser Asp Gly Ser
                245                 250                 255

Phe His Ala Ser Ser Ser Leu Thr Val Lys Ser Gly Asp Glu His His
            260                 265                 270

Tyr Cys Cys Ile Val Gln His Ala Gly Leu Ala Gln Pro Leu Arg Val
            275                 280                 285

Glu Leu Glu Ser Pro Ala Lys Ser Ser Val Leu Val Val Gly Ile Val
            290                 295                 300

Ile Gly Val Leu Leu Leu Thr Ala Ala Ala Val Gly Gly Ala Leu Leu
305                 310                 315                 320

Trp Arg Arg Met Arg Ser Gly Leu Pro Ala Pro Trp Ile Ser Leu Arg
                325                 330                 335

Gly Asp Asp Thr Gly Val Leu Leu Pro Thr Pro Gly Glu Ala Gln Asp
            340                 345                 350

Ala Asp Leu Lys Asp Val Asn Val Ile Pro Ala Thr Ala
            355                 360                 365

<210> SEQ ID NO 6
<211> LENGTH: 119
<212> TYPE: PRT
<213> ORGANISM: Homo sapiens

<400> SEQUENCE: 6

Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
            20                  25                  30

His Pro Ala Glu Asn Gly Lys Ser Asn Phe Leu Asn Cys Tyr Val Ser
            35                  40                  45

Gly Phe His Pro Ser Asp Ile Glu Val Asp Leu Leu Lys Asn Gly Glu
        50                  55                  60

Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
            100                 105                 110

Val Lys Trp Asp Arg Asp Met

```
                    115

<210> SEQ ID NO 7
<211> LENGTH: 6
<212> TYPE: PRT
<213> ORGANISM: Homo sapiens
<220> FEATURE:
<221> NAME/KEY: MISC_FEATURE
<222> LOCATION: (1)..(6)
<223> OTHER INFORMATION: His 435 loop region of human IgG3
<220> FEATURE:
<221> NAME/KEY: VARIANT
<222> LOCATION: (4)..(4)
<223> OTHER INFORMATION: site of known allelic variation
<220> FEATURE:
<221> NAME/KEY: VARIANT
<222> LOCATION: (5)..(5)
<223> OTHER INFORMATION: site of known allelic variation

<400> SEQUENCE: 7

Leu His Asn Arg Phe Thr
1               5

<210> SEQ ID NO 8
<211> LENGTH: 6
<212> TYPE: PRT
<213> ORGANISM: Homo sapiens
<220> FEATURE:
<221> NAME/KEY: MISC_FEATURE
<222> LOCATION: (1)..(6)
<223> OTHER INFORMATION: His 435 loop region of human IgG1, IgG2, and
      IgG4

<400> SEQUENCE: 8

Leu His Asn His Tyr Thr
1               5

<210> SEQ ID NO 9
<211> LENGTH: 6
<212> TYPE: PRT
<213> ORGANISM: artificial
<220> FEATURE:
<223> OTHER INFORMATION: modified His435 loop region
<220> FEATURE:
<221> NAME/KEY: MISC_FEATURE
<222> LOCATION: (2)..(2)
<223> OTHER INFORMATION: X can be any amino acid
<220> FEATURE:
<221> NAME/KEY: MISC_FEATURE
<222> LOCATION: (3)..(3)
<223> OTHER INFORMATION: X can be any amino acid
<220> FEATURE:
<221> NAME/KEY: MISC_FEATURE
<222> LOCATION: (4)..(4)
<223> OTHER INFORMATION: X can be any amino acid
<220> FEATURE:
<221> NAME/KEY: MISC_FEATURE
<222> LOCATION: (5)..(5)
<223> OTHER INFORMATION: X can be any amino acid

<400> SEQUENCE: 9

Cys Xaa Xaa Xaa Xaa Cys
1               5

<210> SEQ ID NO 10
<211> LENGTH: 7
<212> TYPE: PRT
<213> ORGANISM: artificial
<220> FEATURE:
<223> OTHER INFORMATION: modified His435 loop region
<220> FEATURE:
<221> NAME/KEY: MISC_FEATURE
```

```
<222> LOCATION: (2)..(2)
<223> OTHER INFORMATION: X can be any amino acid
<220> FEATURE:
<221> NAME/KEY: MISC_FEATURE
<222> LOCATION: (3)..(3)
<223> OTHER INFORMATION: X can be any amino acid
<220> FEATURE:
<221> NAME/KEY: MISC_FEATURE
<222> LOCATION: (4)..(4)
<223> OTHER INFORMATION: X can be any amino acid
<220> FEATURE:
<221> NAME/KEY: MISC_FEATURE
<222> LOCATION: (5)..(5)
<223> OTHER INFORMATION: X can be any amino acid

<400> SEQUENCE: 10

Cys Xaa Xaa Xaa Xaa Cys Glu
1               5

<210> SEQ ID NO 11
<211> LENGTH: 6
<212> TYPE: PRT
<213> ORGANISM: artificial
<220> FEATURE:
<223> OTHER INFORMATION: modified His435 loop region
<220> FEATURE:
<221> NAME/KEY: MISC_FEATURE
<222> LOCATION: (2)..(2)
<223> OTHER INFORMATION: X can be any amino acid
<220> FEATURE:
<221> NAME/KEY: MISC_FEATURE
<222> LOCATION: (5)..(5)
<223> OTHER INFORMATION: X can be any amino acid
<220> FEATURE:
<221> NAME/KEY: MISC_FEATURE
<222> LOCATION: (6)..(6)
<223> OTHER INFORMATION: modified His 435 loop region may also include a
      glutamate insertion at position 437* as numbered by Kabat

<400> SEQUENCE: 11

Cys Xaa Arg His Xaa Cys
1               5

<210> SEQ ID NO 12
<211> LENGTH: 6
<212> TYPE: PRT
<213> ORGANISM: artificial
<220> FEATURE:
<223> OTHER INFORMATION: modified His435 loop region
<220> FEATURE:
<221> NAME/KEY: MISC_FEATURE
<222> LOCATION: (5)..(5)
<223> OTHER INFORMATION: X can be any amino acid
<220> FEATURE:
<221> NAME/KEY: MISC_FEATURE
<222> LOCATION: (6)..(6)
<223> OTHER INFORMATION: modified His 435 loop region may also include a
      glutamate insertion at position 437* as numbered by Kabat

<400> SEQUENCE: 12

Cys Arg Arg His Xaa Cys
1               5

<210> SEQ ID NO 13
<211> LENGTH: 6
<212> TYPE: PRT
<213> ORGANISM: artificial
<220> FEATURE:
<223> OTHER INFORMATION: modified His435 loop region
<220> FEATURE:
<221> NAME/KEY: MISC_FEATURE
<222> LOCATION: (2)..(2)
<223> OTHER INFORMATION: X can be any amino acid
```

```
<220> FEATURE:
<221> NAME/KEY: MISC_FEATURE
<222> LOCATION: (6)..(6)
<223> OTHER INFORMATION: modified His 435 loop region may also include a
      glutamate insertion at position 437* as numbered by Kabat

<400> SEQUENCE: 13

Cys Xaa Arg His Arg Cys
1               5

<210> SEQ ID NO 14
<211> LENGTH: 6
<212> TYPE: PRT
<213> ORGANISM: artificial
<220> FEATURE:
<223> OTHER INFORMATION: modified His435 loop region
<220> FEATURE:
<221> NAME/KEY: MISC_FEATURE
<222> LOCATION: (1)..(1)
<223> OTHER INFORMATION: X is glutamate, glutamine, aspartate, or
      histidine
<220> FEATURE:
<221> NAME/KEY: MISC_FEATURE
<222> LOCATION: (2)..(2)
<223> OTHER INFORMATION: X can be any amino acid
<220> FEATURE:
<221> NAME/KEY: MISC_FEATURE
<222> LOCATION: (3)..(3)
<223> OTHER INFORMATION: X can be any amino acid
<220> FEATURE:
<221> NAME/KEY: MISC_FEATURE
<222> LOCATION: (5)..(5)
<223> OTHER INFORMATION: X can be any amino acid
<220> FEATURE:
<221> NAME/KEY: MISC_FEATURE
<222> LOCATION: (6)..(6)
<223> OTHER INFORMATION: X is glutamate, glutamine, aspartate, or
      histidine

<400> SEQUENCE: 14

Xaa Xaa Xaa His Xaa Xaa
1               5

<210> SEQ ID NO 15
<211> LENGTH: 6
<212> TYPE: PRT
<213> ORGANISM: artificial
<220> FEATURE:
<223> OTHER INFORMATION: His435 loop region consensus sequence
<220> FEATURE:
<221> NAME/KEY: MISC_FEATURE
<222> LOCATION: (2)..(2)
<223> OTHER INFORMATION: X is arginine or alanine
<220> FEATURE:
<221> NAME/KEY: MISC_FEATURE
<222> LOCATION: (3)..(3)
<223> OTHER INFORMATION: X is tryptophan, serine, phenylalanine, or
      tyrosine

<400> SEQUENCE: 15

Glu Xaa Xaa His Arg Gln
1               5

<210> SEQ ID NO 16
<211> LENGTH: 7
<212> TYPE: PRT
<213> ORGANISM: artificial
<220> FEATURE:
<223> OTHER INFORMATION: modified His435 loop region

<400> SEQUENCE: 16

Cys Ser Trp His Leu Cys Glu
```

```
1               5

<210> SEQ ID NO 17
<211> LENGTH: 6
<212> TYPE: PRT
<213> ORGANISM: artificial
<220> FEATURE:
<223> OTHER INFORMATION: modified His435 loop region
<220> FEATURE:
<221> NAME/KEY: MISC_FEATURE
<222> LOCATION: (6)..(6)
<223> OTHER INFORMATION: modified His 435 loop region may also include a
      glutamate insertion at position 437* as numbered by Kabat

<400> SEQUENCE: 17

Cys Ser Phe His Leu Cys
1               5

<210> SEQ ID NO 18
<211> LENGTH: 6
<212> TYPE: PRT
<213> ORGANISM: artificial
<220> FEATURE:
<223> OTHER INFORMATION: modified His435 loop region
<220> FEATURE:
<221> NAME/KEY: MISC_FEATURE
<222> LOCATION: (6)..(6)
<223> OTHER INFORMATION: modified His 435 loop region may also include a
      glutamate insertion at position 437* as numbered by Kabat

<400> SEQUENCE: 18

Cys Ser Ile His Leu Cys
1               5

<210> SEQ ID NO 19
<211> LENGTH: 6
<212> TYPE: PRT
<213> ORGANISM: artificial
<220> FEATURE:
<223> OTHER INFORMATION: modified His435 loop region
<220> FEATURE:
<221> NAME/KEY: MISC_FEATURE
<222> LOCATION: (6)..(6)
<223> OTHER INFORMATION: modified His 435 loop region may also include a
      glutamate insertion at position 437* as numbered by Kabat

<400> SEQUENCE: 19

Cys Ser Leu His Leu Cys
1               5

<210> SEQ ID NO 20
<211> LENGTH: 6
<212> TYPE: PRT
<213> ORGANISM: artificial
<220> FEATURE:
<223> OTHER INFORMATION: modified His435 loop region

<400> SEQUENCE: 20

Cys Ser Trp His Leu Cys
1               5

<210> SEQ ID NO 21
<211> LENGTH: 6
<212> TYPE: PRT
<213> ORGANISM: artificial
<220> FEATURE:
<223> OTHER INFORMATION: modified His435 loop region
<220> FEATURE:
<221> NAME/KEY: MISC_FEATURE
<222> LOCATION: (2)..(2)
```

-continued

```
<223> OTHER INFORMATION: X can be any amino acid
<220> FEATURE:
<221> NAME/KEY: MISC_FEATURE
<222> LOCATION: (3)..(3)
<223> OTHER INFORMATION: X can be any amino acid
<220> FEATURE:
<221> NAME/KEY: MISC_FEATURE
<222> LOCATION: (5)..(5)
<223> OTHER INFORMATION: X can be any amino acid

<400> SEQUENCE: 21

Cys Xaa Xaa His Xaa Cys
1               5

<210> SEQ ID NO 22
<211> LENGTH: 7
<212> TYPE: PRT
<213> ORGANISM: artificial
<220> FEATURE:
<223> OTHER INFORMATION: modified His435 loop region
<220> FEATURE:
<221> NAME/KEY: MISC_FEATURE
<222> LOCATION: (2)..(2)
<223> OTHER INFORMATION: X can be any amino acid
<220> FEATURE:
<221> NAME/KEY: MISC_FEATURE
<222> LOCATION: (3)..(3)
<223> OTHER INFORMATION: X can be any amino acid
<220> FEATURE:
<221> NAME/KEY: MISC_FEATURE
<222> LOCATION: (5)..(5)
<223> OTHER INFORMATION: X can be any amino acid

<400> SEQUENCE: 22

Cys Xaa Xaa His Xaa Cys Glu
1               5

<210> SEQ ID NO 23
<211> LENGTH: 6
<212> TYPE: PRT
<213> ORGANISM: artificial
<220> FEATURE:
<223> OTHER INFORMATION: modified His435 loop region
<220> FEATURE:
<221> NAME/KEY: MISC_FEATURE
<222> LOCATION: (1)..(1)
<223> OTHER INFORMATION: X can be any amino acid
<220> FEATURE:
<221> NAME/KEY: MISC_FEATURE
<222> LOCATION: (2)..(2)
<223> OTHER INFORMATION: X can be any amino acid
<220> FEATURE:
<221> NAME/KEY: MISC_FEATURE
<222> LOCATION: (3)..(3)
<223> OTHER INFORMATION: X can be any amino acid
<220> FEATURE:
<221> NAME/KEY: MISC_FEATURE
<222> LOCATION: (5)..(5)
<223> OTHER INFORMATION: X can be any amino acid
<220> FEATURE:
<221> NAME/KEY: MISC_FEATURE
<222> LOCATION: (6)..(6)
<223> OTHER INFORMATION: X can be any amino acid

<400> SEQUENCE: 23

Xaa Xaa Xaa His Xaa Xaa
1               5

<210> SEQ ID NO 24
<211> LENGTH: 6
<212> TYPE: PRT
<213> ORGANISM: artificial
<220> FEATURE:
```

```
<223> OTHER INFORMATION: modified His435 loop region
<220> FEATURE:
<221> NAME/KEY: MISC_FEATURE
<222> LOCATION: (2)..(2)
<223> OTHER INFORMATION: X can be any amino acid
<220> FEATURE:
<221> NAME/KEY: MISC_FEATURE
<222> LOCATION: (6)..(6)
<223> OTHER INFORMATION: X can be any amino acid

<400> SEQUENCE: 24

Cys Xaa Arg His Arg Xaa
1               5

<210> SEQ ID NO 25
<211> LENGTH: 6
<212> TYPE: PRT
<213> ORGANISM: artificial
<220> FEATURE:
<223> OTHER INFORMATION: modified His435 loop region

<400> SEQUENCE: 25

Glu Arg Phe His Arg Gln
1               5

<210> SEQ ID NO 26
<211> LENGTH: 6
<212> TYPE: PRT
<213> ORGANISM: artificial
<220> FEATURE:
<223> OTHER INFORMATION: modified His435 loop region

<400> SEQUENCE: 26

Glu Arg Tyr His Thr Gln
1               5

<210> SEQ ID NO 27
<211> LENGTH: 6
<212> TYPE: PRT
<213> ORGANISM: artificial
<220> FEATURE:
<223> OTHER INFORMATION: modified His435 loop region

<400> SEQUENCE: 27

Glu Ala Trp His Arg Gln
1               5

<210> SEQ ID NO 28
<211> LENGTH: 6
<212> TYPE: PRT
<213> ORGANISM: artificial
<220> FEATURE:
<223> OTHER INFORMATION: modified His435 loop region

<400> SEQUENCE: 28

His Arg Phe His Leu Gln
1               5

<210> SEQ ID NO 29
<211> LENGTH: 6
<212> TYPE: PRT
<213> ORGANISM: artificial
<220> FEATURE:
<223> OTHER INFORMATION: modified His435 loop region

<400> SEQUENCE: 29

Glu Ala Phe His Arg Glu
1               5
```

```
<210> SEQ ID NO 30
<211> LENGTH: 6
<212> TYPE: PRT
<213> ORGANISM: artificial
<220> FEATURE:
<223> OTHER INFORMATION: modified His435 loop region

<400> SEQUENCE: 30

Ser Ser Trp His Leu Ser
1               5

<210> SEQ ID NO 31
<211> LENGTH: 6
<212> TYPE: PRT
<213> ORGANISM: artificial
<220> FEATURE:
<223> OTHER INFORMATION: modified His435 loop region

<400> SEQUENCE: 31

Cys His Asn His Tyr Cys
1               5

<210> SEQ ID NO 32
<211> LENGTH: 7
<212> TYPE: PRT
<213> ORGANISM: artificial
<220> FEATURE:
<223> OTHER INFORMATION: modified His435 loop region

<400> SEQUENCE: 32

Cys Arg Arg His Leu Cys Glu
1               5

<210> SEQ ID NO 33
<211> LENGTH: 7
<212> TYPE: PRT
<213> ORGANISM: artificial
<220> FEATURE:
<223> OTHER INFORMATION: modified His435 loop region

<400> SEQUENCE: 33

Cys Arg Arg His Ile Cys Glu
1               5

<210> SEQ ID NO 34
<211> LENGTH: 7
<212> TYPE: PRT
<213> ORGANISM: artificial
<220> FEATURE:
<223> OTHER INFORMATION: modified His435 loop region

<400> SEQUENCE: 34

Cys Ser Arg His Arg Cys Glu
1               5

<210> SEQ ID NO 35
<211> LENGTH: 7
<212> TYPE: PRT
<213> ORGANISM: artificial
<220> FEATURE:
<223> OTHER INFORMATION: modified His435 loop region

<400> SEQUENCE: 35

Cys Arg Arg His Ser Cys Glu
1               5
```

```
<210> SEQ ID NO 36
<211> LENGTH: 7
<212> TYPE: PRT
<213> ORGANISM: artificial
<220> FEATURE:
<223> OTHER INFORMATION: modified His435 loop region

<400> SEQUENCE: 36

Cys Asn Arg His Arg Cys Glu
1               5

<210> SEQ ID NO 37
<211> LENGTH: 6
<212> TYPE: PRT
<213> ORGANISM: artificial
<220> FEATURE:
<223> OTHER INFORMATION: modified His435 loop region

<400> SEQUENCE: 37

Glu Pro Tyr His Arg Glu
1               5

<210> SEQ ID NO 38
<211> LENGTH: 6
<212> TYPE: PRT
<213> ORGANISM: artificial
<220> FEATURE:
<223> OTHER INFORMATION: modified His435 loop region

<400> SEQUENCE: 38

Glu Arg Ser His Arg Gln
1               5

<210> SEQ ID NO 39
<211> LENGTH: 6
<212> TYPE: PRT
<213> ORGANISM: artificial
<220> FEATURE:
<223> OTHER INFORMATION: modified His435 loop region

<400> SEQUENCE: 39

Glu Pro His His Arg Gln
1               5

<210> SEQ ID NO 40
<211> LENGTH: 6
<212> TYPE: PRT
<213> ORGANISM: artificial
<220> FEATURE:
<223> OTHER INFORMATION: modified His435 loop region

<400> SEQUENCE: 40

His Thr His His Arg Gln
1               5

<210> SEQ ID NO 41
<211> LENGTH: 6
<212> TYPE: PRT
<213> ORGANISM: artificial
<220> FEATURE:
<223> OTHER INFORMATION: modified His435 loop region

<400> SEQUENCE: 41

Glu Pro Trp His Tyr Gln
1               5
```

-continued

```
<210> SEQ ID NO 42
<211> LENGTH: 6
<212> TYPE: PRT
<213> ORGANISM: artificial
<220> FEATURE:
<223> OTHER INFORMATION: modified His435 loop region

<400> SEQUENCE: 42

Glu Gln Phe His Arg Gln
1               5

<210> SEQ ID NO 43
<211> LENGTH: 6
<212> TYPE: PRT
<213> ORGANISM: artificial
<220> FEATURE:
<223> OTHER INFORMATION: modified His435 loop region

<400> SEQUENCE: 43

His His Phe His Met Gln
1               5

<210> SEQ ID NO 44
<211> LENGTH: 6
<212> TYPE: PRT
<213> ORGANISM: artificial
<220> FEATURE:
<223> OTHER INFORMATION: modified His435 loop region

<400> SEQUENCE: 44

Gln Lys Tyr His Asn Gln
1               5

<210> SEQ ID NO 45
<211> LENGTH: 6
<212> TYPE: PRT
<213> ORGANISM: artificial
<220> FEATURE:
<223> OTHER INFORMATION: modified His435 loop region

<400> SEQUENCE: 45

His Arg His His Arg Gln
1               5

<210> SEQ ID NO 46
<211> LENGTH: 6
<212> TYPE: PRT
<213> ORGANISM: artificial
<220> FEATURE:
<223> OTHER INFORMATION: modified His435 loop region

<400> SEQUENCE: 46

Glu Leu Trp His Arg Gln
1               5

<210> SEQ ID NO 47
<211> LENGTH: 6
<212> TYPE: PRT
<213> ORGANISM: artificial
<220> FEATURE:
<223> OTHER INFORMATION: modified His435 loop region

<400> SEQUENCE: 47

Glu Arg His His Arg Gln
1               5

<210> SEQ ID NO 48
```

```
<211> LENGTH: 6
<212> TYPE: PRT
<213> ORGANISM: artificial
<220> FEATURE:
<223> OTHER INFORMATION: modified His435 loop region

<400> SEQUENCE: 48

Glu Pro Trp His Arg Glu
1               5

<210> SEQ ID NO 49
<211> LENGTH: 6
<212> TYPE: PRT
<213> ORGANISM: artificial
<220> FEATURE:
<223> OTHER INFORMATION: modified His435 loop region

<400> SEQUENCE: 49

His Arg Phe His His Gln
1               5

<210> SEQ ID NO 50
<211> LENGTH: 6
<212> TYPE: PRT
<213> ORGANISM: artificial
<220> FEATURE:
<223> OTHER INFORMATION: modified His435 loop region

<400> SEQUENCE: 50

Glu Ala Tyr His His Gln
1               5

<210> SEQ ID NO 51
<211> LENGTH: 6
<212> TYPE: PRT
<213> ORGANISM: artificial
<220> FEATURE:
<223> OTHER INFORMATION: modified His435 loop region

<400> SEQUENCE: 51

Glu Gln Tyr His His Gln
1               5

<210> SEQ ID NO 52
<211> LENGTH: 6
<212> TYPE: PRT
<213> ORGANISM: artificial
<220> FEATURE:
<223> OTHER INFORMATION: modified His435 loop region

<400> SEQUENCE: 52

Glu Pro His His Asn Gln
1               5

<210> SEQ ID NO 53
<211> LENGTH: 6
<212> TYPE: PRT
<213> ORGANISM: artificial
<220> FEATURE:
<223> OTHER INFORMATION: modified His435 loop region

<400> SEQUENCE: 53

Glu Arg Tyr His His His
1               5

<210> SEQ ID NO 54
<211> LENGTH: 6
```

```
<212> TYPE: PRT
<213> ORGANISM: artificial
<220> FEATURE:
<223> OTHER INFORMATION: modified His435 loop region

<400> SEQUENCE: 54

Glu Arg Tyr His Asn Gln
1               5

<210> SEQ ID NO 55
<211> LENGTH: 6
<212> TYPE: PRT
<213> ORGANISM: artificial
<220> FEATURE:
<223> OTHER INFORMATION: modified His435 loop region

<400> SEQUENCE: 55

Glu Thr Phe His Gly His
1               5

<210> SEQ ID NO 56
<211> LENGTH: 330
<212> TYPE: PRT
<213> ORGANISM: Homo sapiens
<220> FEATURE:
<221> NAME/KEY: VARIANT
<222> LOCATION: (97)..(97)
<223> OTHER INFORMATION: site of known allelic variation
<220> FEATURE:
<221> NAME/KEY: VARIANT
<222> LOCATION: (239)..(239)
<223> OTHER INFORMATION: site of known allelic variation
<220> FEATURE:
<221> NAME/KEY: VARIANT
<222> LOCATION: (241)..(241)
<223> OTHER INFORMATION: site of known allelic variation

<400> SEQUENCE: 56

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190
```

-continued

```
His Gln Asp Trp Leu Asn Gly Lys Glu Tyr Lys Cys Lys Val Ser Asn
            195                 200                 205
Lys Ala Leu Pro Ala Pro Ile Glu Lys Thr Ile Ser Lys Ala Lys Gly
        210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 57
<211> LENGTH: 326
<212> TYPE: PRT
<213> ORGANISM: Homo sapiens
<220> FEATURE:
<221> NAME/KEY: VARIANT
<222> LOCATION: (72)..(72)
<223> OTHER INFORMATION: site of known allelic variation
<220> FEATURE:
<221> NAME/KEY: VARIANT
<222> LOCATION: (75)..(75)
<223> OTHER INFORMATION: site of known allelic variation
<220> FEATURE:
<221> NAME/KEY: VARIANT
<222> LOCATION: (76)..(76)
<223> OTHER INFORMATION: site of known allelic variation
<220> FEATURE:
<221> NAME/KEY: VARIANT
<222> LOCATION: (161)..(161)
<223> OTHER INFORMATION: site of known allelic variation
<220> FEATURE:
<221> NAME/KEY: VARIANT
<222> LOCATION: (257)..(257)
<223> OTHER INFORMATION: site of known allelic variation

<400> SEQUENCE: 57

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
        50                  55                  60
Leu Ser Ser Val Val Thr Val Pro Ser Ser Asn Phe Gly Thr Gln Thr
65                  70                  75                  80
Tyr Thr Cys Asn Val Asp His Lys Pro Ser Asn Thr Lys Val Asp Lys
                85                  90                  95
Thr Val Glu Arg Lys Cys Cys Val Glu Cys Pro Pro Cys Pro Ala Pro
            100                 105                 110
Pro Val Ala Gly Pro Ser Val Phe Leu Phe Pro Pro Lys Pro Lys Asp
        115                 120                 125
```

```
Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 58
<211> LENGTH: 377
<212> TYPE: PRT
<213> ORGANISM: Homo sapiens
<220> FEATURE:
<221> NAME/KEY: VARIANT
<222> LOCATION: (59)..(59)
<223> OTHER INFORMATION: site of known allelic variation
<220> FEATURE:
<221> NAME/KEY: VARIANT
<222> LOCATION: (75)..(75)
<223> OTHER INFORMATION: site of known allelic variation
<220> FEATURE:
<221> NAME/KEY: VARIANT
<222> LOCATION: (76)..(76)
<223> OTHER INFORMATION: site of known allelic variation
<220> FEATURE:
<221> NAME/KEY: VARIANT
<222> LOCATION: (221)..(221)
<223> OTHER INFORMATION: site of known allelic variation
<220> FEATURE:
<221> NAME/KEY: VARIANT
<222> LOCATION: (222)..(222)
<223> OTHER INFORMATION: site of known allelic variation
<220> FEATURE:
<221> NAME/KEY: VARIANT
<222> LOCATION: (226)..(226)
<223> OTHER INFORMATION: site of known allelic variation
<220> FEATURE:
<221> NAME/KEY: VARIANT
<222> LOCATION: (239)..(239)
<223> OTHER INFORMATION: site of known allelic variation
<220> FEATURE:
<221> NAME/KEY: VARIANT
<222> LOCATION: (269)..(269)
<223> OTHER INFORMATION: site of known allelic variation
<220> FEATURE:
<221> NAME/KEY: VARIANT
<222> LOCATION: (309)..(309)
```

```
<223> OTHER INFORMATION: site of known allelic variation
<220> FEATURE:
<221> NAME/KEY: VARIANT
<222> LOCATION: (314)..(314)
<223> OTHER INFORMATION: site of known allelic variation
<220> FEATURE:
<221> NAME/KEY: VARIANT
<222> LOCATION: (320)..(320)
<223> OTHER INFORMATION: site of known allelic variation
<220> FEATURE:
<221> NAME/KEY: VARIANT
<222> LOCATION: (327)..(327)
<223> OTHER INFORMATION: site of known allelic variation
<220> FEATURE:
<221> NAME/KEY: VARIANT
<222> LOCATION: (339)..(339)
<223> OTHER INFORMATION: site of known allelic variation
<220> FEATURE:
<221> NAME/KEY: VARIANT
<222> LOCATION: (349)..(349)
<223> OTHER INFORMATION: site of known allelic variation
<220> FEATURE:
<221> NAME/KEY: VARIANT
<222> LOCATION: (352)..(352)
<223> OTHER INFORMATION: site of known allelic variation
<220> FEATURE:
<221> NAME/KEY: VARIANT
<222> LOCATION: (365)..(365)
<223> OTHER INFORMATION: site of known allelic variation
<220> FEATURE:
<221> NAME/KEY: VARIANT
<222> LOCATION: (366)..(366)
<223> OTHER INFORMATION: site of known allelic variation

<400> SEQUENCE: 58

Ala Ser Thr Lys Gly Pro Ser Val Phe Pro Leu Ala Pro Cys Ser Arg
 1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Thr Cys Asn Val Asn His Lys Pro Ser Asn Thr Lys Val Asp Lys
                 85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
```

```
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
                260                 265                 270

Pro Arg Glu Pro Gln Val Tyr Thr Leu Pro Pro Ser Arg Glu Glu Met
                275                 280                 285

Thr Lys Asn Gln Val Ser Leu Thr Cys Leu Val Lys Gly Phe Tyr Pro
                290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
                340                 345                 350

Phe Ser Cys Ser Val Met His Glu Ala Leu His Asn Arg Phe Thr Gln
                355                 360                 365

Lys Ser Leu Ser Leu Ser Pro Gly Lys
                370                 375

<210> SEQ ID NO 59
<211> LENGTH: 327
<212> TYPE: PRT
<213> ORGANISM: Homo sapiens
<220> FEATURE:
<221> NAME/KEY: VARIANT
<222> LOCATION: (289)..(289)
<223> OTHER INFORMATION: site of known allelic variation

<400> SEQUENCE: 59

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
                100                 105                 110

Glu Phe Leu Gly Gly Pro Ser Val Phe Leu Phe Pro Pro Lys Pro Lys
                115                 120                 125

Asp Thr Leu Met Ile Ser Arg Thr Pro Glu Val Thr Cys Val Val Val
                130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
                195                 200                 205
```

```
Pro Ser Ser Ile Glu Lys Thr Ile Ser Lys Ala Lys Gly Gln Pro Arg
    210             215             220

Glu Pro Gln Val Tyr Thr Leu Pro Pro Ser Gln Glu Glu Met Thr Lys
225             230             235             240

Asn Gln Val Ser Leu Thr Cys Leu Val Lys Gly Phe Tyr Pro Ser Asp
            245             250             255

Ile Ala Val Glu Trp Glu Ser Asn Gly Gln Pro Glu Asn Asn Tyr Lys
            260             265             270

Thr Thr Pro Pro Val Leu Asp Ser Asp Gly Ser Phe Phe Leu Tyr Ser
        275             280             285

Arg Leu Thr Val Asp Lys Ser Arg Trp Gln Gln Gly Asn Val Phe Ser
    290             295             300

Cys Ser Val Met His Glu Ala Leu His Asn His Tyr Thr Gln Lys Ser
305             310             315             320

Leu Ser Leu Ser Leu Gly Lys
                325
```

MOLECULES WITH ALTERED NEONATE FC RECEPTOR BINDING HAVING ENHANCED THERAPEUTIC AND DIAGNOSTIC PROPERTIES

CROSS-REFERENCE TO RELATED APPLICATIONS

This application is a continuation of U.S. patent application Ser. No. 15/310,196, filed Nov. 10, 2016, said application Ser. No. 15/310,196 is a U.S. National Stage application of International Application No. PCT/US2015/030964, filed on May 15, 2015, said International Application No. PCT/US2015/030964 claims benefit under 35 U.S.C. § 119(e) of the U.S. Provisional Application No. 61/994,379, filed May 16, 2014. Each of the above listed applications is incorporated by reference herein in its entirety for all purposes.

REFERENCE TO THE SEQUENCE LISTING

This application incorporates by reference a Sequence Listing submitted with this application as text file entitled AEFC-125WO1_SL_ST25.TXT, created on Sep. 10, 2019, and having a size of 35,061 kilobytes.

BACKGROUND

The use of immunoglobulins as therapeutic agents has increased dramatically in recent years and has expanded to different areas of medical treatments. Such uses include treatment of agammaglobulinemia and hypogammaglobulinemia, as immunosuppressive agents for treating autoimmune diseases and graft-vs.-host (GVH) diseases, the treatment of lymphoid malignancies, and passive immunotherapies for the treatment of various systemic and infectious diseases. Also, immunoglobulins are useful as in vivo diagnostic tools, for example, in diagnostic imaging procedures.

The efficacy of immunotherapies and immunodiagnostics can be affected by the persistence of immunoglobulins in the circulation. For example, the rate of immunoglobulin clearance directly affects the amount and frequency of dosage of the immunoglobulin. Rapid clearance may necessitate increased dosage and frequency of dosage, which may in turn cause adverse effects in the patient and also increase medical costs. On the other hand, in certain other diagnostic and therapeutic procedures, rapid clearance of the immunoglobulin may be desirable.

IgG is the most prevalent immunoglobulin class in humans and other mammals and is utilized in various types of immunotherapies and diagnostic procedures. The mechanism of IgG catabolism in the circulation has been elucidated through studies related to the transfer of passive immunity from mother to fetus/neonate through the placenta or yolk sac or through colostrum (maternofetal transfer of IgG via transcytosis) in rodents (Brambell, *Lancet*, ii:1087-1093, 1966; Rodewald, *J. Cell Biol.*, 71:666-670, 1976; Morris et al., In: *Antigen Absorption by the Gut*, pp. 3-22, 1978, University Park Press, Baltimore; Jones et al., *J. Clin. Invest.*, 51:2916-2927, 1972).

A high-affinity Fc receptor, the neonatal Fc receptor (FcRn), has been implicated in this transfer mechanism. The FcRn receptor has been isolated from duodenal epithelial brush borders of suckling rats (Rodewald et al., *J. Cell Biol.*, 99:154s-164s, 1984; Simister et al., *Eur. J. Immunol.*, 15:733-738, 1985) and the corresponding gene has been cloned (Simister et al., *Nature*, 337:184, 1989 and *Cold Spring Harbor Symp. Quant. Biol.*, LIV, 571-580, 1989). The later clonings of FcRn-encoding genes from mice (Ahouse et al., *J. Immunol.*, 151:6076-6088, 1993) and humans (Story et al., *J. Exp. Med.*, 180:2377-2381, 1994) demonstrate high homology of these sequences to the rat FcRn, suggesting a similar mechanism of maternofetal transmission of IgGs involving FcRn in these species.

Meanwhile, a mechanism for IgG catabolism was also proposed by Brambell's group (Brambell et al., *Nature*, 203:1352-1355, 1964; Brambell, *Lancet*, ii:1087-1093, 1966). They proposed that a proportion of IgG molecules in the circulation are bound by certain cellular receptors (i.e., FcRn), which are saturable, whereby the IgGs are protected from degradation and eventually recycled into the circulation; on the other hand, IgGs which are not bound by the receptors are degraded. The proposed mechanism was consistent with the IgG catabolism observed in hypergammaglobulinemic or hypogammaglobulinemic patients. Furthermore, based on his studies as well as others (see, e.g., Spiegelberg et al., *J. Exp. Med.*, 121:323-338, 1965; Edelman et al., *Proc. Natl. Acad. Sci. USA*, 63:78-85, 1969), Brambell also suggested that the mechanisms involved in maternofetal transfer of IgG and catabolism of IgG may be either the same or, at least, very closely related (Brambell, *Lancet*, ii:1087-1093, 1966). Indeed, it was later reported that a mutation in the hinge-Fc fragment caused concomitant changes in catabolism, maternofetal transfer, neonatal transcytosis, and, particularly, binding to FcRn (Ghetie et al., *Immunology Today*, 18(12):592-598, 1997). FcRn has been shown to facilitate both the transfer of maternal IgG to the neonate via the placenta and homeostasis of IgG and albumin levels in adults (Ghetie et al. (1996) Eur. J. Immunol. 26, 690-696; Israel et al. (1996) Immunology 89, 573-578; Ghetie et al. (2000) Annu. Rev. Immunol. 18, 739-766; Roopenian et al. (2007) Nat. Rev. Immunol. 7, 715-725.

These observations suggested that portions of the IgG constant domain control IgG metabolism, including the rate of IgG degradation in the serum through interactions with FcRn. Indeed, increased binding affinity for FcRn increased the serum half-life of the molecule (Kim et al., *Eur. J. Immunol.*, 24:2429-2434, 1994; Popov et al., *Mol. Immunol.*, 33:493-502, 1996; Ghetie et al., *Eur. J. Immunol.*, 26:690-696, 1996; Junghans et al., *Proc. Natl. Acad. Sci. USA*, 93:5512-5516, 1996; Israel et al., *Immunol.*, 89:573-578, 1996).

The interaction between IgG Fc and the neonatal Fc receptor (FcRn) has since been found to be fundamental to IgG homeostasis, resulting in long serum half-life of circulating IgGs. Once antibodies are endocytosed, the FcRn receptor protects antibody from lysogenic degradation by high affinity binding to the antibody in the acidic (pH 6.0) endosome and subsequently releasing the antibody at the neutral cell surface back into circulation.

Various site-specific mutagenesis experiments in the Fc region of mouse IgGs have led to identification of certain amino acid residues involved in the interaction between IgG and FcRn (Kim et al., *Eur. J. Immunol.*, 24:2429-2434, 1994; Medesan et al., *Eur. J. Immunol.*, 26:2533, 1996; Medesan et al., *J. Immunol.*, 158:2211-2217, 1997). These studies and sequence comparison studies found that isoleucine at position 253, histidine at position 310, and histidine at position 435 (according to Kabat numbering, Kabat et al., *Sequences of Proteins of Immunological Interest*, 5th ed., 1991 NIH Pub. No. 91-3242, which is hereby incorporated by reference in its entirety) are highly conserved in human and rodent IgGs, suggesting their importance in IgG-FcRn binding. The scavenger mechanism responsible for the recycling of IgG is highly pH dependent and is facilitated in particular by histidine 310 and 435 in Fc of an IgG at pH ~6. The imidazole side chain of histidine with a pKa of ~6-6.5 has a net neutral charge at pH 7.4, but gains a positive charge in lower pH environments. Thus, both binding affinity and pH dependency of the Fc/FcRn interaction are important regulators of in vivo pharmacokinetic function.

Additionally, various publications describe methods for obtaining physiologically active molecules whose half-lives are modified either by introducing an FcRn-binding polypeptide into the molecules (WO 97/43316; U.S. Pat. Nos. 5,869,046; 5,747,035; WO 96/32478; WO 91/14438) or by fusing the molecules with antibodies whose FcRn-binding affinities are preserved but affinities for other Fc receptors have been greatly reduced (WO 99/43713) or fusing with FcRn binding domains of antibodies (WO 00/09560; U.S. Pat. No. 4,703,039).

Researchers have identified mutations in the IgG constant domain that affect IgG binding to FcRn and/or alter IgG in vivo half-life. For example, WO 93/22332 (by Ward et al.) discloses various recombinant mouse IgGs whose in vivo half-lives are reduced due to mutations in the IgG constant domain. Modulation of IgG molecules by amino acid substitution, addition, or deletion to increase or reduce affinity for FcRn is also disclosed in WO 98/23289. Recently, IgG Fc has been altered to attain molecules that yield longer serum persistence in vivo via enhanced binding to FcRn (Dall'Acqua et al. (2002) J. Immunol. 169, 5171-5180; Dall'Acqua et al. (2006) J. Biol. Chem. 281, 23514-23524; Datta-Mannan et al. (2007) Drug Metab. Dispos. 35, 86-94; Deng et al. (2010) Drug Metab. Dispos. 38, 600-605; Hinton et al. (2004) J. Biol. Chem. 279, 6213-6216; Hinton et al. (2006) J. Immunol. 176, 346-356; Yeung et al. (2009) J. Immunol. 182, 7663-7671); Zalevsky et al. (2010) Nat. Biotechnol. 28, 157-159). IgGs having extended in vivo half-lives as a result of modification of an IgG constant domain are also described in U.S. Pat. Nos. 7,083,784, 7,670,600, 7,704,497, 8,012,476, 8,323,962, 8,475,792 and WO2002/060919 (Dall'Acqua et al.).

SUMMARY

The present invention encompasses polypeptides and other molecules that include at least a portion of an immunoglobulin constant domain that binds to a neonate Fc receptor (FcRn), for example, an Fc region or hinge-Fc region, which contains one or more amino acid modifications (e.g., one or more substitutions, insertions and/or deletions) relative to a wild-type immunoglobulin Fc region. The one or more amino acid modifications change the affinity of the immunoglobulin constant domain, Fc region, or FcRn binding fragment thereof, for the FcRn and alter the serum half-life of the polypeptides or other molecules. The polypeptides and other molecules of the invention find application in therapy, prophylaxis, diagnosis, and prognosis of disease, disorder or infection.

More particularly, the present invention relates to molecules whose in vivo half-lives are affected (increased or decreased) by modification of an IgG constant domain, or an FcRn-binding fragment thereof (such as an Fc region or hinge-Fc region) (e.g., from a human IgG, e.g., human IgG1). The modified molecules of the invention thus include at least an FcRn-binding portion of an Fc region of an immunoglobulin molecule, which contains one or more amino acid modifications as described herein.

The molecules of the invention exhibit altered in vivo half-life by virtue of the presence of an IgG constant domain, or FcRn-binding fragment thereof such as an Fc region or an hinge-Fc region, that is modified (e.g., by amino acid substitution, deletion or insertion) to alter its binding affinity for FcRn. The molecules of the invention thus have altered in vivo half-life and affinity for FcRn relative to comparable unmodified molecules and/or comparable wild type molecules. Optionally, the molecules of the invention additionally exhibit a change (increase or decrease) in the binding affinity of the IgG constant domain, or FcRn-binding fragment thereof such as an Fc region or an hinge-Fc region, for FcRn at a particular pH (e.g., pH 6.0 and/or pH 7.4), relative to comparable unmodified molecules.

In one aspect, the invention relates to immunoglobulins, such as IgG antibodies, that contain an IgG constant domain, or FcRn-binding fragment thereof such as an Fc region or hinge-Fc region, having one or more of these amino acid modifications. In other aspects, the invention also relates to other types of immunoglobulins or fragments thereof (i.e., non-IgG immunoglobulins), non-immunoglobulin proteins and non-protein agents that are fused or conjugated to, or engineered to contain, an IgG constant domain, or FcRn-binding fragment thereof such as an Fc region or hinge-Fc region, having one or more such amino acid modifications. Thus in one aspect, the invention relates to fusion proteins containing an IgG constant domain, or FcRn-binding fragment thereof such as an Fc region or hinge-Fc region, having one or more of these amino acid modifications, and a non-IgG polypeptide covalently linked to such a modified IgG constant domain or FcRn-binding fragment thereof, where the presence of the modified IgG constant domain or fragment thereof increases or decreases the in vivo half-life of the non-IgG protein or molecule. In an exemplary embodiment, the fusion protein includes a non-IgG polypeptide covalently linked to at least an FcRn-binding portion of an Fc region of an IgG molecule. In another aspect, the invention relates to molecules containing an IgG constant domain, or FcRn-binding fragment thereof such as an Fc region or hinge-Fc region, having one or more of these amino acid modifications, and a non-protein agent conjugated to such a modified IgG constant domain or fragment thereof, where the presence of the modified IgG constant domain or fragment thereof increases or decreases the in vivo half-life of the non-protein agent as compared to those conjugated to a wild type IgG1 constant domain or FcRn-binding fragment thereof. In an exemplary embodiment, the molecule includes a non-protein agent conjugated to at least an FcRn-binding portion of an Fc region of an IgG molecule.

In some embodiments, amino acid mutations that shorten in vivo half-life of the modified IgG molecule or FcRn binding fragment thereof, such as an Fc region or hinge-Fc region, of the invention, compared to the wild type IgG molecule or fragment, may nonetheless result in an increase in in vivo half-life when the modified IgG molecule is conjugated to a non-IgG polypeptide or non-protein agent, thereby resulting in slower clearance rates.

In one embodiment of the molecules of the invention, the in vivo half-life is increased relative to a comparable unmodified molecule. Increasing the in vivo half-life of therapeutic and diagnostic IgGs and other bioactive molecules using methods of the invention has many benefits including reducing the amount and/or frequency of dosing of these molecules, for example, in vaccines, passive immunotherapy and other therapeutic and prophylactic methods.

In another embodiment of the molecules of the invention, the in vivo half-life is decreased relative to a comparable unmodified molecule. Decreasing the in vivo half-life of therapeutic and diagnostic IgGs and other bioactive molecules using methods of the invention also has many benefits, including increasing serum clearance rates for IgGs used to remove or neutralize toxic antigens, provide autoimmune therapies, or employed in biological imaging.

The present invention is based upon the inventors' identification of several mutations in the Fc region of a human IgG molecule that alter the binding affinity of the IgG constant domain or FcRn-binding fragment thereof, such an Fc region or hinge-Fc region, for FcRn at a particular pH (e.g., pH 6.0 and/or pH 7.4). Residues 432-437 of the CH3 domain of human IgG1, containing His 435 and referred to herein as the "His435 loop region," were targeted for mutation. An IgG or other molecule containing a modified IgG constant domain or FcRn-binding fragment thereof, such as an Fc region or an hinge-Fc region, according to the invention thus contains one or more mutations at or near one or more of amino acid residues 432, 434, 435, 436 and/or 437 in the CH3 domain of a human IgG1 Fc region, or analogous residues in other IgGs as determined by sequence alignment. The CH3 domain of human IgG1 is in the Fc region of the IgG constant domain, and is shown in FIG. 1D (SEQ ID NO:2); analogous residues in the Fc regions of other IgG molecules can be readily determined by sequence alignment and may likewise serve as mutation sites. In this regard it should be noted that the amino acid sequence of the His435 loop region (positions 432-437) of human IgG1, IgG2 and IgG4 is Leu-His-Asn-His-Tyr-Thr (LHNHYT; SEQ ID NO:8), and that the amino acid sequence of the analogous His435 loop region (positions 432-437) of human IgG3 is Leu-His-Asn-Arg-Phe-Thr (LHNRFT; SEQ ID NO:7, FIG. 1D), which differs from the sequence for human IgG1, IgG2 and IgG3 in that it includes an arginine at position (R435) instead of the histidine (H435), and a phenylalanine at position 436 (F436) instead of the tyrosine (Y436). Further, positions 435 and 436 in human IgG3 represent sites of known allelic variation (see FIG. 1D, shaded boxes and asterisks). In view of the known variations, one of skill in the art will recognize that a histidine at position 435 would represent the wild-type amino acid present in the CH3 domain of an IgG1, IgG2 and IgG4, but would represent an R435H substitution in the CH3 domain of an IgG3. Similarly, a tyrosine at position 436 would represent the wild-type amino acid present in the CH3 domain of an IgG1, IgG2 and IgG4, but would represent an F436Y substitution in the CH3 domain of an IgG3.

Libraries of human IgG1 constant domains with random amino acid mutations introduced into the His 435 loop region were screened for changes in the pH dependence of binding affinity of IgG for FcRn. Both native and mutant IgG base structures were utilized. Exemplary modified IgGs identified via the screening process are shown below in Table I and are described in more detail below. In one embodiment, the modified IgG constant domain or FcRn-binding fragment thereof, such as an Fc region or hinge-Fc region, contains a His435 loop region that includes amino acids selected from: a glutamic acid at position 432, an arginine or alanine at position 433, a tryptophan, serine or phenylalanine at position 434, a histidine at position 435, an arginine at position 436 and/or a glutamine at position 437. In a particular embodiment, a molecule of the invention contains an IgG constant domain, or FcRn-binding fragment thereof such as an Fc region or an hinge-Fc region, having the sequence E(R/A)(W/S/F/Y)HRQ (SEQ ID NO:15) at residues 432-437. In another embodiment, the modified IgG constant domain or FcRn-binding fragment thereof, such as an Fc region or hinge-Fc region, contains a His435 loop region that includes amino acids selected from: a cysteine at position 432, an arginine, histidine, asparagine, proline or serine at position 433, an arginine or tryptophan at position 434, a histidine at position 435, an arginine, isoleucine, leucine, methionine or serine at position 436 and/or a cysteine at position 437. In a particular embodiment, a molecule of the invention contains an IgG constant domain, or FcRn-binding fragment thereof such as an Fc region or hinge-Fc region, having the sequence CSWHLC (mutant "N3"; SEQ ID NO:20) at residues 432-437.

Changes in binding affinity to FcRn at one or more different pHs were shown to affect the in vivo half-life of the IgG. The in vivo half-life, or persistence in serum or other tissues of a subject, of antibodies, and other therapeutic agents and other bioactive molecules is an important clinical parameter which determines the amount and frequency of antibody (or any other pharmaceutical molecule) administration. Accordingly, such molecules, including antibodies and agents coupled to an IgG constant domain or FcRn-binding fragment thereof, such as an Fc region or hinge-Fc region, with changes in half-life are of significant pharmaceutical importance.

In certain embodiments, the molecule of the invention includes an IgG constant domain, or FcRn-binding fragment thereof, such as an Fc region or hinge-Fc region, that has amino acid modifications (e.g., substitutions, insertions and/or deletions) that increase the affinity of the IgG constant domain, or FcRn-binding fragment thereof, for FcRn at pH 6, relative to a wild type molecule or fragment. For example, the molecule of the invention can include an IgG constant domain, or FcRn-binding fragment thereof, such as an Fc region or hinge-Fc region, that exhibits high affinity binding to FcRn at pH 6.0 characterized by a KD of less than about 500 nM. An IgG or other molecule containing a modified IgG constant domain or FcRn-binding fragment thereof (e.g., an Fc region or hinge-Fc region), may exhibit either longer or shorter in vivo half-life than a comparable unmodified molecule, such as wild-type molecule or fragment.

In certain embodiments, the molecule of the invention includes an IgG constant domain, or FcRn-binding fragment thereof, such as an Fc region or hinge-Fc region, has amino acid modifications (e.g., substitutions, insertions and/or deletions) that alter the binding affinity for FcRn at pH 7.4 relative to a wild type molecule or fragment. In one embodiment, for example, the molecule of the invention can include an IgG constant domain, or FcRn-binding fragment thereof, that exhibits binding affinity to FcRn at pH 7.4 characterized by a KD of less than ~1000 nM. In another embodiment, for example, the molecule of the invention can include an IgG constant domain, or FcRn-binding fragment thereof, that exhibits binding affinity to FcRn at pH 7.4 characterized by a KD of more than ~1000 nM. Optionally, the binding affinity of the molecule of the invention to FcRn at pH 7.4 is less than the binding affinity to FcRn at pH 7.4 of a wild type molecule or fragment.

In certain embodiments, the molecule of the invention includes an IgG constant domain, or FcRn-binding fragment thereof, such as an Fc region or hinge-Fc region, has amino acid modifications (e.g., substitutions, insertions and/or deletions) that increase binding affinity for FcRn at both pH 6.0 and pH 7.4, relative to a comparable unmodified molecule, such as a wild type molecule or fragment.

In one embodiment, the molecule of the invention includes an IgG constant domain, or FcRn-binding fragment thereof, such as an Fc region or hinge-Fc region, that exhibits binding affinity to FcRn at pH 6.0 characterized by a KD of less than about 500 nM, and a binding affinity to FcRn at pH 7.4 characterized by a KD of less than ~1000 nM. Optionally, a molecule of this embodiment of the invention may, but need not, possess "abdeg-like" properties as described in more detail below (see, e.g., FIGS. 2A and 5B, quadrant III). A molecule of this embodiment may, but need not, exhibit a shorter in vivo half-life compared to an unmodified molecule, such as a molecule containing a wild type IgG constant domain or FcRn-binding fragment thereof.

In another embodiment, the molecule of the invention includes an IgG constant domain, or FcRn-binding fragment thereof, such as an Fc region or hinge-Fc region, that exhibits binding affinity to FcRn at pH 6.0 characterized by a KD of less than about 500 nM, and a binding affinity to FcRn at pH 7.4 characterized by a KD of more than ~1000 nM but less than the KD of a comparable wild-type molecule at pH 7.4. Optionally, a molecule of this embodiment of the invention may, but need not, possess "YTE-like" properties (see, e.g., FIGS. 2A and 5B, quadrant I). A molecule of this embodiment may, but need not, exhibit a longer in vivo half-life compared to an unmodified molecule, such as a molecule containing a wild type IgG constant domain or FcRn-binding fragment thereof.

In one aspect, the present invention relates to IgGs and other molecules containing a modified Fc region or FcRn-binding fragment thereof (e.g., an Fc region or hinge-Fc region) whose in vivo half-lives are extended by modification of an IgG constant domain or FcRn-binding fragment thereof, such as an Fc region or hinge-Fc region. Increasing the half-life of therapeutic and diagnostic IgGs and other bioactive molecules using methods of the invention has many benefits including reducing the amount and/or frequency of dosing of these molecules, for example, in vaccines, passive immunotherapy and other therapeutic and prophylactic methods. In some embodiments, modified IgGs and other modified molecules of this aspect of the invention that exhibit longer in vivo half-lives are characterized by high affinity binding to FcRn at pH 6, and by a relatively low affinity binding to FcRn at pH 7.4, and optionally an increased pH dependence of binding to FcRn as compared to a wild type IgG. It is expected that the half-lives of these modified IgGs and other molecules can be further extended with additional molecular modifications, such as pI (isoelectric point) engineering, PEGylation, and Pasylation.

In another aspect, the present invention relates to IgGs and other molecules containing a modified IgG constant domain or FcRn-binding fragment thereof (e.g., an Fc region or hinge-Fc region), whose in vivo half-lives are shortened by the modification of an IgG constant domain, or FcRn-binding fragment thereof as compared to unmodified molecules such as those containing a wild type IgG1 constant domain or FcRn-binding fragment thereof. Shortening the half-life of therapeutic and diagnostic IgGs and other bioactive molecules comprising an IgG constant region or FcRn-binding fragment thereof using methods of the invention has many benefits including facilitating rapid clearance of therapeutically or diagnostically useful but toxic antibodies, biologics and other molecules, and facilitating clearance of therapeutic antibodies exhibiting pH-dependent antigen binding. Modified IgGs and other molecules of the invention exhibiting shortened half-lives may be used for imaging, for example, as in positron emission tomography (PET), where rapid clearance and reduced toxicity are important. Some modified IgGs of the invention with shortened half-lives may function as abdegs, with the ability to promote endogenous IgG degradation, thereby ameliorating certain autoimmune diseases characterized by destructive antibodies. In some embodiments, modified IgGs and other modified molecules of this aspect of the invention that exhibit shorter in vivo half-lives are characterized by high affinity binding to FcRn at pH 6, and by an increased affinity to FcRn at pH 7.4, and optionally a reduced pH dependence of binding to FcRn as compared to a wild-type IgG.

In some embodiments, the modified IgG or other molecule of the invention also exhibits low or even reduced binding affinity for FcRn at pH 7.4. Like wild-type IgG, the modified IgG or other molecule of the invention has higher affinity for FcRn at pH 6.0 than at pH 7.4. The observed difference in binding affinity for FcRn at pH 6.0 versus binding affinity for FcRn at pH 7.4 can be used to determine whether the pH dependence of binding to FcRn has increased or decreased, relative to a comparable unmodified molecule, such as a wild-type molecule.

Terminology

Native antibodies and immunoglobulins are usually heterotetrameric glycoproteins of about 150,000 daltons, composed of two identical light (L) chains and two identical heavy (H) chains. Each light chain is linked to a heavy chain by one covalent disulfide bond, and the heavy chains are linked to each other although the number of disulfide linkages varies between the heavy chains of different immunoglobulin isotypes. Each light chain comprises a light chain variable region (abbreviated herein as VL) and a light chain constant region (abbreviated herein as CL). Each heavy chain is comprised of a heavy chain variable region (VH) and a heavy chain constant region (CH) consisting of three domains, CH1, CH2 and CH3. CH1 and CH2, of the heavy chain, are separated from each other by the so-called hinge region. The hinge region normally comprises one or more cysteine residues, which may form disulfide bridges with the cysteine residues of the hinge region of the other heavy chain in the antibody molecule. Antibodies have a variable domain comprising the antigen-specific binding sites and a constant domain which is involved in effector functions.

The term "Fc region", sometimes referred to as "Fc" or "Fc domain", as used herein refers the portion of an IgG molecule that correlates to a crystallizable fragment obtained by papain digestion of an IgG molecule. The Fc region consists of the C-terminal half of the two heavy chains of an IgG molecule that are linked by disulfide bonds. It has no antigen binding activity but contains the carbohydrate moiety and the binding sites for complement and Fc receptors, including the FcRn receptor (see below). The Fc region contains the entire second constant domain CH2 (residues 231-340 of human IgG1, according to the Kabat numbering system) (e.g., SEQ ID NO:1; FIG. 1C) and the third constant domain CH3 (residues 341-447) (e.g., SEQ ID NO:2; FIG. 1D).

The terms "hinge-Fc region", "Fc-hinge region," "hinge-Fc domain" or "Fc-hinge domain", as used herein are used interchangeably and refer to a region of an IgG molecule consisting of the Fc region (residues 231-447) and a hinge region (residues 216-230; e.g., SEQ ID NO:3) extending from the N-terminus of the Fc region. An example of the amino acid sequence of the human IgG1 hinge-Fc region is SEQ ID NO:4 (FIG. 1B-FIG. 1D).

The term "constant domain" refers to the portion of an immunoglobulin molecule having a more conserved amino acid sequence relative to the other portion of the immunoglobulin, the variable domain, which contains the antigen binding site. The heavy chain constant domain contains the CH1, CH2 and CH3 domains and the light chain constant domain contains the CL domain.

A "fusion protein" refers to a chimeric polypeptide which comprising a first polypeptide linked to a second polypeptide with which it is not naturally linked in nature. For example, a fusion protein may comprise an amino acid sequence encoding and Fc region or at least a portion of an Fc region (e.g., the portion of the Fc region that confers binding to FcRn) and a nucleic acid sequence encoding a non-immunoglobulin polypeptide, e.g., a ligand binding domain of a receptor or a receptor binding domain of a ligand. The polypeptides may normally exist in separate proteins that are brought together in the fusion polypeptide or they may normally exist in the same protein but are placed in a new arrangement in the fusion polypeptide. A fusion protein may be created, for example, by chemical synthesis, or by creating and translating a polynucleotide in which the peptide regions are encoded in the desired relationship.

"Linked," "fused," or "fusion" are used interchangeably. These terms refer to the joining together of two or more elements or components, by whatever means, including chemical conjugation or recombinant means. An "in-frame fusion" or "operably linked" refers to the joining of two or more open reading frames (ORFs) to form a continuous longer ORF, in a manner that maintains the correct reading frame of the original ORFs. Thus, the resulting recombinant fusion protein is a single protein containing two or more segments that correspond to polypeptides encoded by the original ORFs (which segments are not normally so joined in nature). Although the reading frame is thus made continuous throughout the fused segments, the segments may be physically or spatially separated by, for example, an in-frame linker sequence.

The term "FcRn receptor" or "FcRn" as used herein refers to an Fc receptor ("n" indicates neonatal) which is known to be involved in transfer of maternal IgGs to a fetus through the human or primate placenta, or yolk sac (rabbits) and to a neonate from the colostrum through the small intestine. It is also known that FcRn is involved in the maintenance of constant serum IgG levels by binding the IgG molecules and recycling them into the serum. The binding of FcRn to naturally occurring IgG1, IgG2, and IgG4 molecules is strictly pH-dependent with optimum binding at pH 6. IgG3 has a known variation at position 435 (i.e., human IgG has R435 instead of H435 found in human IgG1, IgG2 and IgG4), which may result in reduced binding at pH 6. FcRn comprises a heterodimer of two polypeptides, whose molecular weights are approximately 50 kD and 15 kD, respectively. The extracellular domains of the 50 kD polypeptide are related to major histocompatibility complex (MHC) class I α-chains and the 15 kD polypeptide was shown to be the non-polymorphic $\beta_2$-microglobulin ($\beta_2$-m). In addition to placenta and neonatal intestine, FcRn is also expressed in various tissues across species as well as various types of endothelial cell lines. It is also expressed in human adult vascular endothelium, muscle vasculature and hepatic sinusoids and it is suggested that the endothelial cells may be most responsible for the maintenance of serum IgG levels in humans and mice. The amino acid sequences of human FcRn and murine FcRn are indicated by SEQ ID NO:5 and SEQ ID NO:6, respectively. Homologs of these sequences having FcRn activity are also included.

An "FcRn-binding fragment" of an IgG constant domain, as that term is used herein, refers to a fragment of an IgG constant domain that binds to the FcRn receptor. An FcRn-binding fragment of an IgG constant domain can include the Fc region, or the hinge-Fc region; thus it can include portions of the heavy chain CH2-CH3 region or the hinge-CH2-CH3 region that are involved in binding to FcRn (see Roopenian et al., Nature Rev. Immunol. 7:715-725 (2007).

"KD" as that term is used herein (sometimes also referred to as Kd, $K_D$ or $K_d$) is the equilibrium dissociation constant a binding interaction between two molecules, such as an IgG and FcRn. KD can be calculated from observed rate constants for association ($k_{on}$) and dissociation ($k_{off}$), such that KD is equal to the ratio of the $k_{off}/k_{on}$.

The term "in vivo half-life" as used herein refers to a biological half-life of a particular type of IgG molecule or its fragments containing FcRn-binding sites in the circulation of a given animal and is represented by a time required for half the quantity administered in the animal to be cleared from the circulation and/or other tissues in the animal. When a clearance curve of a given IgG is constructed as a function of time, the curve is usually biphasic with a rapid α-phase which represents an equilibration of the injected IgG molecules between the intra- and extra-vascular space and which is, in part, determined by the size of molecules, and a longer β-phase which represents the catabolism of the IgG molecules in the intravascular space. The term "in vivo half-life" practically corresponds to the half-life of the IgG molecules in the β-phase.

An "isolated" or "purified" antibody or fusion protein is substantially free of cellular material or other contaminating proteins from the cell or tissue source from which the protein is derived, or substantially free of chemical precursors or other chemicals when chemically synthesized. The language "substantially free of cellular material" includes preparations of an antibody or a fusion protein in which the antibody or the fusion protein is separated from cellular components of the cells from which it is isolated or recombinantly produced. Thus, an antibody or a fusion protein that is substantially free of cellular material includes preparations of antibody or fusion protein having less than about 30%, 20%, 10%, or 5% (by dry weight) of contaminating protein. In one embodiment, when the antibody or the fusion protein is recombinantly produced, it can also substantially free of culture medium, i.e., culture medium represents less than about 20%, 10%, or 5% of the volume of the protein preparation. In another embodiment, when the antibody or the fusion protein is produced by chemical synthesis, it can be substantially free of chemical precursors or other chemicals, i.e., it is separated from chemical precursors or other chemicals which are involved in the synthesis of the protein. Accordingly such preparations of the antibody or the fusion protein have less than about 30%, 20%, 10%, 5% (by dry weight) of chemical precursors or compounds other than the antibody or antibody fragment of interest. In one embodiment of the present invention, antibodies are isolated or purified. Optionally, fusion proteins are isolated or purified.

An "isolated" nucleic acid molecule is one which is separated from other nucleic acid molecules which are present in the natural source of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. An "isolated" nucleic acid molecule does not include cDNA molecules within a cDNA library. In one embodiment of the invention, nucleic acid molecules encoding antibodies are isolated or purified. Optionally, nucleic acid molecules encoding fusion proteins are isolated or purified.

The term "host cell" as used herein refers to the particular subject cell transfected with a nucleic acid molecule or infected with phagemid or bacteriophage and the progeny or potential progeny of such a cell. Progeny of such a cell may not be identical to the parent cell transfected with the nucleic acid molecule due to mutations or environmental influences that may occur in succeeding generations or integration of the nucleic acid molecule into the host cell genome.

Amino acid residues of the IgG constant and variable domains referred to herein are numbered according to the EU numbering index of Kabat et al. (*Sequences of Proteins of Immunological Interest*, 5th ed., 1991 NIH Pub. No. 91-3242, which is incorporated by reference herein in its entirety), and include corresponding residues in other IgG constant domains as determined by sequence alignment. FIG. 1A-D show the human IgG1 heavy chain constant domain as well as corresponding residues in other IgG constant domains. The names of amino acids referred to herein are abbreviated either with three-letter or one-letter symbols.

To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions×100%). In one embodiment, the two sequences are the same length.

The determination of percent identity between two sequences can also be accomplished using a mathematical algorithm. A non-limiting example of a mathematical algorithm utilized for the comparison of two sequences is the algorithm of Karlin and Altschul, 1990, *Proc. Natl. Acad. Sci. U.S.A.* 87:2264-2268, modified as in Karlin and Altschul, 1993, *Proc. Natl. Acad. Sci. U.S.A.* 90:5873-5877. Such an algorithm is incorporated into the NBLAST and XBLAST programs of Altschul et al., 1990, *J. Mol. Biol.* 215:403. BLAST nucleotide searches can be performed with the NBLAST nucleotide program parameters set, e.g., for score=100, wordlength=12 to obtain nucleotide sequences homologous to a nucleic acid molecules of the present invention. BLAST protein searches can be performed with the XBLAST program parameters set, e.g., to score–50, wordlength=3 to obtain amino acid sequences homologous to a protein molecule of the present invention. To obtain gapped alignments for comparison purposes, Gapped BLAST can be utilized as described in Altschul et al., 1997, *Nucleic Acids Res.* 25:3389-3402. Alternatively, PSI-BLAST can be used to perform an iterated search which detects distant relationships between molecules (Id.). When utilizing BLAST, Gapped BLAST, and PSI-Blast programs, the default parameters of the respective programs (e.g., of XBLAST and NBLAST) can be used (see, e.g., http://www.ncbi.nlm.nih.gov). Another non-limiting example of a mathematical algorithm utilized for the comparison of sequences is the algorithm of Myers and Miller, 1988, *CABIOS* 4:11-17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

The term "about", when used herein in relation to a numerical value, may be inclusive of a range of values of +/−20%, +/−10%, or +/−5%.

It is to be understood that this invention is not limited to specific compositions or process steps, as such may vary. It must be noted that, as used in this specification and claims, the singular form "a", "an" and "the" include plural referents unless the context clearly dictates otherwise.

BRIEF DESCRIPTION OF THE DRAWINGS

FIGS. 1A through 1D show the amino acid sequences (SEQ ID NOs:56-59) and numbering for the IgG heavy chain constant regions (IgG1 (SEQ ID NO:56), IgG2 (SEQ ID NO:57), IgG3 (SEQ ID NO:58) and IgG4 (SEQ ID NO:59)) numbered according to the EU index as set forth in Kabat. The "EU index as set forth in Kabat" refers to the residue numbering of the human IgG1 EU antibody as described in Kabat et al., *Sequences of Proteins of Immunological Interest*, 5th ed., 1991 NIH Pub. No. 91-3242. FIG. 1A-B shows the amino acid sequences and numbering for the CH1 and hinge regions. FIG. 1C shows the amino acid sequences and numbering for the CH2 region. FIG. 1D shows the amino acid sequence and numbering for the CH3 region. Residues which differ as between the IgG1, IgG2, IgG3 and/or IgG4 are shaded, and sites of known allelic variation are indicated by an asterisk (*). FIG. 1E shows a human neonatal Fc receptor (FcRn) large subunit p51 amino acid sequence (SEQ ID NO:5) which forms a complex with beta-2-microglobulin (also known as p14). FIG. 1F shows a representative human beta-2-microglobulin amino acid sequence (SEQ ID NO:6). Due to known allelic variations, slight differences between the presented sequences and sequences in the prior art may exist.

FIG. 4A shows SequenceLogo (Crooks et al., 2004 *Genome Res.* 14:1188-1190; Schneider and Stephens, 1990 *Nucleic Acids Res.* 18:6097-6100) representations of amino acids 432-437 are shown for 52 phage clones isolated after 4 rounds of phage panning for the CXXXXCE library. FIG. 4B shows the same for 6 clones deemed to have improved pH dependency via phage ELISA. FIG. 4C shows SequenceLogo representations of amino acids 432-437 (SEQ ID NO:23) for 68 phage clones isolated after 4 rounds of phage panning for the ZXXHXZ (SEQ ID NO:14) library.

FIG. 5A shows representative phage ELISA data comparing pH 7.4 and pH 6.0 hFcRn binding as well as sequences of variants from the CXXXXCE (SEQ ID NO:10) library not grouping with N3E-YTE.

FIG. 6A shows IgG levels for wild type (●), YTE (■), Y31-YTE (▼) and N3E-YTE (▲) versions of Motavizumab in hFcRn mice.

FIGS. 7A and B show the results of immunogenicity (T-cell proliferation assay) using PBMCs from 202 donors. Donors were chosen to mirror the Caucasian HLA diversity and represent greater than a dozen HLA-DRB1 allotypes. Motavizumab (wt), N3 Motavizumab, Buffer (PBS) and Keyhole limpet hemocyanin (KLH, a known immunogenic protein) were used as antigens. The antigens were given to PBMCs and allowed to incubate 14 days. T-cell proliferation was measured by FACs. Data are reported as Stimulation Index (SI). FIG. 7A shows a table showing the SI and significance of the four groups tested. FIG. 7B shows the SI of individual donors.

FIG. 10A shows classic pinocytosis.

DETAILED DESCRIPTION OF ILLUSTRATIVE EMBODIMENTS

Figure 2A:
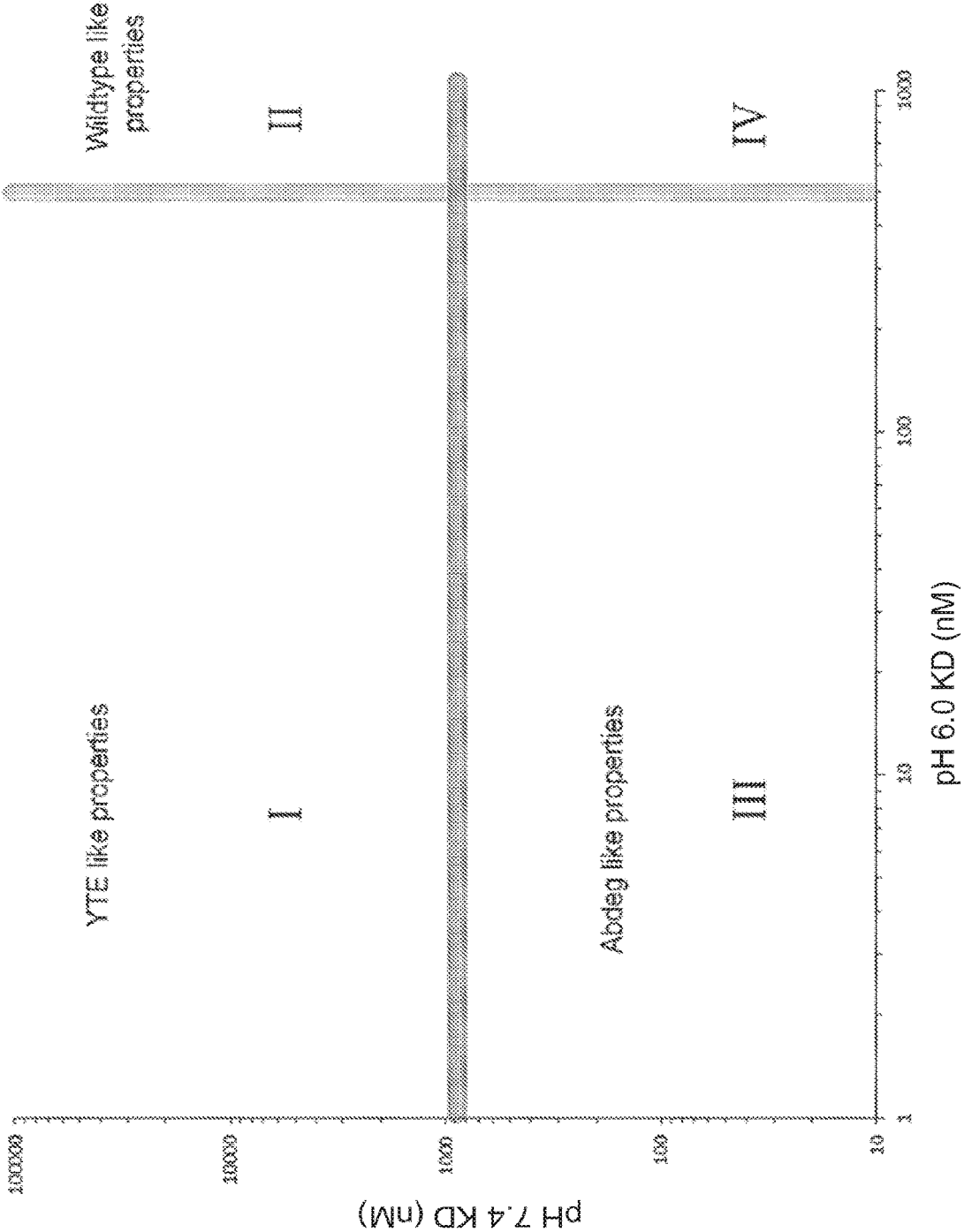
FIG. 2A shows a two-dimensional space defined by binding affinity (KD values) of the IgG Fc fragment to the human FcRn (hFcRn) at pH 6.0 (x-axis) and pH 7.4 (y-axis). The plane is divided into quadrants that may be associated with varying pharmacokinetic properties.

Therapeutic antibodies, diagnostic antibodies, and Fc-fused biologics exploit FcRn-mediated recycling to achieve serum half-lives that can be similar to or different from that of endogenous IgG, depending on the desired properties. By further endowing biological therapeutic and diagnostic agents with improved pharmacokinetic properties, the present invention provides opportunities for more desirable dosages, reduced frequency of administration, or improved clearance, while maintaining efficacy.

The present invention provides molecules, particularly proteins, more particularly, immunoglobulins whose in vivo half-lives are altered (increased or decreased) by the presence of an IgG constant domain, or FcRn binding fragment thereof (e.g., an Fc region or hinge-Fc region) (e.g., from a human IgG, e.g., human IgG1), that have modifications of one or more of amino acid residues in at least the CH3 domain. The modifications can include amino acid substitutions, insertions, deletions, or any combination thereof. It should be understood that all references to amino acid residues of the IgG constant and variable domains that appear herein are numbered according to the EU numbering index of Kabat et al. (*Sequences of Proteins of Immunological Interest,* 5th ed., 1991 NIH Pub. No. 91-3242, which is incorporated by reference herein in its entirety), and include corresponding residues in other IgG constant domains as determined by sequence alignment.

More particularly, the invention provides molecules, particularly proteins, more particularly, immunoglobulins whose in vivo half-lives are altered (increased or decreased) by the presence of an IgG constant domain, or FcRn binding fragment thereof (e.g., an Fc region or hinge-Fc region) (e.g., from a human IgG, e.g., human IgG1), that have modifications of one or more of amino acid residues 432, 433, 434, 435, 436, or 437, and/or that have a single amino acid insertion between amino acids 437 and 438, which insertion is referred to herein as 437*, in the His435 loop region of the CH3 domain, which amino acid substitutions and/or insertions alter (increase or decrease) the binding affinity of the IgG constant domain or FcRn-binding fragment thereof for FcRn at a particular pH (e.g. pH 6.0 or pH 7.4) Such modifications, including insertions between residues 437 and 438, will be referred to generally as modifications within the His435 loop region, i.e., at amino acid residues 432-437. In certain embodiments, these modifications can exclude residue 435, such that the modified IgG constant domain, or FcRn-binding portion thereof (e.g., an Fc region or hinge-Fc region), contains His435 which is found in wild-type human IgG1, IgG2, and IgG4. In certain embodiments, for example modification of the analogous His435 loop region in human IgG3 which in the wild-type molecule includes the arginine at position (R435) instead of the histidine (H435) found in IgG1, IgG2 and IgG4 and further, is a site of known allelic variation (see FIG. 1D, shaded boxes and asterisks), these modifications include the substitution of a wild-type nonhistidine residue 435 with a histidine, to yield H435. In one embodiment, the modified IgG constant domain, or FcRn-binding portion thereof (e.g., an Fc region or hinge-Fc region), is a human or humanized IgG constant domain or FcRn-binding portion thereof, although it may be murine. The human or humanized IgG constant domain can be a constant domain from an IgG1, IgG2, IgG3 or IgG4 domain, or any subtype thereof.

In one aspect, the invention addresses the pharmaceutical importance of increasing the in vivo half-lives of immunoglobulins and other bioactive molecules. To this end, the invention provides IgGs and other molecules containing a modified IgG constant domain or FcRn-binding fragment thereof (e.g., an Fc region or hinge-Fc region) (e.g., from a human IgG, e.g., human IgG1) that confer increased in vivo half-life on immunoglobulins and other bioactive molecules. In this aspect, the present invention relates to an IgG or other molecule (e.g., a protein, but may be a non-protein agent) that has an increased in vivo half-life by virtue of the presence of a modified IgG constant domain, or FcRn-binding fragment thereof (e.g., an Fc region or hinge-Fc region) (e.g., from a human IgG, e.g., human IgG1) wherein the IgG constant domain, or fragment thereof, is modified (e.g., by amino acid substitution, deletion or insertion) to change (increase or decrease) in the binding affinity of the IgG constant domain or FcRn-binding fragment for FcRn at a particular pH (e.g. pH 6.0 or pH 7.4). In one embodiment, the IgG constant domain, or FcRn-binding fragment thereof, is modified to increase the binding affinity for FcRn at pH 6.0 relative to the binding affinity for FcRn at pH 7.4. The in vivo half-lives of the modified IgGs of the invention can be conveniently evaluated in a human transgenic mouse model or a cynomolgus monkey primate model, as described in more detail in the examples below.

In another aspect, the invention addresses the pharmaceutical importance of shortening the in vivo half-lives of immunoglobulins and other bioactive molecules covalently linked to an IgG constant domain, or a fragment thereof that binds to FcRn (e.g., an Fc region or hinge-Fc region). To this end, the invention provides IgGs and other molecules containing a modified IgG constant domain or FcRn-binding fragment thereof (e.g., an Fc region or hinge-Fc region) (e.g., from a human IgG, e.g., human IgG1) that confer reduced in vivo half-life on immunoglobulins and other bioactive molecules covalently linked to an IgG constant domain, or a fragment thereof that binds to FcRn. In this aspect, the present invention relates to an IgG or other molecule (e.g., a protein or a non-protein agent) covalently linked to an IgG constant domain, or a fragment thereof that binds to FcRn (e.g., an Fc region or hinge-Fc region) (e.g., from a human IgG, e.g., human IgG1), that has a reduced in vivo half-life by virtue of the presence of a modified IgG constant domain, or FcRn-binding fragment thereof, wherein the IgG constant domain, or fragment thereof, is modified (e.g., by amino acid substitution, deletion or insertion) to alter the binding affinity of the IgG constant domain, or fragment thereof, for FcRn, at one or more pHs; for example, but not by way of limitation, by maintaining or increasing the binding affinity for FcRn, at pH 6.0 and concurrently increasing the binding affinity for FcRn at pH 7.4.

Most modified IgGs of the invention, whether they exhibit increased or decreased in vivo half-lives compared to each other or their unmodified or wild-type counterparts, contain an IgG constant domain, or FcRn-binding fragment thereof, that exhibits higher binding affinity toward FcRn at pH 6.0 than wild-type IgG constant domain.

More generally, one skilled in the art will understand that the Fc variants of the invention, whether they exhibit increased or decreased in vivo half-lives compared to each other or their unmodified or wild-type counterparts, may have altered FcRn binding properties. Examples of binding properties include but are not limited to, binding specificity, equilibrium dissociation constant (KD), dissociation and association rates (Kon, and Koff respectively), binding affinity and/or avidity. It is well known in the art that the equilibrium dissociation constant (KD) is defined as $k_{off}/k_{on}$. It is understood that a higher affinity interaction will have a lower KD and conversely that a lower affinity interaction will have a higher KD. However, in some instances the value $K_{on}$ or $K_{off}$ may be more relevant than the value of the KD. While the relationships among IgG binding affinity for FcRn, the pH dependence of such binding affinity, and in vivo half-life are complex, it has been discovered that, for those IgG constant domains that exhibit high affinity binding to FcRn at pH 6.0 (e.g., KDs of less than about 500 nM), as the binding affinity for FcRn at pH 7.4 increases (generally reflecting reduced pH dependence of FcRn binding), for example, if the KD at pH 7.4 falls below about 1 µM into the nanomolar ranged, the result can in some instances be a shorter in vivo half-life for the modified IgG (see, e.g., quadrant III in FIGS. 2A and 5B, discussed in more detail below).

In contrast, reduced binding affinity for FcRn at pH 7.4 (e.g., KDs at pH 7.4 above about 1 µM) coupled with high binding affinity at pH 6.0 (e.g., KDs of less than about 500 nM), generally reflecting a greater pH dependence of FcRn binding, can in some instances result in a longer in vivo half-life (see, e.g., quadrant I in FIGS. 2A and 5B, discussed in more detail below).

In some embodiments, modified IgGs and other molecules of the invention contain a modified IgG constant domain or FcRn-binding fragment thereof (e.g., an Fc region or hinge-Fc region), that exhibits a KD for binding to FcRn at pH 6.0 of less than 100 nM, less than 200 nM, less than 300 nM, less than 400 nM, less than 500 nM or less than 1000 nM. Modified IgGs of the invention can, for example, be characterized by KD values for FcRn binding at pH 6.0 of 10 nM to 500 nM, 50 nM to 500 nM. In some embodiments, the modified IgG of the invention exhibits at least a 10-fold enhancement, at least a 20-fold enhancement, or at least a 50-fold enhancement of binding affinity for FcRn at pH 6.0 compared to a wild-type IgG constant domain, or FcRn-binding fragment thereof.

Additionally or alternatively, a modified IgG can exhibit a binding affinity for FcRn at pH 7.4 that is between 10 nM and 50 µM. Without intending to be bound by theory, it is observed that a threshold may exist: at pH 7.4, a KD of about 1 µM or higher (e.g., a KD of 1 µM, 5 µM 10 µM, 20 µM, 30 µM, 40 µM, 50 µM, or higher; that is, binding affinities in the micromolar or millimolar range evidencing lower binding affinity for FcRn) may be associated with a modified IgG or other molecule having enhanced half-life (slower clearance), while a KD of less than 1 µM at pH 7.4 (e.g., a KD of 50 nM, 100 nM, 200 nM, 500 nM, 800 nM up to about 1000 nM; that is, binding affinities in the nanomolar range, evidencing higher binding affinity for FcRn) may be associated with a modified IgG or other molecule having a shortened half-life (faster clearance). An increased half-life for the modified IgG or other molecule is generally, but not always, associated with pH-dependent binding to FcRn characterized by a KD of 50 nM to 400 nM or 500 nM for binding at pH 6, and a KD of more than 1 µM at pH 7.4.

FIG. 2A shows a coordinate plane defined by KD values for binding of IgG to FcRn at pH 6.0 (x-axis) and pH 7.4 (y-axis). Four quadrants are shown, but it should be understood that the quadrants may overlap with each other since the relationship between the pH dependence of FcRn binding and various pharmacokinetic properties, such as half-life and serum clearance, are complex.

Figure 2B:
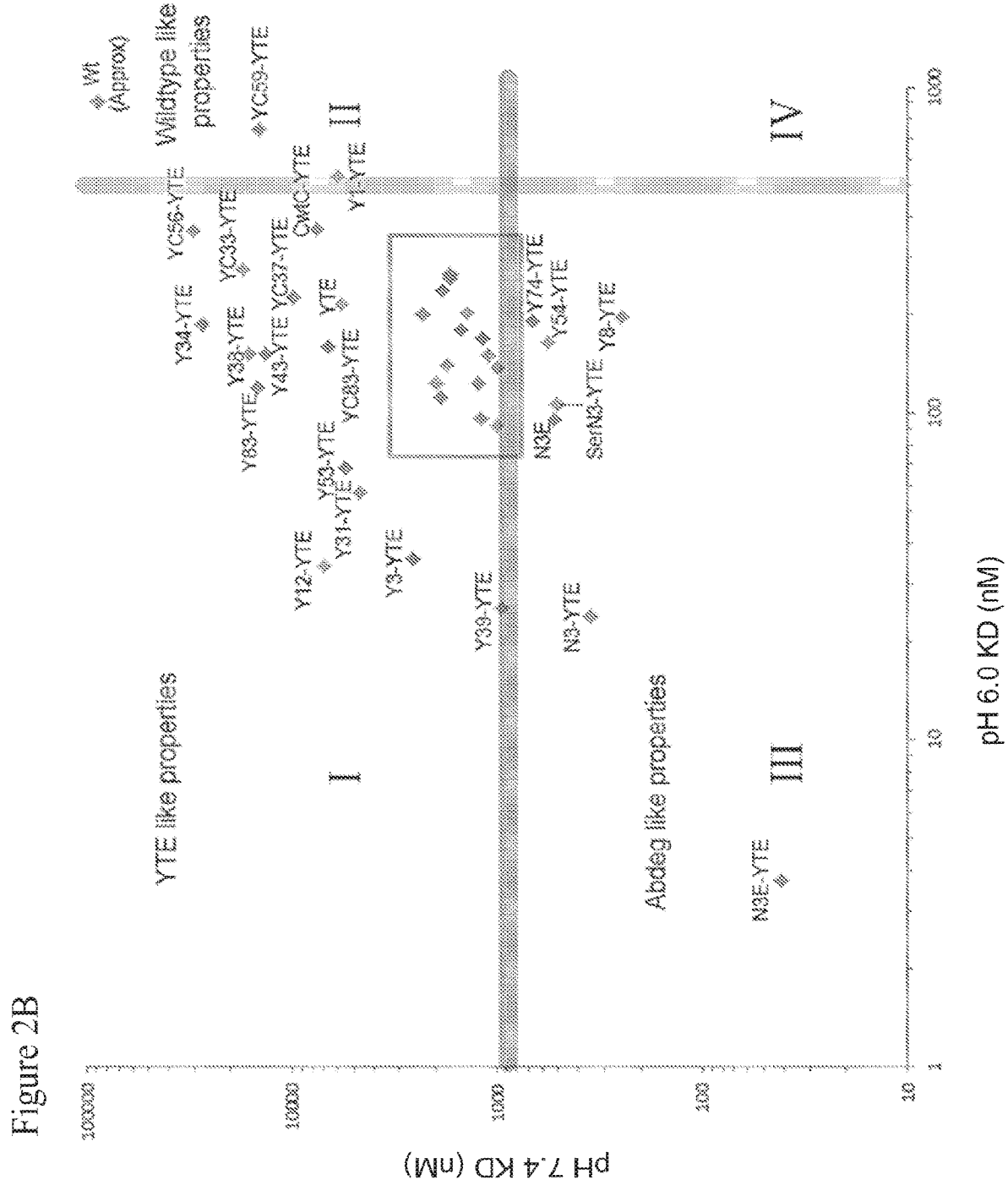
FIG. 2B shows a scatter plot showing hFcRn binding for selected anti-CD20 variants at pH 6.0 and 7.4.
Figure 2C:
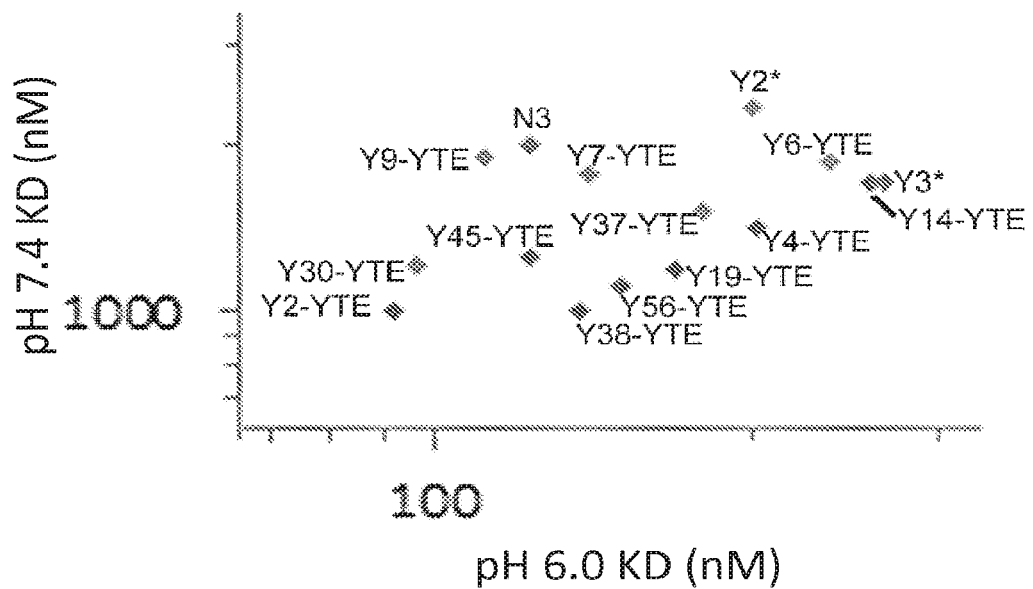
FIG. 2C displays a scatter plot of the inset box from FIG. 2B showing hFcRn binding for selected anti-CD20 variants.

IgGs that fall into quadrant I show high binding affinity for FcRn at pH 6.0 (higher than wild-type) and relatively low binding affinity at pH 7.4. The result is generally greater pH dependence of binding to FcRn, which may be associated with longer in vivo half-lives for these IgGs. FIG. 2B shows exemplary mutant IgGs that fall quadrant I. One such mutant is referred to herein as "YTE." YTE has an IgG constant domain having mutations in the CH2 domain (i.e., M252Y/S254T/T256E). The YTE mutant has enhanced binding affinity for FcRn at pH 6.0 and relatively low binding affinity at 7.4, and exhibits a 3-4 fold increase in in vivo half-life and clearance, compared to a wild-type IgG constant domain. This mutation is among the best identified to extend IgG half-life and is described in more detail in U.S. Pat. No. 7,083,784, issued Aug. 1, 2006, and PCT publication WO 2002/060919, published Aug. 8, 2002. Modified IgGs of the invention that fall in to quadrant I are therefore sometimes referred to herein as "YTE-like" or having "YTE-like" properties. Exemplary modified IgGs of the invention with "YTE-like" properties, whose structures are described in Table I, are shown in quadrant I in FIGS. 2B and 2C and include, but are not limited to, N3, Y31, Y12, YC37-YTE, YC56-YTE, Y3-YTE, Y31-YTE, Y12-YTE, Y83-YTE, Y37-YTE and Y9-YTE.

Modified IgGs of the invention that fall into quadrant II exhibit binding affinity for FcRn at pH 6.0 that is not as high as YTE (i.e., that is more similar to wild-type IgG binding affinity), and binding affinity at pH 7.4 that is also not very high. Wild-type IgG is an exemplary IgG in quadrant II. YC59-YTE (Table I) also falls into quadrant II and is expected to have wild-type properties.

Quadrant III includes modified IgGs that exhibit binding affinity for FcRn that is not only high at pH 6.0, but that is also significantly higher than wild-type levels at pH 7.4. For these molecules, less pH dependence is generally observed in their binding affinities for FcRn. The high binding affinity at pH 7.4 can manifest in short in vivo IgG half-lives and fast clearance rates. Without intending to be bound by theory, it is believed that these pharmacokinetic properties may result from tighter binding of the immunoglobulin to its receptor on the cell surface which in turn may inhibit release of the IgG into serum or tissue, thereby losing benefit of FcRn mediated recycling, and may also prevent endogenous IgG utilizing the FcRn for recycling, overall yielding decreased IgG levels in circulation. It is expected that modified IgGs with shortened half-lives, as well as those with abdeg-like properties (Vaccaro et al., Nature Biotechnol., 2005, 10(23): 1283-1288) are likely to fall within quadrant III. Abdegs, with enhanced binding affinity for FcRn at both pH 6.0 and pH 7.4, are potentially useful as autoimmune drugs, given their ability to lower endogenous IgG levels (Vaccaro et al., Nature Biotechnol., 2005, 10(23):1283-1288). Modified IgGs with enhanced binding affinity for FcRn at both pH 6.0 and 7.4 may also have utility in quickly sweeping away soluble antigens from serum and tissue. Examples of modified IgGs that fall into quadrant III and may exhibit abdeg properties include N3-YTE and N3E-YTE (Table 1). Modified IgGsY54-YTE, SerN3-YTE and Y8-YTE also exhibit increased binding to FcRn at pH 7.4 and are located in quadrant III of the graph in FIG. 2B.

Modified IgGs that fall into quadrant IV may not be efficiently recycled, since binding to FcRn within the acidic endosome may be compromised. Moreover, high binding affinity for FcRn at pH 7.4 may prevent their release into serum or tissue.

In addition to modifications within His435 loop region, residues 432-437, the modified IgG constant domain, or FcRn-binding fragment thereof (e.g., an Fc region or hinge-Fc region), can include one or more modifications at other sites in the IgG constant domain, or FcRn-binding fragment thereof. In other words, mutations in the His 435 region described herein can be incorporated into or superimposed onto an IgG constant domain or FcRn-binding fragment thereof (e.g., an Fc region or hinge-Fc region), or other molecules that have already been engineered to have other desirable characteristics relating to stability, specificity, binding affinity, and the like. For example, the constant domain, or fragment thereof, can be further modified by substitution of one or more of amino acid residues 251-256, 285-290, 308-314, 385-389, and 428-431 that increase the affinity of the constant domain or FcRn-binding fragment thereof for FcRn, as described in U.S. Pat. No. 7,083,784, issued Aug. 1, 2006, and PCT publication WO 2002/060919, published Aug. 8, 2002. The one or more additional modifications can include amino acid substitutions, insertions, deletions, or any combination thereof. Modifications can include, for example, modifications at one or more surface-exposed residues, and the modification can be a substitution with a residue of similar charge, polarity or hydrophobicity to the residue being substituted.

The structure of the IgG constant domain (or FcRn-binding fragment thereof, e.g., an Fc region or hinge-Fc region) outside the His435 loop region may be referred to herein as the molecule's IgG "base structure" or "background" and these two terms are used interchangeably. The invention thus contemplates modified IgGs with mutations in the His435 loop region incorporated into either a wild-type IgG base structure or a mutant IgG base structure. Any mutant IgG base structure can be utilized; exemplary but nonlimiting mutant IgG base structures are described herein. "YTE" as described in more detail below is an example of a mutant IgG base structure.

One embodiment of the immunoglobulin or other bioactive molecule of the invention contains an IgG constant domain, or FcRn-binding fragment thereof (e.g., and Fc region or hinge-Fc region) (e.g., from a human IgG, e.g., human IgG1), having amino acid modifications at one or more of positions 251, 252, 254, 255, and 256, in the CH2 domain; more specifically, having substitutions at one or more of these positions. In specific embodiments, residue 251 is substituted with leucine or arginine, residue 252 is substituted with tyrosine, phenylalanine, serine, tryptophan or threonine, residue 254 is substituted with threonine or serine, residue 255 is substituted with leucine, glycine, isoleucine or arginine, and/or residue 256 is substituted with serine, arginine, glutamine, glutamic acid, aspartic acid, alanine, asparagine or threonine. In a more specific embodiment, residue 251 is substituted with leucine, residue 252 is substituted with tyrosine, residue 254 is substituted with threonine or serine, and/or residue 255 is substituted with arginine. In yet another specific embodiment, residue 252 is substituted with phenylalanine and/or residue 256 is substituted with aspartic acid. In a specific embodiment, residue 251 is substituted with leucine, residue 252 is substituted with tyrosine, residue 254 is substituted with threonine or serine, and/or residue 255 is substituted with arginine. In another specific embodiment, residue 252 is substituted with tyrosine, residue 254 is substituted with threonine, and residue 256 is substituted with glutamic acid (M252Y/S254T/T256E, referred to here as "YTE"). Many of the modified IgG constant regions, or FcRn-binding fragments thereof described herein include a "YTE" base structure. Any combination of these substitutions can be used in the base structure.

Some embodiments of the immunoglobulin or other bioactive molecule of the invention contain an IgG constant domain, or FcRn-binding fragment thereof (e.g., an Fc region or hinge-Fc region) (e.g., from a human IgG, e.g., human IgG1), having amino acid modifications at one or more of position 308, 309, 311, 312, and 314, more specifically, having substitutions at one or more of positions 308, 309, 311, 312 and 314 with threonine, proline, serine, aspartic acid and leucine respectively. In one embodiment, residues at one or more of positions 308, 309, and 311 are substituted with isoleucine, proline, and glutamic acid, respectively. In one embodiment, residues at one or more of positions 308, 309, 311, 312, and 314, are substituted with threonine, proline, serine, aspartic acid, and leucine, respectively. Any combination of these substitutions can be used in the base structure.

Some embodiments of the immunoglobulin or other bioactive molecules of the invention contain an IgG constant domain, or FcRn-binding fragment thereof (e.g., an Fc region or hinge-Fc region) (e.g., from a human IgG, e.g., human IgG1), having amino acid modifications at one or more positions 385, 386, 387, and 389, more specifically, having substitutions at one or more of these positions. In specific embodiments, residue 385 is substituted with arginine, aspartic acid, serine, threonine, histidine, lysine, or alanine, residue 386 is substituted with threonine, proline, aspartic acid, serine, lysine, arginine, isoleucine, or methionine, residue 387 is substituted with arginine, histidine, serine, threonine, alanine, or proline and/or residue 389 is substituted with proline or serine. In more specific embodiments, residues at one or more positions 385, 386, 387, and 389 are substituted with arginine, threonine, arginine, and proline, respectively. In yet another specific embodiment, residues at one or more positions 385, 386, and 389 are substituted with aspartic acid, proline, and serine, respectively. Any combination of these substitutes can be used in the base structure.

Some embodiments of the immunoglobulin or other bioactive molecules of the invention contain an IgG constant domain, or FcRn-binding fragment thereof (e.g., an Fc region or hinge-Fc region) (e.g., from a human IgG, e.g., human IgG1), having amino acid modifications at position 428. In specific embodiments, residue 428 is substituted with methionine, threonine, leucine, phenylalanine, or serine. In one embodiment, residue 428 is substituted with methionine.

Molecules of the invention thus contain at least one modification of amino acid residues in the His435 loop region, that is, residues 432, 433, 434, 435, 436, or 437, and/or an amino acid insertion between amino acids 437 and 438, and may optionally also include any combination of the above-described substitutions including but not limited to substitutions at one or more of residues 251, 252, 254, 255, 256, 308, 309, 311, 312, 385, 386, 387, 389, and/or 428.

Included within the invention are pharmaceutical compositions and methods of prophylaxis and therapy using modified immunoglobulins, proteins and other bioactive molecules of the invention having extended half-lives. Also included are methods of diagnosis using modified immunoglobulins, proteins and other bioactive molecules of the invention having extended half-lives.

Mutations Associated with Altered In Vivo Half-Lives

The invention relates to amino acid modifications (e.g, substitutions, insertions or deletions) in the IgG constant domain, or FcRn binding fragment thereof (e.g., an Fc region or hinge-Fc region), that have been discovered to increase the affinity of the IgG constant domain, or fragment thereof, for FcRn at pH 6, and that optionally alter the affinity of the IgG or fragment thereof for FcRn at pH 7.4, thereby altering the pH dependence of binding affinity of the IgG constant domain, or fragment thereof (e.g., an Fc region or hinge-Fc region) for FcRn. Further, these modifications may either increase or decrease the in vivo half-life of the molecule.

The invention is based upon identification of amino acid modifications in the His 435 loop region of the CH3 domain of the Fc fragment of human IgG (SEQ ID NO:7 or 8), which affect the binding affinity of the modified IgG, or fragment thereof, to FcRn at one or more pHs. These modifications may result in an alteration in the pH dependence of binding of IgG, or fragment thereof, to FcRn. In some embodiments, the amino acid modifications in the His435 loop region can result in a higher binding affinity of the IgG constant domain, or FcRn-binding fragment thereof, for FcRn at pH 6, at pH 7.4, or at both pH 6.0 and 7.4, than exhibited by the wild-type IgG constant domain. Additionally or alternatively, the modifications may affect the in vivo half-life of the molecule.

The His435 loop region includes amino acid residues 432, 433, 434, 435, 436 and 437. The wild type amino acid sequence of the His435 loop region (residues 432 to 437) of the CH3 domain of the Fc fragment of human IgG1, IgG2 and IgG4 is Leu-His-Asn-His-Tyr-Thr (SEQ ID NO:8) and of human IgG3 is Leu-His-Asn-Arg-Phe-Thr (SEQ ID NO:7). In some embodiments, the one or more amino acid modifications are made in or near one or more of residues 432, 433, 434, 435, 436 and 437 in a human IgG constant domain, or FcRn-binding domain thereof (e.g., an Fc region or hinge-Fc region), or analogous residues thereof, as determined by amino acid sequence alignment, in other IgGs. Such mutations include amino acid substitutions as well as deletions and insertions. An illustrative site for an amino acid insertion is between residues 437 and 438, which added position is referred to herein as 437*.

In one embodiment of the modified IgG constant domain, or FcRn-binding fragment thereof (e.g., an Fc region or hinge-Fc Fc region), residue 435 is maintained as a histidine (His435) (as in wild-type human IgG1, IgG2 and IgG4) or mutated to a histidine (as in IgG3, which natively contains R435, and is thus mutated to R435H)), while at least one of residues 432, 433, 434, 436, or 437 is substituted, and/or an insertion is made at position 437*. In one embodiment, neither residue 435 (His435) nor residue 433 (His 433) is mutated (except that, for human IgG3, residue 435 has the R435H mutation so that it is His435), while at least one of residues 432, 434, 436, or 437 is substituted, and/or an insertion is made at position 437*. In one embodiment, the FcRn binding domain has a substitution at 1, 2, 3, 4, or all 5 of residues 432, 433, 434, 436, 437, and/or has an insertion at position 437* in the His435 loop region. In another embodiment, the FcRn binding domain has a substitution at three or more of positions 432, 433, 434, 435, 436 or 437. In another embodiment, the FcRn binding domain has a substitution at four or more of positions 432, 433, 434, 435, 436 or 437.

In one embodiment, at least one of positions 432 and 437 is substituted with cysteine, and residues 433, 434, 435, and 436 are each independently either substituted or not substituted. In certain embodiments, residues 432 and 437 are both substituted with cysteines, and residues 433, 434, 435, and 436 are each independently either substituted or not substituted.

In one embodiment, at least one of positions 432 and 437 is substituted with an amino acid selected from the group consisting of glutamine, glutamic acid, aspartic acid, lysine, arginine, and histidine, and residues 433, 434, 435, and 436 are each independently either substituted or not substituted. In certain embodiments, both of positions 432 and 437 are substituted with an amino acid independently selected from the group consisting of glutamine, glutamic acid, aspartic acid, lysine, arginine, and histidine, and residues 433, 434, 435, and 436 are each independently either substituted or not substituted.

In one embodiment, a modified IgG constant domain, or FcRn-binding fragment thereof (e.g., an Fc region or hinge- Fc region), contains at least three mutations in the His435 loop region, and has a histidine at position 435 (the histidine at position 435 may be a wild type residues or a mutation). Any of the various permutations of three or more mutations (not including a mutation at 435, if present) is encompassed by the invention, including without limitation mutations at the following sites:

Positions: 432, 433, and any one of 434, 436, 437 and 437*
Positions: 432, 434, and any one of 436, 437 and 437*
Positions: 432, 436, and any one of 437 and 437*
Positions: 432, 437, and 437*
Positions: 433, 434, and any one of 436, 437 and 437*
Positions: 433, 436, and any one of 437 and 437*
Positions: 433, 437 and 437*
Positions: 434, 436 and any one of 437 and 437*
Positions: 434, 437 and 437*
Positions: 436, 437 and 437*
Positions: 432, 433, 434 and any one of 436, 437 and 437*
Positions: 432, 433, 436 and any one of 437 and 437*
Positions: 432, 433, 437 and 437*
Positions: 432, 434, 436, and any one of 437 and 437*
Positions: 432, 434, 437 and 437*
Positions: 432, 436, 437 and 437*
Positions: 433, 434, 436, and any one of 437 an d 437*
Positions: 433, 434, 437 and 437*
Positions: 434, 436, 437 and 437*
Positions: 432, 433, 434, 436, and any one of 437 and 437*
Positions: 432, 433, 434, 437 and 437*
Positions: 432, 433, 436, 437 and 437*
Positions: 432, 434, 436, 437 and 437*
Positions: 433, 434, 436, 437 and 437*
Positions: 432, 433, 434, 436, 437, and 437*

In one embodiment of the modified IgG constant domain, or FcRn-binding fragment thereof (e.g., an Fc region or hinge-Fc region), the His435 loop region of the CH3 domain of the Fc fragment has the amino acid sequence CXXXXC (residues 432-437; SEQ ID NO:9) or CXXXXCE (residues 432 through 437* wherein 437* is an insertion; SEQ ID NO:10). Exemplary His435 loop amino acid sequences for various HB20.3 IgG mutants generated from a CXXXXCE (SEQ ID NO:10) library are shown in Table 1 (Example 1). Binding data for binding of the various HB20.3 IgGs mutants to human FcRn are also shown. Without intending to be bound by theory, the two cysteine residues may exert a stabilizing effect on the loop region, possibly by forming a disulfide cystine. The predicted distance between the two cysteines is about 6.7 A, which is within the range (4.6-7 A) compatible with the formation of a cystine. In certain embodiments based on the His435 loop motif CXXXXC (SEQ ID NO:9), the amino acid modifications for a modified IgG constant domain, or FcRn-binding fragment thereof (e.g., an Fc region or hinge-Fc region), are substitutions at one or more of positions 432-437, with both of positions 432 and 437 being substituted with cysteine. Position 435 is histidine. Position 433 can be substituted with arginine, proline, threonine, lysine, serine, alanine, methionine, or asparagine; in one embodiment, position 433 is histidine. Position 434 can be substituted with arginine, tryptophan, histidine, phenylalanine, tyrosine, serine, methionine or threonine. Position 436 can be substituted with leucine, arginine, isoleucine, lysine, methionine, valine, histidine, serine, or threonine. Optionally, the mutated His435 loop region contains a glutamic acid insertion at position 437*. In one embodiment, positions 432 and 437 are cysteine, position 433 is arginine, proline, threonine, lysine or histidine, position 434 is arginine, tryptophan, histidine, phenylalanine, or tyrosine, position 435 is histidine, and position 436 is leucine, arginine, isoleucine, lysine, methionine, valine or histidine (see, e.g., FIG. 4A). In one embodiment, the His435 loop region is CXRHXC (SEQ ID NO:11), where position 433 is arginine, histidine, asparagine, proline, or serine, and position 436 is arginine, isoleucine, methionine, or serine (see., e.g., FIG. 4B). In one embodiment, the His435 loop region is CRRHXC (SEQ ID NO:12) wherein position 436 is substituted with leucine, arginine, isoleucine, lysine, methionine, valine, histidine, serine, or threonine; for example, it can be substituted with leucine, isoleucine, serine or threonine. In one embodiment, the His435 loop region is CXRHRC (SEQ ID NO:13) wherein position 433 is arginine, proline, threonine, lysine, serine, alanine, methionine, or asparagine. Optionally, in any of these embodiments, the mutated His435 loop region contains a glutamic acid insertion at position 437*.

In another embodiment of the modified IgG constant domain, or FcRn-binding fragment thereof (e.g., an Fc region or hinge-Fc region), the His435 loop region of the CH3 domain of the Fc fragment has the amino acid sequence ZXXHXZ, wherein "Z" is glutamine, glutamic acid, histidine, or aspartic acid (residues 432-437; SEQ ID NO:14). In this embodiment, the amino acid identified by "Z" at position 432 can be the same as the amino acid identified by "Z" at position 437, or it can be different. Table 1 refers to this library of mutants as based on the amino acid sequence ZXXHXZ (SEQ ID NO:14).

Without intending to be bound by theory, it is postulated that the introduction of charged residues (e.g., glutamic acid, aspartic acid, histidine) into the His435 loop region, particularly at positions 432 and/or 437 (the Z residues in the ZXXHXZ motif; SEQ ID NO:14), may alter pH dependent recycling of IgG within a cell. In one embodiment, at least one of positions 432 or 437 is a substituted with a negatively charged residue, which may facilitate the formation of a salt bridge between a histidine at position 435 and the negatively charged residue at position 432 and/or 437. In one embodiment, one of residue 432 and 437 is substituted with a negatively charged residue and the other is substituted with a positively charged residue which may facilitate the formation of a salt bond between residue 432 and residue 437. In one embodiment, at least one of positions 432 or 437 is a substituted with a charged residue; for example, position 432 can be substituted with a charged residue, such as glutamic acid or histidine, and position 437 can be substituted with glutamine, glutamic acid, aspartic acid or histidine. In an illustrative embodiment, position 432 is substituted with a glutamic acid and position 437 is substituted with a glutamine. Additionally or alternatively, position 433 is substituted with arginine, alanine, lysine, threonine, leucine, serine, proline, or glutamine; in another embodiment; positions 433 is a histidine. Additionally or alternatively, position 434 is substituted with tyrosine, phenylalanine, histidine, serine or tryptophan. Additionally or alternatively, position 436 is substituted with an arginine, histidine, asparagine, lysine, leucine, methionine, threonine, or valine. In certain embodiments, position 432 is substituted with glutamic acid or histidine, position 433 is substituted with arginine, alanine, lysine, threonine or leucine; position 434 is substituted with phenylalanine or tyrosine, position 436 is substituted with arginine, histidine, asparagine or lysine, and position 437 is substituted with glutamine or glutamic acid (see, e.g., FIG. 4C). In one embodiment, positions 433 and/or 436 are substituted with a positively charged amino acid. Additionally or alternatively, position 434 is substituted with a hydrophobic amino acid.

In one embodiment, the mutated His435 loop region of the CH3 domain of the Fc fragment has a consensus sequence of: E(R/A)(W/S/F)HRQ (SEQ ID NO:15). Although it was postulated that the introduction of a salt bridge between positions 432 and 437 might (in comparison with the cystine at these positions) increase the flexibility of the His435 loop and lead to greater pH dependence (along with a longer in vivo half-life), it was surprisingly found that substitution with glutamine at position 437, rather than substitution with a charged amino acid, yielded the most consistent gains in pH dependence of binding of the modified IgG constant domain, or FcRn-binding fragment thereof (e.g., an Fc region or hinge-Fc region), to FcRn.

Table 1 shows a number of exemplary mutated amino acid sequences within the His435 loop region of the IgG1 Fc region. These modified IgG constant domains were evaluated in an anti-CD20 IgG, known as Hb20.3 (Table 1). Some of these modified IgG constant domains were further evaluated in a motavizumab (NuMax) IgG (Tables 2 and 3), and pharmacokinetic properties were evaluated in mice and/or cynomolgus as described in more detail in the Examples.

One exemplary embodiment of a modified IgG of the invention is referred to herein as "N3E-YTE," which contains the sequence Cys-Ser-Trp-His-Leu-Cys-Glu (CSWHLCE; SEQ ID NO:16) at positions 432-437* (with Glu being an insertion at position 437*, which is in between positions 437 and 478), incorporated into a "YTE" IgG1 constant domain base structure (IgG1 with Tyr252, Thr254 and Glu256). The histidine at position 435 is the only IgG1 wild-type residue in the His435 loop region in N3E-YTE. Both wild-type IgG1 and "YTE" (U.S. Pat. No. 7,083,784, issued Aug. 1, 2006; PCT publication WO 2002/060919, published Aug. 8, 2002) exhibit relatively low binding affinity for FcRn at pH 7.4, with YTE having significantly higher binding affinity for FcRn than wild type at pH 6.0 and a longer in vivo half-life (thus falling into quadrant I of the graph in FIG. 2B). N3E-YTE, on the other hand, which is found in quadrant III of the graph in FIG. 2B, exhibits high binding affinity for FcRn at both pH 6.0 and pH 7.4 (generally having lower pH dependence), and exhibits a short in vivo half-life in a human FcRn mouse model. N3E-YTE may therefore be well-suited for use in IgGs intended for use in removing or neutralizing toxic antigens, autoimmune therapies, or biological imaging applications. N3-YTE, which is identical to N3E-YTE except that it does not include the extra glutamic acid at position 437*, has similar pharmacokinetic properties to N3E-YTE and is likewise found in quadrant III in the coordinate plane shown in FIG. 2B. Modified IgGs of the invention which, like N3E-YTE and N3-YTE, are characterized by high binding affinity for FcRn at both pH 6.0 and pH 7.4 (generally those having lower pH dependence), and short in vivo half-lives, may optionally exhibit abdeg-like pharmacokinetic properties; they may possess the ability to promote endogenous IgG degradation, thereby ameliorating certain autoimmune diseases characterized by destructive antibodies.

Besides being useful for applications that require a short in vivo half-life, N3E-YTE and N3-YTE also serve as a convenient platform for the development of other IgG constant domains that retain high binding affinity for FcRn at pH 6.0 but exhibit lower levels of binding affinity at pH 7.4 and extended in vivo half-lives.

Thus in some embodiments of the modified IgG constant domain, or FcRn-binding fragment thereof (e.g., an Fc region or hinge-Fc region), the His435 loop region is similar to that of N3E-YTE or N3-YTE except that position 434 may be substituted with a different hydrophobic residue. Examples of His435 sequences that can be incorporated into the YTE base structure include Cys-Ser-Phe-His-Leu-Cys (CSFHLC; SEQ ID NO:17), Cys-Ser-Ile-His-Leu-Cys (CSIHLC; SEQ ID NO:18), Cys-Ser-Leu-His-Leu-Cys-Glu (CSLHLC; SEQ ID NO:19), with or without the glutamic acid insertion at position 437*. Without intending to be bound by theory, it has been observed that a hydrophobic residue at either or both of positions 434 and 436 may lead to a reduction in pH sensitivity, which may in turn reduce in vivo half-life.

Another exemplary embodiment of the modified IgG constant domain, or FcRn-binding fragment thereof (e.g., an Fc region or hinge-Fc region), is referred to herein as "N3," which contains the sequence Cys-Ser-Trp-His-Leu-Cys (CSWHLC; SEQ ID NO:20) at positions 432-437 (no insertion between positions 437 and 438), incorporated into a wild type IgG1 constant domain base structure, rather than the YTE base structure of N3E-YTE. Surprisingly, removing the mutant YTE base structure restored pH dependence of binding to FcRn, primarily by decreasing the binding affinity of this molecule to FcRn at pH 7.4, compared to N3E-YTE and N3-YTE. N3 exhibits a significantly longer in vivo half-life and slow clearance rates, comparable to those observed for YTE.

However, half-life extension is not the only clinically relevant outcome of modulating the Fc-FcRn interaction; retaining or enhancing, or at other times inhibiting, other biological activities such as effector function may also be important, depending on the intended therapeutic application. The YTE mutant exhibits reduced effector function (ADCC and opsonophagocytic killing) due to slightly reduced Fcγ (Fc gamma) receptor binding. A molecule with YTE-like pharmacokinetics, but enhanced effector function may be useful in for certain therapeutic applications. Surprisingly and advantageously, N3 exhibits additional (compared to YTE) biological properties of great interest, over and above the observed increase in serum half-life. For example, N3 remains fully capable of binding to Fc ligands such as FcγRIIa and C1q. Potentially, N3 may exhibit even better effector function than wild-type IgG1. N3 further exhibits full opsonophagocytic killing (OPK) activity and antibody-dependent cell mediated cytotoxicity (ADCC). More generally, N3 appears to exhibit pharmacological properties that are similar to or improved relative to wild-type IgG in experiments performed in HuFcRn mice and cynomolgus monkeys, while exhibiting a substantially longer in vivo half-life (see Example I). Thus, N3 may be a useful alternative to YTE in clinical settings where normal effector function is desirable, such as in anti-bacterial monoclonal antibodies that rely on opsonophagocytic killing for efficacy.

Several other exemplary embodiments of the modified IgG constant domain, or FcRn-binding fragment thereof (e.g., an Fc region or hinge-Fc region), incorporate a CXXHXC motif (SEQ ID NO:21) in the His435 loop region at residues 432-437 of IgG1, or a CXXHXCE motif (SEQ ID NO:22) at residues 432-437*, which motifs characterize N3E-YTE and N3-YTE, respectively. These embodiments generally exhibit greater pH dependence of binding affinity for FcRn, and/or longer in vivo half-lives, than N3E-YTE and N3-YTE, and typically fall within quadrant I in the graph shown in FIG. 2B. Increased pH dependence is generally manifested by reduced binding affinity for FcRn at pH 7.4 (i.e., a higher $KD_{pH7}$ for binding to FcRn) and a higher binding affinity for FcRn at pH 6.0 (i.e., a lower KD$_{pH6}$ for binding to FcRn). As noted above, the His435 loop region in N3E-YTE (Cys-Ser-Trp-His-Leu-Cys-Glu; SEQ ID NO:16) has hydrophobic substitutions at residues 434 (Trp) and 436 (Leu). In some embodiments exhibiting greater pH dependency, at least one of residues 433, 434 and 436 is substituted with a positively charged residue. Exemplary modified IgGs (e.g., IgG1) having a CXXHXCE motif (SEQ ID NO:22) at residues 432 to 437*, substituted with a positively charged residue at at least one of positions 433, 434 and 436 and incorporating a YTE base structure, are shown in Table 1 and include embodiments referred to herein as YC33-YTE, YC83-YTE, YC37-YTE, YC56-YTE and YC59-YTE. A motif for the His435 loop region at positions 432-437 is CXRHRC (SEQ ID NO:13), which like all motifs described herein can be incorporated into a wild-type base structure, a YTE base structure, or any other mutant IgG constant domain or FcRn-binding fragment thereof.

Other exemplary embodiments of the modified IgG constant domain, or FcRn-binding fragment thereof (e.g., an Fc region or hinge-Fc region), incorporate the ZXXHXZ (SEQ ID NO:14) motif and lack the cystine moiety that characterizes the CXXXXC(E) motif (SEQ ID NOs:9/10). One such embodiment (an e.g., IgG1) shown in Table 1 is referred to herein as Y31-YTE. Y31-YTE has a modified His435 loop at positions 432-437 having the sequence Glu-Arg-Phe-His-Arg-Gln (ERFHRQ; SEQ ID NO:25) and has an extended half-life compared to wild type IgG1. Other embodiments shown in Table 1 that exhibit increased pH dependency include Y3-YTE and Y12-YTE, characterized by modified His435 loops at positions 432-437 of Glu-Arg-Tyr-His-Thr-Gln (ERYHTQ; SEQ ID NO:26) and Glu-Ala-Trp-His-Arg-Gln (EAWHRQ; SEQ ID NO:27), respectively. Still other embodiments shown in Table 1 with increased pH dependency include Y37-YTE, Y9-YTE, and Y83-YTE, characterized by modified His435 loops at positions 432-437 of His-Arg-Phe-His-Leu-Gln (HRFHLQ; SEQ ID NO:28), Glu-Ala-Phe-His-Arg-Glu (EAFHRE; SEQ ID NO:29), and Glu-Pro-Tyr-His-Arg-Glu (EPYHRE; SEQ ID NO:37), respectively.

As described in detail in the Examples, below, some of the modified IgG constant domains that were evaluated in the anti-CD20 (HB20.3) IgG were further tested in motavizumab, in order to evaluate binding to FcRn in the context of a different variable domain. The modified IgG constant domains present in certain mutants based on the YTE IgG constant domain base structure, i.e., N3E-YTE, Y3-YTE, Y12-YTE, Y31-YTE, as well as certain mutants based on the wild-type IgG1 constant domain base structure, i.e., N3, Y12 and Y31, were tested in motavizumab. It was found that the binding affinity of the IgG constant domain toward FcRn at pH 6.0 binding was largely the same as in the anti-CD20 IgG. The effect of the "YTE" base structure was also tested in motavizumab. The pharmacokinetic properties of Mota-Y12-YTE and Mota-Y31-YTE were compared with those of Mota-Y12-WT and Mota Y31-WT, respectively (motavizumab providing the variable domain). Enhanced binding affinity toward FcRn at pH 6.0 and pH dependency of binding affinity was observed, suggesting that YTE and the H435 loop region both affect pH dependency binding to FcRn. Serum clearance rates in a mouse model using motavizumab were also evaluated. Most of the IgGs evaluated were cleared from serum relatively slowly, thereby suggesting enhanced recycling via FcRn binding. However, IgG having the N3E-YTE mutation, which has much reduced pH dependency in its binding affinity for FcRn, was quickly cleared from serum. For many therapeutic applications, reduced (slower) serum clearance is beneficial, however for some therapeutic applications and many diagnostic applications, faster clearance is preferred, as described in more detail elsewhere herein. These data suggest that the binding affinity of the IgG constant domain for FcRn at pH 7.4 may be an important determinant in serum half-lives and clearance rates for IgGs. Tight binding to FcRn at pH 7.4 (e.g., KD of 25 nM) for N3E-YTE was associated with fast serum clearance rates. However, as the KD at pH 7.4 decreased below 1 uM at pH 7.4, the IgG began to exhibit enhanced half-life and slower clearance rates.

Amino acid modifications can be made by any method known in the art and many such methods are well known and routine for the skilled artisan. For example, but not by way of limitation, amino acid substitutions, deletions and insertions may be accomplished using any well-known PCR-based technique. Amino acid substitutions may be made by site-directed mutagenesis (see, for example, Zoller and Smith, *Nucl. Acids Res.* 10:6487-6500, 1982; Kunkel, *Proc. Natl. Acad. Sci USA* 82:488, 1985, which are hereby incorporated by reference in their entireties). Mutants that result in increased affinity for FcRn and increased in vivo half-life may readily be screened using well-known and routine assays, such as those described herein. Amino acid substitutions can be introduced at one or more residues in the IgG constant domain or FcRn-binding fragment thereof (e.g., an Fc region or hinge-Fc region), and the mutated constant domains or fragments can be expressed on the surfaces of bacteriophage which are then screened for increased FcRn binding affinity.

Once generated, a mutated IgG constant domain, or fragment thereof (e.g., an Fc region or hinge-Fc region), may be used in the construction of an IgG (e.g., by fusing to the variable portions of an antibody of interest) or an Fc fusion molecule (e.g., by fusing/conjugating a heterologous moiety). A modified IgG or Fc fusion molecule of the invention may be generated by methods well known to one skilled in the art. Briefly, such methods include but are not limited to, combining a variable region with the desired specificity (e.g., a variable region isolated from a phage display or expression library or derived from a human or non-human antibody) with a modified IgG constant region, or an FcRn-binding fragment thereof (e.g., an Fc region or hinge-Fc region) having an altered half-life as provided herein. Alternatively, one skilled in the art may generate a modified IgG or Fc fusion molecule of the invention by substituting at least one amino acid residue in the Fc region of an antibody or Fc fusion molecule.

In addition to affecting half-life, the amino acid modifications described herein may alter (i.e., increase or decrease) the bioavailability (e.g., transport to mucosal surfaces, or other target tissues) of the molecules, in particular, alters (i.e., increases or decreases) transport (or concentration or half-life) of the molecule to mucosal surfaces (e.g., of the lungs) or other portions of a target tissue. In some embodiments, the amino acid modifications alter (e.g., increase or decrease) transport or concentration or half-life of the molecule to the lungs. In some embodiments, the amino acid modifications alter (e.g., increase or decrease) transport (or concentration or half-life) of the molecule to the heart, pancreas, liver, kidney, bladder, stomach, large or small intestine, respiratory tract, lymph nodes, nervous tissue (central and/or peripheral nervous tissue), muscle, epidermis, bone, cartilage, joints, blood vessels, bone marrow, prostate, ovary, uterine, tumor or cancer tissue, etc.

In some embodiments, the amino acid modifications do not abolish, or do not alter, one or more other immune effector or receptor binding functions of the constant domain, for example, but not limited to complement fixation, antibody-dependent cellular cytotoxicity (ADCC), complement dependent cytotoxicity (CDC), antibody dependent cellular phagocytosis (ADCP) and/or binding to one or more Fc gamma receptors such as FcγRI, FcγRII, and FcγRIII. Modified IgGs and other molecules of the invention can be evaluated for effector function using methods well-known and routine in the art.

In some embodiments, the modified FcRn binding fragment of the constant domain does not contain sequences that mediate immune effector functions or other receptor binding. Such fragments may be particularly useful for conjugation to a non-IgG or non-immunoglobulin molecule to increase the in vivo half-life thereof. In some embodiments, the effector functions are selectively altered (e.g., to reduce or increase effector functions).

More generally, the invention provides modified IgGs well-suited for a variety of diagnostic and therapeutic purposes. The invention provides modified IgGs exhibiting varying levels of pH dependence of their binding to FcRn. Different levels of pH dependence may result in or correlate with different pharmacokinetic properties, which in turn yield modified IgGs that are better suited for some purposes than for others.

For example, some of the modified IgGs described herein exhibit high affinity binding to FcRn at pH 6.0 along with a high level of pH dependence in their binding to FcRn, and an observed increase in in vivo half-life. Modified IgGs of this aspect of the invention have utility, for example, when employed as therapeutic agents in applications wherein a longer in vivo half-life is desirable. Optionally the modified IgG exhibits other improved pharmacokinetic properties as well, such as retained or enhanced ability to interact with Fc-ligands such as Fcγ receptors and C1q, robust opsonophagocytic killing (OPK) activity, and the ability to mediate Fc effector functions (e.g., CDC, ADCC).

In contrast, some of the modified IgGs described herein exhibit high affinity binding to FcRn at pH 6.0 along with a lower level of pH dependence in their binding to FcRn (typically as a result of enhanced affinity for FcRn at pH 7.4), and an observed decrease in in vivo half-life. Modified IgGs of this aspect of the invention have utility, for example, when employed as therapeutic agents in applications wherein a shorter in vivo half-life is desirable, such as in treating certain autoimmune conditions. They may also be well-suited to diagnostic applications, such as when used as a biological imaging agent, where quick clearance from bodily fluids or tissue is desired.

Another aspect of the invention is aimed at improving the effectiveness of therapeutic and diagnostic IgGs that have been engineered for pH-dependent binding to their antigen. Antibodies can be used to inactivate targets or antigens by binding to them with high affinity. The antibody-antigen complex is then cleared from circulation. Antibody-mediated clearance can be improved by engineering in pH-dependent antigen binding so that antigen is bound more tightly at higher pH (pH 7.4) and less tightly at lower pH (pH 6), allowing the antigen to be released and degraded in the acidic environment of the endosome.

Engineering in pH dependence of binding of the IgG constant domain to FcRn may be advantageous for immunoglobulins that naturally exhibit, or that have been engineered to exhibit, pH dependence for antigen binding. Immunoglobulins that have been engineered to more rapidly clear antigens from serum or tissue by means of alterations in the pH dependence of antigen binding to the antigen-binding site of the immunoglobulin, can be further improved by incorporating a pH binding modified IgG constant domain, or FcRn binding fragment thereof (e.g., an Fc region or hinge-Fc region) (e.g., the pH binding engineered Fc shown in quadrant I of FIGS. 2A and B) Without intending to be bound by theory, it is suggested that a modified IgG exhibiting pH-dependent antigen binding to the variable region, where binding to antigen at acidic pH (e.g., 6) is significantly reduced relative to the binding at neutral pH (e.g., 7.4), and a pH binding engineered Fc, where binding affinity for FcRn at both pH 7.4 and pH 6.0 are increased relative to the wild type IgG1, could clear antigen faster and in a more persistent manner compared to a wild type IgG1. The improved Fc and FcRn binding at the neutral pH enhance the presence of the antibody at the cell surface and resulting in antigen being bound to the IgG at the cell surface. Thus the antibody more efficiently pulls the antigens into the endosome; (FIG. 9B), where the binding affinity for the antigen is decreased, resulting faster release and degradation. The high affinity binding of Fc to FcRn at acidic pH leads to recycling of the antigen free IgG back to the cell surface or serum to bind and clear more antigen. This strategy combines pH-dependent IgG-antigen binding (variable region) with pH binding engineered IgG constant domain to FcRn. An example of a modified IgG of this aspect of the invention is an IgG that has been engineered for pH dependent binding of its antigen as well as having been engineered to include the N3E-YTE or the N3-YTE IgG constant (Table 1).

The modified immunoglobulin molecules of the invention include IgG molecules that naturally contain an FcRn binding domain, as well as other non-IgG immunoglobulins (e.g., IgE, IgM, IgD, IgA and IgY) or fragments of immunoglobulins that have been engineered to contain an FcRn-binding fragment (i.e., fusion proteins comprising non-IgG immunoglobulin or a fragment thereof and an FcRn binding domain, such as an Fc region or Fc hinge region). In both cases the FcRn-binding domain has one or more amino acid modifications that increase the affinity of the constant domain fragment for FcRn at pH 6.0 and, optionally, affect (either increase or decrease) the pH dependence of binding to FcRn.

Modified IgG constant domains of the invention were tested in various immunoglobulins, such as Hb20.3 anti-CD20 IgG and motavizumab, as described in more detail in the Examples. One of skill in the art will recognize that the modified IgG constant domain, or FcRn-binding fragment thereof (e.g., an Fc region or hinge-Fc region), of the invention can thus be readily incorporated into any immunoglobulin or other molecule in order to provide the modified immunoglobulin or other molecule with enhanced pharmacokinetic properties.

The modified immunoglobulins include any immunoglobulin molecule that binds (preferably, immunospecifically, i.e., competes off non-specific binding), as determined by immunoassays well known in the art for assaying specific antigen-antibody binding) an antigen and contains an FcRn-binding fragment. Such antibodies include, but are not limited to, polyclonal, monoclonal, bi-specific, multi-specific, human, humanized, chimeric antibodies, single chain antibodies, Fab fragments, F(ab')$_2$ fragments, disulfide-linked Fvs, and fragments containing either a VL or VH domain or even a complementary determining region (CDR) that specifically binds an antigen, in certain cases, engineered to contain or fused to an FcRn binding domain.

The IgG molecules of the invention, and FcRn-binding fragments thereof, are in certain embodiments, IgG1 subclass of IgGs, but may also be any other IgG subclasses of given animals. For example, in humans, the IgG class includes IgG1, IgG2, IgG3, and IgG4. In embodiments of the invention based on human IgG3, it should be noted that the amino acid sequence of the His435 loop region (positions 432-437) of human IgG3 is not fully conserved with respect to human IgG1, IgG2, and IgG4, having nonconserved residues at positions 435 and 436 of arginine(R) and phenylalanine (F), respectively (LHNRFT; SEQ ID NO:7, FIG. 1D) and further, is known to exhibit allelic variation at positions 435 and 436 (FIG. 1D, asterisks). In view of the known variations, one of skill in the art will recognize it may be advantageous to substitute histidine at position 435 (R435H) and/or tyrosine at position 436 (F436Y) in the CH3 domain of IgG3 in the molecules of the invention.

The immunoglobulins (and other proteins used herein) may be from any animal origin including birds and mammals. The antibodies can be, for example, human, rodent (e.g., mouse and rat), donkey, sheep, rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example, in U.S. Pat. No. 5,939,598 by Kucherlapati et al.

The antibodies of the present invention may be monospecific, bispecific, trispecific or of greater multispecificity. Multispecific antibodies may be specific for different epitopes of a polypeptide or may be specific for heterologous epitopes, such as a heterologous polypeptide or solid support material. See, e.g., PCT publications WO 93/17715; WO 92/08802; WO 91/00360; WO 92/05793; Tutt, et al., *J. Immunol.*, 147:60-69, 1991; U.S. Pat. Nos. 4,474,893; 4,714,681; 4,925,648; 5,573,920; 5,601,819; Kostelny et al., *J. Immunol.*, 148:1547-1553, 1992.

The antibodies of the invention include derivatives that are otherwise modified, i.e., by the covalent attachment of any type of molecule to the antibody such that covalent attachment does not prevent the antibody from binding antigen and/or generating an anti-idiotypic response. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to, specific chemical cleavage, acetylation, formylation, metabolic synthesis of tunicamycin, etc. Additionally, the derivative may contain one or more non-classical amino acids.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas, pp. 563-681 (Elsevier, N.Y., 1981); Goding, *Monoclonal Antibodies: Principles and Practice*, pp. 59-103 (Academic Press, 1986); Kozbor, *J. Immunol.*, 133:3001 (1984); and Brodeur et al., *Monoclonal Antibody Production Techniques and Applications*, pp. 51-63 (Marcel Dekker, Inc., New York, 1987) (all of which are incorporated herein by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. In a non-limiting example, mice can be immunized with an antigen of interest or a cell expressing such an antigen. Once an immune response is detected, e.g., antibodies specific for the antigen are detected in the mouse serum, the mouse spleen is harvested and splenocytes isolated. The splenocytes are then fused by well-known techniques to any suitable myeloma cells. Hybridomas are selected and cloned by limiting dilution. The hybridoma clones are then assayed by methods known in the art for cells that secrete antibodies capable of binding the antigen. Ascites fluid, which generally contains high levels of antibodies, can be generated by inoculating mice intraperitoneally with positive hybridoma clones.

Antibody fragments which recognize specific epitopes may be generated by known techniques. For example, Fab and F(ab')$_2$ fragments may be produced by proteolytic cleavage of immunoglobulin molecules, using enzymes such as papain (to produce Fab fragments) or pepsin (to produce F(ab')$_2$ fragments). F(ab')$_2$ fragments contain the complete light chain, and the variable region, the CH1 region and the hinge region of the heavy chain.

For example, antibodies can also be generated using various phage display methods known in the art. In phage display methods, functional antibody domains are displayed on the surface of phage particles which carry the polynucleotide sequences encoding them. In a particular embodiment, such phage can be utilized to display antigen binding domains, such as Fab and Fv or disulfide-bond stabilized Fv, expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage, including fd and M13. The antigen binding domains are expressed as a recombinantly fused protein to either the phage gene III or gene VIII protein. Alternatively, the modified FcRn binding portion of immunoglobulins of the present invention can be also expressed in a phage display system.

Methods for producing monoclonal antibodies using antibody phage libraries are routine and well known in the art. See e.g., McCafferty et al., *Nature,* 348:552-554 (1990); and Clackson et al., *Nature,* 352:624-628 (1991) and Marks et al., *J. Mol. Biol.,* 222:581-597 (1991). In addition to commercially available kits for generating phage display libraries (e.g., the Pharmacia Recombinant Phage Antibody System, catalog no. 27-9400-01; and the Stratagene SURFZAP™ phage display kit, catalog no. 240612), examples of methods and reagents for use in generating and screening antibody display libraries can be found in, for example, U.S. Pat. Nos. 6,248,516; 6,545,142; 6,291,158; 6,291,1591; 6,291,160; 6,291,161; 6,680,192; 5,969,108; 6,172,197; 6,806,079; 5,885,793; 6,521,404; 6,544,731; 6,555,313; 6,593,081; 6,582,915; 7,195,866. Additional examples of phage display methods that can be used to make the immunoglobulins, or fragments thereof, of the present invention include those disclosed in Brinkman et al., *J.*

Immunol. Methods, 182:41-50, 1995; Ames et al., J. Immunol. Methods, 184:177-186, 1995; Kettleborough et al., Eur. J. Immunol., 24:952-958, 1994; Persic et al., Gene, 187:9-18, 1997; Burton et al., Advances in Immunology, 57:191-280, 1994; PCT application No. PCT/GB91/01134; PCT publications WO 90/02809; WO 91/10737; WO 92/01047; WO 92/18619; WO 93/1 1236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired fragments, and expressed in any desired host, including mammalian cells, insect cells, plant cells, yeast, and bacteria, e.g., as described in detail below. For example, techniques to recombinantly produce Fab, Fab' and $F(ab')_2$ fragments can also be employed using methods known in the art such as those disclosed in PCT publication WO 92/22324; Mullinax et al., BioTechniques, 12(6):864-869, 1992; and Sawai et al., AJRI, 34:26-34, 1995; and Better et al., Science, 240:1041-1043, 1988 (each of which is incorporated by reference in its entirety). Examples of techniques which can be used to produce single-chain Fvs and antibodies include those described in U.S. Pat. Nos. 4,946,778 and 5,258,498; Huston et al., Methods in Enzymology, 203:46-88, 1991; Shu et al., PNAS, 90:7995-7999, 1993; and Skerra et al., Science, 240:1038-1040, 1988.

For some uses, including in vivo use of antibodies in humans and in vitro detection assays, it may be useful to use chimeric, humanized, or human antibodies. A chimeric antibody is a molecule in which different portions of the antibody are derived from different animal species, such as antibodies having a variable region derived from a murine monoclonal antibody and a constant region derived from a human immunoglobulin. Methods for producing chimeric antibodies are known in the art. See e.g., Morrison, Science, 229:1202, 1985; Oi et al., BioTechniques, 4:214 1986; Gillies et al., J Immunol. Methods, 125:191-202, 1989; U.S. Pat. Nos. 5,807,715; 4,816,567; and 4,816,397, which are incorporated herein by reference in their entireties. Humanized antibodies are antibody molecules from non-human species that bind the desired antigen having one or more complementarity determining regions (CDRs) from the non-human species and framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. See, e.g., Queen et al., U.S. Pat. No. 5,585,089; Riechmann et al., Nature, 332:323, 1988, which are incorporated herein by reference in their entireties. Antibodies can be humanized using a variety of techniques known in the art including, for example, CDR-grafting (EP 239,400; PCT publication WO 91/09967; U.S. Pat. Nos. 5,225,539; 5,530,101 and 5,585,089), veneering or resurfacing (EP 592,106; EP 519,596; Padlan, Molecular Immunology, 28(4/5):489-498, 1991; Studnicka et al., Protein Engineering, 7(6):805-814, 1994; Roguska et al., Proc Natl. Acad. Sci. USA, 91:969-973, 1994), and chain shuffling (U.S. Pat. No. 5,565,332), all of which are hereby incorporated by reference in their entireties. Humanization can be performed following the method of Winter and co-workers (Jones et al., Nature, 321:522-525 (1986); Reichmann et al., Supra; Verhoeyen et al., Science, 239:1534-1536 (1988)), by substituting hypervariable region sequences for the corresponding sequences of a human antibody. Specifically, humanized antibodies may be prepared by methods well known in the art including CDR grafting approaches (see, e.g., U.S. Pat. No. 6,548,640), veneering or resurfacing (U.S. Pat. Nos. 5,639,641 and 6,797,492; Studnicka et al., Protein Engineering 7(6):805-814 (1994); Roguska. et al., PNAS 91:969-973 (1994)), chain shuffling strategies (see e.g., U.S. Pat. No. 5,565,332; Rader et al., Proc. Natl. Acad. Sci. USA (1998) 95:8910-8915), molecular modeling strategies (U.S. Pat. No. 5,639,641), and the like. These general approaches may be combined with standard mutagenesis and recombinant synthesis techniques to produce monomeric humanized antibodies with desired properties.

Completely human antibodies are particularly desirable for therapeutic treatment of human patients. Human antibodies can be made by a variety of methods known in the art including phage display methods described above using antibody libraries derived from human immunoglobulin sequences. See U.S. Pat. Nos. 4,444,887 and 4,716,111; and PCT publications WO 98/46645; WO 98/50433; WO 98/24893; WO 98/16654; WO 96/34096; WO 96/33735; and WO 91/10741, each of which is incorporated herein by reference in its entirety.

Human antibodies can also be produced using transgenic mice which are incapable of expressing functional endogenous immunoglobulins, but which can express human immunoglobulin genes. For an overview of this technology for producing human antibodies, see Lonberg and Huszar, Int. Rev. Immunol., 13:65-93, 1995. For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entireties. See also Jakobovits et al., Proc. Natl. Acad. Sci. USA, 90:2551 (1993); Jakobovits et al., Nature, 362:255-258 (1993); Bruggemann et al., Year in Immuno., 7:33 (1993); U.S. Pat. Nos. 5,545,806, 5,569,825, 5,591,669 (all of GenPharm); U.S. Pat. No. 5,545,807; and WO 97/17852. The use of XENOMOUSE® strains of mice for production of human antibodies has been described. See Mendez et al. Nature Genetics 15:146-156 (1997) and Green and Jakobovits J. Exp. Med. 188:483-495 (1998). The XENOMOUSE® strains are available from Amgen, Inc. (Fremont, Calif.). The production of the XENOMOUSE® strains of mice and antibodies produced in those mice is further discussed in U.S. Pat. Nos. 6,673,986; 7,049,426; 6,833,268; 6,162,963, 6,150,584, 6,114,598, 6,075,181, 6,657,103; 6,713,610 and 5,939,598; US Publication Nos. 2004/0010810; 2003/0229905; 2004/0093622; 2005/0054055; 2005/0076395; and 2006/0040363. In an alternative approach, others, including GenPharm International, Inc., have utilized a "minilocus" approach. This approach is described in U.S. Pat. Nos. 5,545,807; 5,545,806; 5,625,825; 5,625,126; 5,633,425; 5,661,016; 5,770,429; 5,789,650; 5,814,318; 5,877,397; 5,874,299; 6,255,458; 5,591,669; 6,023,010; 5,612,205; 5,721,367; 5,789,215; 5,643,763; and 5,981,175. Kirin has also demonstrated the generation of human antibodies from mice in which large pieces of chromosomes, or entire chromosomes, have been introduced through microcell fusion. See U.S. Pat. No. 6,632,976. Additionally, KM™ mice, which are the result of cross-breeding of Kirin's Tc mice with Medarex's minilocus (Humab) mice, have been generated. These mice possess the human IgH transchromosome of the Kirin mice and the kappa chain transgene of the Genpharm mice (Ishida et al., Cloning Stem Cells, (2002) 4:91-102). Human antibodies can also be derived by in vitro methods. Suitable examples include but are not limited to phage display (MedImmune (formerly CAT), Morphosys, Dyax, Biosite/Medarex, Xoma, Symphogen, Alexion (formerly Proliferon), Affimed) ribosome display (MedImmune (formerly CAT)), yeast display, and the like. Phage display technology (See e.g., U.S. Pat. No. 5,969,108) can be used to produce human antibodies and antibody fragments in vitro, from immunoglobulin variable (V) domain gene repertoires from unimmunized donors. Phage display can be performed in a variety of formats, reviewed in, e.g., Johnson, Kevin S. and Chiswell, David J., *Current Opinion in Structural Biology* 3:564-571 (1993). Several sources of V-gene segments can be used for phage display. See e.g., Clackson et al., *Nature,* 352:624-628 (1991); Marks et al., *J. Mol. Biol.* 222:581-597 (1991); Griffith et al., *EMBO J.* 12:725-734 (1993); and U.S. Pat. Nos. 5,565,332 and 5,573,905. As discussed above, human antibodies may also be generated by in vitro activated B cells (see U.S. Pat. Nos. 5,567,610 and 5,229,275). In addition, companies such as Abgenix, Inc. (Freemont, Calif.), Medarex (NJ) and Genpharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., *Bio/Technology,* 12:899-903, 1988).

In particular embodiments, the modified antibodies have in vivo therapeutic and/or prophylactic uses. Examples of therapeutic and prophylactic antibodies which may be so modified include, but are not limited to, SYNAGIS® (MedImmune, MD) which is a humanized anti-respiratory syncytial virus (RSV) monoclonal antibody for the treatment of patients with RSV infection; HERCEPTIN® (Trastuzumab) (Genentech, CA) which is a humanized anti-HER2 monoclonal antibody for the treatment of patients with metastatic breast cancer; REMICADE® (infliximab) (Centocor, PA) which is a chimeric anti-TNFα monoclonal antibody for the treatment of patients with Crone's disease; REOPRO® (abciximab) (Centocor) which is an anti-glycoprotein IIb/IIIa receptor on the platelets for the prevention of clot formation; ZENAPAX® (daclizumab) (Roche Pharmaceuticals, Switzerland) which is an immunosuppressive, humanized anti-CD25 monoclonal antibody for the prevention of acute renal allograft rejection. Other examples are a humanized anti-CD18 F(ab')$_2$ (Genentech); CDP860 which is a humanized anti-CD18 F(ab')$_2$ (Celltech, UK); PRO542 which is an anti-HIV gp120 antibody fused with CD4 (Progenics/Genzyme Transgenics); Ostavir which is a human anti Hepatitis B virus antibody (Protein Design Lab/Novartis); PROTOVIR™ which is a humanized anti-CMV IgG1 antibody (Protein Design Lab/Novartis); MAK-195 (SEGARD) which is a murine anti-TNF-α F(ab')$_2$ (Knoll Pharma/BASF); IC14 which is an anti-CD14 antibody (ICOS Pharm); a humanized anti-VEGF IgG1 antibody (Genentech); OVAREX™ which is a murine anti-CA 125 antibody (Altarex); PANOREX™ which is a murine anti-17-IA cell surface antigen IgG2a antibody (Glaxo Wellcome/Centocor); BEC2 which is a murine anti-idiotype (GD3 epitope) IgG antibody (ImClone System); IMC-C225 which is a chimeric anti-EGFR IgG antibody (ImClone System); VITAXIN™ which is a humanized anti-αVβ3 integrin antibody (Applied Molecular Evolution/MedImmune); Campath 1H/LDP-03 which is a humanized anti CD52 IgG1 antibody (Leukosite); Smart M195 which is a humanized anti-CD33 IgG antibody (Protein Design Lab/Kanebo); RITUXAN™ which is a chimeric anti-CD20 IgG1 antibody (DEC Pharm/Genentech, Roche/Zettyaku); LYMPHOCIDE™ which is a humanized anti-CD22 IgG antibody (Immunomedics); Smart ID10 which is a humanized anti-HLA antibody (Protein Design Lab); ONCOLYM™ (Lym-1) is a radiolabelled murine anti-HLA DIAGNOSTIC REAGENT antibody (Techniclone); ABX-IL8 is a human anti-IL8 antibody (Abgenix); anti-CD11a is a humanized IgG1 antibody (Genetech/Xoma); ICM3 is a humanized anti-ICAM3 antibody (ICOS Pharm); IDEC-114 is a primatized anti-CD80 antibody (IDEC Pharm/Mitsubishi); ZEVALIN™ is a radiolabelled murine anti-CD20 antibody (IDEC/Schering AG); IDEC-131 is a humanized anti-CD40L antibody (IDEC/Eisai); IDEC-151 is a primatized anti-CD4 antibody (IDEC); IDEC-152 is a primatized anti-CD23 antibody (IDEC/Seikagaku); SMART anti-CD3 is a humanized anti-CD3 IgG (Protein Design Lab); 5G1.1 is a humanized anti-complement factor 5 (C5) antibody (Alexion Pharm); D2E7 is a humanized anti-TNF-α antibody (CAT/BASF); CDP870 is a humanized anti-TNF-α Fab fragment (Celltech); IDEC-151 is a primatized anti-CD4 IgG1 antibody (DEC Pharm/SmithKline Beecham); MDX-CD4 is a human anti-CD4 IgG antibody (Medarex/Eisai/Genmab); CDP571 is a humanized anti-TNF-α IgG4 antibody (Celltech); LDP-02 is a humanized anti-α4β7 antibody (LeukoSite/Genentech); OrthoClone OKT4A is a humanized anti-CD4 IgG antibody (Ortho Biotech); ANTOVA™ is a humanized anti-CD40L IgG antibody (Biogen); ANTEGREN™ is a humanized anti-VLA-4 IgG antibody (Elan); MDX-33 is a human anti-CD64 (FcγR) antibody (Medarex/Centeon); SCH55700 is a humanized anti-IL-5 IgG4 antibody (Celltech/Schering); SB-240563 and SB-240683 are humanized anti-IL-5 and IL-4 antibodies, respectively, (SmithKline Beecham); rhuMab-E25 is a humanized anti-IgE IgG1 antibody (Genentech/Norvartis/Tanox Biosystems); IDEC-152 is a primatized anti-CD23 antibody (IDEC Pharm); ABX-CBL is a murine anti CD-147 IgM antibody (Abgenix); BTI-322 is a rat anti-CD2 IgG antibody (Medimmune/Bio Transplant); Orthoclone/OKT3 is a murine anti-CD3 IgG2a antibody (ortho Biotech); SIMULECT™ is a chimeric anti-CD25 IgG1 antibody (Novartis Pharm); LDP-01 is a humanized anti-β$_2$-integrin IgG antibody (LeukoSite); Anti-LFA-1 is a murine anti CD18 F(ab')$_2$ (Pasteur-Merieux/Immunotech); CAT-152 is a human anti-TGF-β$_2$ antibody (Cambridge Ab Tech); vitaxin an anti-αvβ3 antibody; and Corsevin M is a chimeric anti-Factor VII antibody (Centocor).

Modified IgGs of the present invention may also include IgGs whose bioactive sites, such as antigen-binding sites, Fc-receptor binding sites, or complement-binding sites, are modified by genetic engineering to increase or reduce such activities compared to the wild type.

The present invention also provides fusion proteins comprising a bioactive molecule and a modified IgG constant domain, or an FcRn-binding fragment thereof (e.g., an Fc region or hinge-Fc region), having one or more modifications (i.e., substitutions, deletions, or insertions) in or near amino acid residues in the His435 region (residues 432-437) as identified herein. The bioactive molecule can be recombinantly fused or chemically conjugated (including both covalent and non-covalent conjugations) to the modified IgG constant domain or FcRn-binding fragment thereof. Optionally, the modified IgG constant domain or FcRn-binding fragment thereof may contain additional modification, such as modifications in the CH2 domain at one or more of amino acid residues 251-256, 285-290, and/or amino acid residues 308-314, and/or modifications in the CH3 domain at one or more of amino acid residues 385-389 and/or 428-431. The fusion of a bioactive molecule to a constant domain or a fragment thereof with one or more of such modifications increases the in vivo half-life of the bioactive molecule.

A bioactive molecule can be any polypeptide or synthetic drug known to one of skill in the art. In an illustrative embodiment, a bioactive molecule is a polypeptide consisting of at least 5, at least 10, at least 20, at least 30, at least 40, at least 50, at least 60, at least 70, at least 80, at least 90 or at least 100 amino acid residues. Examples of bioactive polypeptides include, but are not limited to, various types of antibodies, cytokines (e.g., IL-2, IL-3, IL-4, IL-5, IL-6, IL-7, IL-10, IL-12, IL-15, IFN-γ, IFN-α, and IFN-β), cell adhesion molecules (e.g., CTLA4, CD2, and CD28), ligands (e.g., TNF-α, TNF-β, and an anti-angiogenic factor such as endostatin), receptors, antibodies and growth factors (e.g., PDGF, EGF, NGF, and KGF). A bioactive molecule can also be a therapeutic moiety such as a cytotoxin (e.g., a cytostatic or cytocidal agent), a therapeutic agent or a radioactive element (e.g., alpha-emitters, gamma-emitters, etc.). Examples of cytostatic or cytocidal agents include, but are not limited to, paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

In some aspects members (receptor or ligand) of the TNF superfamily, as well as subunits, domains, motifs and epitopes of proteins belonging to this family of proteins are bound by modified IgGs of the present invention or fused to a modified IgG constant region, or an FcRn-binding fragment (e.g., an Fc region or hinge-Fc region) thereof. The TNF superfamily comprises numerous molecules including, but are not limited to Tumor Necrosis Factor-alpha ("TNF-alpha"), Tumor Necrosis Factor-beta ("TNF-beta"), Lymphotoxin-alpha ("LT-alpha"), CD30 ligand, CD27 ligand, CD40 ligand, 4-1 BB ligand, Apo-1 ligand (also referred to as Fas ligand or CD95 ligand), Apo-2 ligand (also referred to as TRAIL), Apo-3 ligand (also referred to as TWEAK), osteoprotegerin (OPG), APRIL, RANK ligand (also referred to as TRANCE), TALL-1 (also referred to as BlyS, BAFF or THANK), DR4, DR5 (also known as Apo-2, TRAIL-R2, TR6, Tango-63, hAP08, TRICK2, or KILLER), DR6, DcR1, DcR2, DcR3 (also known as TR6 or M68), CAR1, HVEM (also known as ATAR or TR2), GITR, ZTNFR-5, NTR-1, TNFL1, CD30, LTBr, 4-1BB receptor and TR9.

Additional examples of polypeptides which may be bound by modified IgGs of the present invention or fused to a modified IgG constant region, or an FcRn-binding fragment thereof (e.g., an Fc region or hinge-Fc region) include, but are not limited to: 5T4, ABL, ABCF1, ACVR1, ACVR1B, ACVR2, ACVR2B, ACVRL1, ADORA2A, Aggrecan, AGR2, AICDA, AIF1, AIGI, AKAP1, AKAP2, AMH, AMHR2, ANGPT1, ANGPT2, ANGPTL3, ANGPTL4, ANPEP, APC, APOC1, AR, aromatase, ATX, AX1, AZGP1 (zinc-a-glycoprotein), B7.1, B7.2, B7-H1, BAD, BAFF, BAG1, BAI1, BCR, BCL2, BCL6, BDNF, BLNK, BLR1 (MDR15), BlyS, BMP1, BMP2, BMP3B (GDFIO), BMP4, BMP6, BMP8, BMPR1A, BMPR1B, BMPR2, BPAG1 (plectin), BRCA1, C19orflO (IL27w), C3, C4A, C5, C5R1, CANT1, CASP1, CASP4, CAV1, CCBP2 (D6/JAB61), CCL1 (1-309), CCLI1 (eotaxin), CCL13 (MCP-4), CCL15 (MIP-Id), CCL16 (mcc-4), CCL17 (TARC), CCL18 (PARC), CCL19 (MIP-3b), CCL2 (MCP-1), MCAF, CCL20 (MIP-3a), CCL21 (MEP-2), SLC, exodus-2, CCL22(MDC/STC-), CCL23 (MPIF-I), CCL24 (MPIF-2/eotaxin-2), CCL25 (TECK), CCL26(eotaxin-3), CCL27 (CTACK/ILC), CCL28, CCL3 (MIP-1a), CCL4 (MIPIb), CCL5(RANTES), CCL7 (MCP-3), CCL8 (mcp-2), CCNA1, CCNA2, CCND1, CCNE1, CCNE2, CCRI (CKR1/HM145), CCR2 (mcp-IRB/RA), CCR3 (CKR3/CMKBR3), CCR4, CCR5(CMKBR5/ChemR13), CCR6 (CMKBR6/CKR-L3/STRL22/DRY6), CCR7 (CKR7/EBI1), CCR8 (CMKBR8/TERI/CKR-L1), CCR9 (GPR-9-6), CCRL1 (VSHK1), CCRL2 (L-CCR),CD164, CD19, CDIC, CD20, CD200, CD22, CD24, CD28, CD3, CD33, CD35, CD37, CD38, CD3E, CD3G, CD3Z, CD4, CD40, CD40L, CD44, CD45RB, CD52, CD69, CD72, CD74, CD79A, CD79B, CD8, CD80, CD81, CD83, CD86, CD137, CDH1 (Ecadherin), CDH10, CDH12, CDH13, CDH18, CDH19, CDH20, CDH5, CDH7, CDH8, CDH9, CDK2, CDK3, CDK4, CDK5, CDK6, CDK7, CDK9, CDKN1A (p21Wap1/Cip1),CDKN1B (p27Kip1), CDKNIC, CDKN2A (p161NK4a), CDKN2B, CDKN2C, CDKN3, CEBPB, CERI, CHGA, CHGB, Chitinase, CHST10, CKLFSF2, CKLFSF3, CKLFSF4, CKLFSF5, CKLFSF6, CKLFSF7, CKLFSF8, CLDN3, CLDN7 (claudin-7), CLN3, CLU (clusterin), CMKLR1, CMKOR1 (RDC1), CNR1, COL18A1, COLIA1, COL4A3, COL6A1, CR2, Cripto, CRP, CSF1 (M-CSF), CSF2 (GM-CSF), CSF3 (GCSF), CTLA4, CTL8, CTNNB1 (b-catenin), CTSB (cathepsin B), CX3CL1 (SCYD1), CX3CR1 (V28), CXCL1 (GRO1), CXCL10 (IP-IO), CXCLI1 (I-TAC/IP-9), CXCL12 (SDF1), CXCL13, CXCL14, CXCL16, CXCL2 (GRO2), CXCL3 (GRO3), CXCL5 (ENA-78/LIX), CXCL6 (GCP-2), CXCL9 (MIG), CXCR3 (GPR9/CKR-L2), CXCR4, CXCR6 (TYM-STR/STRL33/Bonzo), CYB5, CYCl, CYSLTR1, DAB21P, DES, DKFZp451J0118, DNCL1, DPP4, E2F1, Engel, Edge, Fennel, EFNA3, EFNB2, EGF, EGFR, ELAC2, ENG, Enola, ENO2, ENO3, EPHA1, EPHA2, EPHA3, EPHA4, EPHA5, EPHA6, EPHA7, EPHA8, EPHA9, EPHA10, EPHB1, EPHB2, EPHB3, EPHB4, EPHB5, EPHB6, EPHRIN-A1, EPHRIN-A2, EPHRINA3, EPHRIN-A4, EPHRIN-A5, EPHRIN-A6, EPHRIN-B1, EPHRIN-B2, EPHRIN-B3, EPHB4, EPG, ERBB2 (Her-2), EREG, ERK8, Estrogen receptor, Earl, ESR2, F3 (TF), FADD, farnesyl-transferase, FasL, FASNf, FCER1A, FCER2, FCGR3A, FGF, FGF1 (aFGF), FGF10, FGF11, FGF12, FGF12B, FGF13, FGF14, FGF16, FGF17, FGF18, FGF19, FGF2 (bFGF), FGF20, FGF21, FGF22, FGF23, FGF3 (int-2), FGF4 (HST), FGF5, FGF6 (HST-2), FGF7 (KGF), FGF8, FGF9, FGFR3, FIGF (VEGFD), FILI(EPSILON), FBL1 (ZETA), FLJ12584, FLJ25530, FLRT1 (fibronectin), FLT1, FLT-3, FOS, FOSLI(FRA-1), FY (DARC), GABRP (GABAa), GAGEB1, GAGEC1, GALNAC4S-6ST, GATA3, GD2, GDF5, GFI1, GGT1, GM-CSF, GNAS1, GNRH1, GPR2 (CCR10), GPR31, GPR44, GPR81 (FKSG80), GRCC10 (C10), GRP, GSN (Gelsolin), GSTP1, HAVCR2, HDAC, HDAC4, HDAC5, HDAC7A, HDAC9, Hedgehog, HGF, HIF1A, HIP1, histamine and histamine receptors, HLA-A, HLA-DRA, HM74, HMOXl, HSP90, HUMCYT2A, ICEBERG, ICOSL, ID2, IFN-a, IFNA1, IFNA2, IFNA4,1FNA5, EFNA6, BFNA7, IFNB1, IFN-gamma, IFNW1, IGBP1, IGF1, IGFIR, IGF2, IGFBP2, 1GFBP3, IGFBP6, DL-1, ILIO, ILIORA, ILIORB, IL-1, IL1R1 (CD121a), IL1R2(CD121b), ILIRA, IL-2, IL2RA (CD25), IL2RB(CD122), IL2RG(CD132), IL-4, IL-4R (CD123), IL-5, IL5RA(CD125), IL3RB(CD131), IL-6, IL6RA, (CD126), IR6RB(CD130), IL-7, IL7RA(CD127), IL-8, CXCR1 (ILIRA), CXCR2, (IL8RB/CD128), IL-9, IL9R (CD129), IL-10, IL10RA(CD210), IL10RB (CDW210B), IL-11, IL11RA, IL-12, IL-12A, IL-12B, IL-12RB1, IL-12RB2, IL-13, IL13RA1, IL13RA2, IL14, IL15, IL15RA, 1L16, IL17, IL17A, IL17B, IL17C, IL17R, IL18, IL18BP, IL18R1, IL18RAP, IL19, ILIA, ILIB, IL1F10, IL1F5, IL1F6, IL1F7, IL1F8, DL1F9, ILIHYI, ILIR1, IL1R2, ILIRAP, ILIRAPLI, IL1RAPL2, IL1RL1, IL1 RL2, ILIRN, IL2, IL20, IL20RA, IL21 R, IL22, IL22R, IL22RA2, IL23, DL24, IL25, IL26, IL27, IL28A, IL28B, IL29, IL2RA, IL2RB, IL2RG, IL3, IL30, IL3RA, IL4,1L4R, IL6ST (glycoprotein 130), ILK, INHA, INHBA, INSL3, INSL4, IRAK1, IRAK2, ITGA1, ITGA2,1TGA3, ITGA6 (a6 integrin), ITGAV, ITGB3, ITGB4 (134 integrin), JAG1, JAK1, JAK3, JTB, JUN, K6HF, KAI1, KDR, KITLG, KLFS (GC Box BP), KLF6, KLK10, KLK12, KLK13, KLK14, KLK15, KLK3, KLK4, KLK5, KLK6, KLK9, KRT1, KRT19 (Keratin 19), KRT2A, KRTHB6 (hair-specific type II keratin), LAMA5, LEP (leptin), Lingo-p75, Lingo-Troy, LPS, LTA (TNF-b), LTB, LTB4R (GPR16), LTB4R2, LTBR, MACMARCKS, MAG or Omgp, MAP2K7 (c-Jun), MCP-1, MDK, MIB1, midkine, MIF, MISRII, MJP-2,MK, MKI67 (Ki-67), MMP2, MMP9, MS4A1, MSMB, MT3 (metallothionectin-UI), mTOR, MTSS1, MUC1 (mucin), MYC, MYD88, NCK2, neurocan, NFKBI, NFKB2, NGFB (NGF), NGFR, NgR-Lingo, NgRNogo66, (Nogo), NgR-p75, NgR-Troy, NMEI (NM23A), NOTCH, NOTCH1, NOXS, NPPB, NROB1, NROB2, NRID1, NR1D2, NR1H2, NR1H3, NR1H4, NR112, NR113, NR2C1, NR2C2, NR2E1, NR2E3, NR2F1, NR2F2, NR2F6, NR3C1, NR3C2, NR4A1, NR4A2, NR4A3, NR5A1, NR5A2, NR6A1, NRP1, NRP2, NT5E, NTN4, ODZ1, OPRDI, P2RX7, PAP, PART1, PATE, PAWR, PCA3, PCDGF, PCNA, PDGFA, PDGFB, PDGFRA, PDG-FRB, PECAMI, peg-asparaginase, PF4 (CXCL4), PGF, PGR, phosphacan, PIAS2, PI3 Kinase, PIK3CG, PLAU (uPA), PLG, PLXDCI, PKC, PKC-beta, PPBP (CXCL7), PPID, PR1, PRKCQ, PRKD1, PRL, PROC, PROK2, PSAP, PSCA, PTAFR, PTEN, PTGS2 (COX-2), PTN, RAC2 (P21Rac2), RANK, RANK ligand, RARB, RGS1, RGS13, RGS3, RNFI10 (ZNF144), Ron, ROBO2, RXR, S100A2, SCGB 1D2 (lipophilin B), SCGB2A1 (mammaglobin 2), SCGB2A2 (mammaglobin 1), SCYE1 (endothelial Monocyte activating cytokine), SDF2,SERPENA1, SERPINA3, SERPINB5 (maspin), SERPINEI (PAl-I), SERPINFI, SHIP-1, SHIP-2, SHB1, SHB2, SHBG, SfcAZ, SLC2A2, SLC33A1, SLC43A1, SLIT2, SPP1, SPRR1B (Sprl), ST6GAL1, STAB1, STAT6, STEAP, STEAP2, TB4R2, TBX21, TCP10, TDGF1, TEK, TGFA, TGFB1, TGFBII1, TGFB2, TGFB3, TGFBI, TGFBR1, TGFBR2, TGFBR3, THIL, THBS1 (thrombospondin-1), THBS2, THBS4, THPO, TIE (Tie-1), TIMP3, tissue factor, TLR10, TLR2, TLR3, TLR4, TLR5, TLR6, TLR7, TLR8, TLR9, TNF, TNFa, TNFAIP2 (B94), TNFAIP3, TNFRSFI1A, TNFRSF1A, TNFRSF1B, TNFRSF21, TNFRSF5, TNFRSF6 (Fas), TNFRSF7, TNFRSF8, TNFRSF9, TNFSF10 (TRAIL), TNFSF11 (TRANCE), TNFSF12 (APO3L), TNFSF13 (April), TNFSF13B, TNFSF14 (HVEM-L), TNFSF15 (VEGI), TNFSF18, TNFSF4 (OX40 ligand), TNFSF5 (CD40 ligand), TNFSF6 (FasL), TNFSF7 (CD27 ligand), TNFSF8 (CD30 ligand), TNFSF9 (4-1BB ligand), TOLLIP, Toll-like receptors, TOP2A (topoisomerase lia), TP53, TPM1, TPM2, TRADD, TRAF1, TRAF2, TRAF3, TRAF4, TRAF5, TRAF6, TRKA, TREM1, TREM2, TRPC6, TSLP, TWEAK, Tyrosinase, uPAR, VEGF, VEGFB, VEGFC, versican, VHL C5, VLA-4, Wnt-1, XCL1 (lymphotactin), XCL2 (SCM-Ib), XCRI (GPRS/CCXCR1), YY1, and ZFPM2.

In some aspects, one or more non-protein molecules, for example, a nucleic acid (e.g., a DNA or an RNA), a lipid, a glycolipid, a polysaccharide, etc. are bound by modified IgGs of the present invention or fused to a modified IgG constant region, or an FcRn-binding fragment thereof (e.g., an Fc region or hinge-Fc region). In some aspects, a tumor-associated glycolipid antigen, (as well as subunits, domains, motifs and epitopes of the same; see, e.g., U.S. Pat. No. 5,091,178) is bound by modified IgGs of the present invention or fused to a modified IgG constant region, or an FcRn-binding fragment thereof.

In some aspects, a modified IgGs or a modified IgG constant domain or FcRn-binding fragment thereof (e.g., an Fc region or hinge-Fc region) comprises a domain (e.g., an epitope binding domain, or ligand domain) that competes with ligands for binding PDGFRalpha, PDGFRbeta, PDGF, VEGF, VEGF-A, VEGF-B, VEGF-C. VEGF-D, VEGFE, VEGFF, VEGFR-1, VEGFR-2, VEGFR-3, FGF, FGF2, HGF, KDR, fit-1, FLK-1 Ang-2, Ang-1, PLGF, CEA, CXCL13, Baff, IL-21, CCL21, TNF-alpha, CXCL12, SDF-1, bFGF, MAC-1, IL23p19, FPR, IGFBP4, CXCR3, TLR4, CXCR2, EphA2, EphA4, EphrinB2, EGFR (ErbB1), HER2 (ErbB2 or p185neu), HER3 (ErbB3), HER4 (ErbB4 or tyro2), SC1, LRP5, LRP6, RAGE, Nav1.7, GLP1, RSV, RSV F protein, Influenza HA protein, Influenza NA protein, HMGB1, CD16, CD19, CD20, CD21, CD28, CD32, CD32b, CD64, CD79, CD22, ICAM-1, FGFR1, FGFR2, HDGF, EphB4, GITR, 13-amyloid, hMPV, PIV-1, PIV-2, OX40L, IGFBP3, cMet, PD-1, PLGF, Neprolysin, CTD, IL-18, IL-6, CXCL-13, IL-1R1, IL-15, IL-4R, IgE, PAl-1, NGF, EphA2, CEA, uPARt, DLL-4, av136, a5131, interferon receptor type I and type II, CD19, ICOS, IL-17, Factor II, Hsp90, IGF, CD19, GM-CSFR, PIV-3, CMV, IL-13, IL-9, and EBV.

The present invention also provides polynucleotides comprising a nucleotide sequence encoding a modified IgG constant domain of the invention or an FcRn-binding fragment thereof (e.g., an Fc region or hinge-Fc region), as well as vectors comprising said polynucleotides. In certain embodiments, the polynucleotide encodes an immunoglobulin, for example an IgG, which includes a modified IgG constant domain or FcRn-binding fragment thereof. In alternative embodiments, the polynucleotide encodes a fusion protein comprising a bioactive molecule and a modified IgG constant domain, or an FcRn-binding fragment thereof.

Furthermore, the invention includes polynucleotides that hybridize under stringent or lower stringent hybridization conditions to polynucleotides encoding modified IgGs and fusion proteins of the present invention.

The nucleotide sequence of modified IgGs and the polynucleotides encoding the same may be obtained by any methods known in the art, including general DNA sequencing method, such as dideoxy chain termination method (Sanger sequencing), and oligonucleotide priming in combination with PCR, respectively.

Identification of Mutations

Amino acid modifications the His435 region of the IgG constant domain as described herein may be introduced utilizing any technique known to those of skill in the art. The constant domain or fragment thereof having one or more modifications in amino acid residues 432-437 (or at other locations in the IgG constant domain, or FcRn binding fragment thereof) may be screened by, for example, a binding assay to identify the constant domain or fragment thereof with increased affinity for the FcRn receptor (as described in more detail below). Those modifications in the hinge-Fc domain or the fragments thereof which increase the affinity of the constant domain or fragment thereof for the FcRn receptor can be introduced into antibodies to increase the in vivo half-lives of said antibodies. Further, those modifications in the constant domain or the fragment thereof which increase the affinity of the constant domain or fragment thereof for FcRn can be fused to bioactive molecules to increase the in vivo half-lives of said bioactive molecules and optionally alter (e.g., increase or decrease) the bioavailability of the molecule, for example, to increase or decrease transport to mucosal surfaces (or other target tissue) (e.g., the lungs).

Mutagenesis

Mutagenesis may be performed in accordance with any of the techniques known in the art including, but not limited to, synthesizing an oligonucleotide having one or more modifications within the sequence of the constant domain of an antibody or a fragment thereof (e.g., the CH2 or CH3 domain) to be modified. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. An exemplary primer is about 17 to about 75 nucleotides or more in length, with about 10 to about 25 or more residues on both sides of the junction of the sequence being altered. A number of such primers introducing a variety of different mutations at one or more positions may be used to generate a library of mutants. The technique of site-specific mutagenesis is well known in the art, as exemplified by various publications (see, e.g., Kunkel et al., *Methods Enzymol.*, 154:367-82, 1987, which is hereby incorporated by reference in its entirety). In general, site-directed mutagenesis is performed by first obtaining a single-stranded vector or melting apart of two strands of a double stranded vector which includes within its sequence a DNA sequence which encodes the desired peptide. An oligonucleotide primer bearing the desired mutated sequence is prepared, generally synthetically. This primer is then annealed with the single-stranded vector, and subjected to DNA polymerizing enzymes such as T7 DNA polymerase, in order to complete the synthesis of the mutation-bearing strand. Thus, a heteroduplex is formed wherein one strand encodes the original non-mutated sequence and the second strand bears the desired mutation. This heteroduplex vector is then used to transform or transfect appropriate cells, such as *E. coli* cells, and clones are selected which include recombinant vectors bearing the mutated sequence arrangement. As will be appreciated, the technique typically employs a phage vector which exists in both a single stranded and double stranded form. Typical vectors useful in site-directed mutagenesis include vectors such as the M13 phage. These phage are readily commercially available and their use is generally well known to those skilled in the art. Double stranded plasmids are also routinely employed in site directed mutagenesis which eliminates the step of transferring the gene of interest from a plasmid to a phage.

Alternatively, the use of PCR™ with commercially available thermostable enzymes such as Taq DNA polymerase may be used to incorporate a mutagenic oligonucleotide primer into an amplified DNA fragment that can then be cloned into an appropriate cloning or expression vector. See, e.g., Tomic et al., *Nucleic Acids Res.*, 18(6):1656, 1987, and Upender et al., *Biotechniques*, 18(1):29-30, 32, 1995, for PCR™-mediated mutagenesis procedures, which are hereby incorporated in their entireties. PCR™ employing a thermostable ligase in addition to a thermostable polymerase may also be used to incorporate a phosphorylated mutagenic oligonucleotide into an amplified DNA fragment that may then be cloned into an appropriate cloning or expression vector (see e.g., Michael, *Biotechniques*, 16(3):410-2, 1994, which is hereby incorporated by reference in its entirety).

Other methods known to those of skill in art of producing sequence variants of the Fc domain of an antibody or a fragment thereof can be used. For example, recombinant vectors encoding the amino acid sequence of the constant domain of an antibody or a fragment thereof may be treated with mutagenic agents, such as hydroxylamine, to obtain sequence variants.

Panning

Vectors, in particular, phage, expressing constant domains or fragments thereof having one or more modifications in amino acid residues 432-437 or other locations can be screened to identify constant domains or fragments thereof having increased affinity for FcRn to select out the highest affinity binders from a population of phage. Immunoassays which can be used to analyze binding of the constant domain or fragment thereof having one or more modifications in amino acid residues 432-437 or other locations to FcRn include, but are not limited to, radioimmunoassays, ELISA (enzyme linked immunosorbent assay), "sandwich" immunoassays, and fluorescent immunoassays. Such assays are routine and well known in the art (see, e.g., Ausubel et al., eds, 1994, *Current Protocols in Molecular Biology*, Vol. 1, John Wiley & Sons, Inc., New York, which is incorporated by reference herein in its entirety). Exemplary immunoassays are described briefly herein below (but are not intended by way of limitation). BIAcore kinetic analysis can also be used to determine the binding on and off rates of a constant domain or a fragment thereof having one or more modifications in amino acid residues 432-437 or other locations to FcRn. BIAcore kinetic analysis comprises analyzing the binding and dissociation of a constant domain or a fragment thereof having one or more modifications in amino acid residues 432-437 or other locations from chips with immobilized FcRn on their surface.

Sequencing

Any of a variety of sequencing reactions known in the art can be used to directly sequence the nucleotide sequence encoding constant domains or fragments thereof having one or more modifications in amino acid residues 432-437 or other locations. Examples of sequencing reactions include those based on techniques developed by Maxim and Gilbert (*Proc. Natl. Acad. Sci. USA,* 74:560, 1977) or Sanger (*Proc. Natl. Acad. Sci. USA,* 74:5463, 1977). It is also contemplated that any of a variety of automated sequencing procedures can be utilized (*Bio/Techniques,* 19:448, 1995), including sequencing by mass spectrometry (see, e.g., PCT Publication No. WO 94/16101, Cohen et al., *Adv. Chromatogr.,* 36:127-162, 1996, and Griffin et al., *Appl. Biochem. Biotechnol.,* 38:147-159, 1993).

Recombinant Methods for Producing Antibodies

The antibodies of the invention or fragments thereof can be produced by any method known in the art for the synthesis of antibodies, in particular, by chemical synthesis or by recombinant expression techniques.

The nucleotide sequence encoding an antibody may be obtained from any information available to those of skill in the art (i.e., from Genbank, the literature, or by routine cloning). If a clone containing a nucleic acid encoding a particular antibody or an epitope-binding fragment thereof is not available, but the sequence of the antibody molecule or epitope-binding fragment thereof is known, a nucleic acid encoding the immunoglobulin may be chemically synthesized or obtained from a suitable source (e.g., an antibody cDNA library, or a cDNA library generated from, or nucleic acid, for example poly $A^+$ RNA, isolated from any tissue or cells expressing the antibody, such as hybridoma cells selected to express an antibody) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, *Molecular Cloning, A Laboratory Manual,* 2d Ed., Cold Spring Harbor Laboratory, Cold Spring Harbor, NY; and Ausubel et al., eds., 1998, *Current Protocols in Molecular Biology,* John Wiley & Sons, NY, which are both incorporated by reference herein in their entireties), to generate antibodies having a different amino acid sequence by, for example, introducing amino acid substitutions, deletions, and/or insertions into the epitope-binding domain regions of the antibodies, for example, into the hinge-Fc regions of the antibodies which are involved in the interaction with FcRn. Antibodies having one or more modifications in amino acid residues 432-437 or other locations can be generated.

Recombinant expression of an antibody requires construction of an expression vector containing a nucleotide sequence that encodes the antibody. Once a nucleotide sequence encoding an antibody molecule or a heavy or light chain of an antibody, or portion thereof (optionally, but not necessarily, containing the heavy or light chain variable region) has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding the constant region of the antibody molecule with one or more modifications in the amino acid residues involved in the interaction with FcRn (see, e.g., PCT Publication WO 86/05807; PCT Publication WO 89/01036; and U.S. Pat. No. 5,122,464). The nucleotide sequence encoding the heavy-chain variable region, light-chain variable region, both the heavy-chain and light-chain variable regions, an epitope-binding fragment of the heavy- and/or light-chain variable region, or one or more complementarity determining regions (CDRs) of an antibody may be cloned into such a vector for expression.

The expression vector is transferred to a host cell by conventional techniques and the transfected cells are then cultured by conventional techniques to produce an antibody having an increased affinity for FcRn and an increased in vivo half-life. Thus, the invention includes host cells containing a polynucleotide encoding an antibody, a constant domain or a FcRn binding fragment thereof having one or more modifications in amino acid residues 432-437 or other locations, optionally operably linked to a heterologous promoter.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include, but are not limited to, microorganisms such as bacteria (e.g., *E. coli* and *B. subtilis*) transformed with recombinant bacteriophage DNA, plasmid DNA or cosmid DNA expression vectors containing antibody coding sequences; yeast (e.g., *Saccharomyces* and *Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; and tobacco mosaic virus, TMV) or transformed with recombinant plasmid expression vectors (e.g., Ti plasmid) containing antibody coding sequences; and mammalian cell systems (e.g., COS, CHO, BHK, 293, 3T3 and NSO cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Bacterial cells such as *Escherichia coli,* and eukaryotic cells, which are well-suited for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., *Gene,* 45:101, 1986, and Cockett et al., *Bio/Technology,* 8:2, 1990).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited to, the E. coli expression vector pUR278 (Ruther et al., EMBO, 12:1791, 1983), in which the antibody coding sequence may be ligated individually into the vector in frame with the lacZ coding region so that a fusion protein is produced; and pIN vectors (Inouye & Inouye, *Nucleic Acids Res.*, 13:3101-3109, 1985 and Van Heeke & Schuster, *J. Biol. Chem.*, 24:5503-5509, 1989).

In an insect system, Autographa californica nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized to express an antibody molecule of the invention. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan & Shenk, *Proc. Natl. Acad. Sci. USA*, 81:355-359, 1984). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bitter et al., *Methods in Enzymol.*, 153:516-544, 1987).

In addition, a host cell strain may be chosen which modulates the expression of the antibody sequences, or modifies and processes the antibody in the specific fashion desired. Such modifications (e.g., glycosylation) and processing (e.g., cleavage) of protein products may be important for the function of the antibody. Different host cells have characteristic and specific mechanisms for the post-translational processing and modification of proteins and gene products. Appropriate cell lines or host systems can be chosen to ensure the correct modification and processing of the antibody expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, HeLa, COS, MDCK, 293, 3T3, W138, and in particular, myeloma cells such as NS0 cells, and related cell lines, see, for example, Morrison et al., U.S. Pat. No. 5,807,715, which is hereby incorporated by reference in its entirety.

For long-term, high-yield production of recombinant antibodies, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compositions that interact directly or indirectly with the antibody molecule.

A number of selection systems may be used, including but not limited to, the herpes simplex virus thymidine kinase (Wigler et al., *Cell*, 11:223, 1977), hypoxanthineguanine phosphoribosyltransferase (Szybalska & Szybalski, *Proc. Natl. Acad. Sci. USA*, 48:202, 1992), and adenine phosphoribosyltransferase (Lowy et al., *Cell*, 22:8-17, 1980) genes can be employed in tk$^-$, hgprt$^-$ or aprt$^-$ cells, respectively. Also, antimetabolite resistance can be used as the basis of selection for the following genes: dhfr, which confers resistance to methotrexate (Wigler et al., *Natl. Acad. Sci. USA*, 77:357, 1980 and O'Hare et al., *Proc. Natl. Acad. Sci. USA*, 78:1527, 1981); gpt, which confers resistance to mycophenolic acid (Mulligan & Berg, *Proc. Natl. Acad. Sci. USA*, 78:2072, 1981); neo, which confers resistance to the aminoglycoside G-418 (Wu and Wu, *Biotherapy*, 3:87-95, 1991; Tolstoshev, *Ann. Rev. Pharmacol. Toxicol.*, 32:573-596, 1993; Mulligan, *Science*, 260:926-932, 1993; and Morgan and Anderson, *Ann. Rev. Biochem.*, 62: 191-217, 1993; and May, *TIB TECH*, 11(5):155-215, 1993); and hygro, which confers resistance to hygromycin (Santerre et al., *Gene*, 30:147, 1984). Methods commonly known in the art of recombinant DNA technology may be routinely applied to select the desired recombinant clone, and such methods are described, for example, in Ausubel et al. (eds.), 1993, *Current Protocols in Molecular Biology*, John Wiley & Sons, NY; Kriegler, 1990, *Gene Transfer and Expression, A Laboratory Manual*, Stockton Press, NY; in Chapters 12 and 13, Dracopoli et al. (eds), 1994, *Current Protocols in Human Genetics*, John Wiley & Sons, NY; and Colberre-Garapin et al., *J. Mol. Biol.*, 150:1, 1981, which are incorporated by reference herein in their entireties.

The expression levels of an antibody molecule can be increased by vector amplification (for a review, see Bebbington and Hentschel, 1987, *The use of vectors based on gene amplification for the expression of cloned genes in mammalian cells in DNA cloning*, Vol. 3. Academic Press, New York). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., *Mol., Cell. Biol.*, 3:257, 1983).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides or different selectable markers to ensure maintenance of both plasmids. Alternatively, a single vector may be used which encodes, and is capable of expressing, both heavy and light chain polypeptides. In such situations, the light chain should be placed before the heavy chain to avoid an excess of toxic free heavy chain (Proudfoot, *Nature,* 322:52, 1986; and Kohler, *Proc. Natl. Acad. Sci. USA,* 77:2 197, 1980). The coding sequences for the heavy and light chains may comprise cDNA or genomic DNA.

Once an antibody molecule of the invention has been produced by recombinant expression, it may be purified by any method known in the art for purification of an immunoglobulin molecule, for example, by chromatography (e.g., ion exchange, affinity, particularly by affinity for the specific antigen after Protein A purification, and sizing column chromatography), centrifugation, differential solubility, or by any other standard techniques for the purification of proteins. Further, the antibodies of the present invention or fragments thereof may be fused to heterologous polypeptide sequences described herein or otherwise known in the art to facilitate purification.

Antibody Conjugates

The present invention encompasses antibodies recombinantly fused or chemically conjugated (including both covalently and non-covalently conjugations) to heterologous polypeptides (i.e., an unrelated polypeptide; or portion thereof, for example at least 10, at least 20, at least 30, at least 40, at least 50, at least 60, at least 70, at least 80, at least 90 or at least 100 amino acids of the polypeptide) to generate fusion proteins. The fusion does not necessarily need to be direct, but may occur through linker sequences. Antibodies fused or conjugated to heterologous polypeptides may also be used in in vitro immunoassays and purification methods using methods known in the art. See e.g., PCT Publication No. WO 93/21232; EP 439,095; Naramura et al., *Immunol. Lett.,* 39:91-99, 1994; U.S. Pat. No. 5,474,981; Gillies et al., *PNAS,* 89:1428-1432, 1992; and Fell et al., *J. Immunol.,* 146:2446-2452, 1991, which are incorporated herein by reference in their entireties.

Antibodies can be fused to marker sequences, such as a peptide to facilitate purification. In some embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., *Proc. Natl. Acad. Sci. USA,* 86:821-824, 1989, for instance, hexa-histidine provides for convenient purification of the fusion protein. Other peptide tags useful for purification include, but are not limited to, the hemagglutinin "HA" tag, which corresponds to an epitope derived from the influenza hemagglutinin protein (Wilson et al., *Cell,* 37:767 1984) and the "flag" tag (Knappik et al., *Biotechniques,* 17(4):754-761, 1994).

The present invention also encompasses antibodies conjugated to a diagnostic or therapeutic agent or any other molecule for which in vivo half-life is desired to be increased. The antibodies can be used diagnostically to, for example, monitor the development or progression of a disease, disorder or infection as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals, and nonradioactive paramagnetic metal ions. The detectable substance may be coupled or conjugated either directly to the antibody or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{111}$In or $^{99m}$Tc.

An antibody may be conjugated to a therapeutic moiety such as a cytotoxin (e.g., a cytostatic or cytocidal agent), a therapeutic agent or a radioactive element (e.g., alpha-emitters, gamma-emitters, etc.). Cytotoxins or cytotoxic agents include any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Further, an antibody may be conjugated to a therapeutic agent or drug moiety that modifies a given biological response. Therapeutic agents or drug moieties are not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon (IFN-α), β-interferon (IFN-β), nerve growth factor (NGF), platelet derived growth factor (PDGF), tissue plasminogen activator (TPA), an apoptotic agent (e.g., TNF-α, TNF-β, AIM I as disclosed in PCT Publication No. WO 97/33899), AIM II (see, PCT Publication No. WO 97/34911), Fas Ligand (Takahashi et al., *J. Immunol.,* 6:1567-1574, 1994), and VEGI (PCT Publication No. WO 99/23105), a thrombotic agent or an anti-angiogenic agent (e.g., angiostatin or endostatin); or a biological response modifier such as, for example, a lymphokine (e.g., interleukin-1 ("IL-1"), interleukin-2 ("IL-2"), interleukin-6 ("IL-6"), granulocyte macrophage colony stimulating factor ("GM-CSF"), and granulocyte colony stimulating factor ("G-CSF")), or a growth factor (e.g., growth hormone ("GH")).

Techniques for conjugating such therapeutic moieties to antibodies are well known; see, e.g., Arnon et al., "Monoclonal Antibodies For Immunotargeting Of Drugs In Cancer Therapy", in *Monoclonal Antibodies And Cancer Therapy,* Reisfeld et al. (eds.), 1985, pp. 243-56, Alan R. Liss, Inc.); Hellstrom et al., "Antibodies For Drug Delivery", in *Controlled Drug Delivery* (2nd Ed.), Robinson et al. (eds.), 1987, pp. 623-53, Marcel Dekker, Inc.); Thorpe, "Antibody Carriers Of Cytotoxic Agents In Cancer Therapy: A Review", in *Monoclonal Antibodies '84: Biological And Clinical Applications*, Pinchera et al. (eds.), 1985, pp. 475-506); "Analysis, Results, And Future Prospective Of The Therapeutic Use Of Radiolabeled Antibody In Cancer Therapy", in *Monoclonal Antibodies For Cancer Detection And Therapy*, Baldwin et al. (eds.), 1985, pp. 303-16, Academic Press; and Thorpe et al., *Immunol. Recombinant expression vector.*, 62:119-58, 1982.

An antibody or fragment thereof, with or without a therapeutic moiety conjugated to it, administered alone or in combination with cytotoxic factor(s) and/or cytokine(s) can be used as a therapeutic.

Alternatively, an antibody can be conjugated to a second antibody to form an antibody heteroconjugate as described by Segal in U.S. Pat. No. 4,676,980, which is incorporated herein by reference in its entirety.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Methods for Producing Fusion Proteins

Fusion proteins can be produced by standard recombinant DNA techniques or by protein synthetic techniques, e.g., by use of a peptide synthesizer. For example, a nucleic acid molecule encoding a fusion protein can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, e.g., *Current Protocols in Molecular Biology*, Ausubel et al., eds., John Wiley & Sons, 1992). Moreover, a nucleic acid encoding a bioactive molecule can be cloned into an expression vector containing the Fc domain or a fragment thereof such that the bioactive molecule is linked in-frame to the constant domain or fragment thereof.

Methods for fusing or conjugating polypeptides to the constant regions of antibodies are known in the art. See, e.g., U.S. Pat. Nos. 5,336,603, 5,622,929, 5,359,046, 5,349,053, 5,447,851, 5,723,125, 5,783,181, 5,908,626, 5,844,095, and 5,112,946; EP 307,434; EP 367,166; EP 394,827; PCT publications WO 91/06570, WO 96/04388, WO 96/22024, WO 97/34631, and WO 99/04813; Ashkenazi et al., *Proc. Natl. Acad. Sci. USA*, 88: 10535-10539, 1991; Traunecker et al., *Nature*, 331:84-86, 1988; Zheng et al., *J. Immunol.*, 154:5590-5600, 1995; and Vil et al., *Proc. Natl. Acad. Sci. USA*, 89:11337-11341, 1992, which are incorporated herein by reference in their entireties.

The nucleotide sequence encoding a bioactive molecule may be obtained from any information available to those of skill in the art (e.g., from Genbank, the literature, or by routine cloning), and the nucleotide sequence encoding a constant domain or a fragment thereof with increased affinity for FcRn may be determined by sequence analysis of mutants produced using techniques described herein, or may be obtained from Genbank or the literature. The nucleotide sequence coding for a fusion protein can be inserted into an appropriate expression vector, i.e., a vector which contains the necessary elements for the transcription and translation of the inserted protein-coding sequence. A variety of host-vector systems may be utilized in the present invention to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

The expression of a fusion protein may be controlled by any promoter or enhancer element known in the art. Promoters which may be used to control the expression of the gene encoding fusion protein include, but are not limited to, the SV40 early promoter region (Bernoist and Chambon, *Nature*, 290:304-310, 1981), the promoter contained in the 3' long terminal repeat of Rous sarcoma virus (Yamamoto, et al., *Cell*, 22:787-797, 1980), the herpes thymidine kinase promoter (Wagner et al., *Proc. Natl. Acad. Sci. U.S.A.*, 78:1441-1445, 1981), the regulatory sequences of the metallothionein gene (Brinster et al., *Nature*, 296:39-42, 1982), the tetracycline (Tet) promoter (Gossen et al., *Proc. Nat. Acad. Sci. USA*, 89:5547-5551, 1995); prokaryotic expression vectors such as the β-lactamase promoter (Villa-Kamaroff, et al., *Proc. Natl. Acad. Sci. U.S.A.*, 75:3727-3731, 1978), or the tac promoter (DeBoer, et al., *Proc. Natl. Acad. Sci. U.S.A.*, 80:21-25, 1983; see also "Useful proteins from recombinant bacteria" in *Scientific American*, 242:74-94, 1980); plant expression vectors comprising the nopaline synthetase promoter region (Herrera-Estrella et al., *Nature*, 303:209-213, 1983) or the cauliflower mosaic virus 35S RNA promoter (Gardner, et al., *Nucl. Acids Res.*, 9:2871, 1981), and the promoter of the photosynthetic enzyme ribulose biphosphate carboxylase (Herrera-Estrella et al., *Nature*, 310:115-120, 1984); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., *Cell* 38:639-646, 1984; Ornitz et al., 50:399-409, *Cold Spring Harbor Symp. Quant. Biol.*, 1986; MacDonald, *Hepatology* 7:425-515, 1987); insulin gene control region which is active in pancreatic beta cells (Hanahan, *Nature* 315:115-122, 1985), immunoglobulin gene control region which is active in lymphoid cells (Grosschedl et al., *Cell*, 38:647-658, 1984; Adames et al., *Nature* 318:533-538, 1985; Alexander et al., *Mol. Cell. Biol.*, 7:1436-1444, 1987), mouse mammary tumor virus control region which is active in testicular, breast, lymphoid and mast cells (Leder et al., *Cell*, 45:485-495, 1986), albumin gene control region which is active in liver (Pinkert et al., *Genes and Devel.*, 1:268-276, 1987), α-fetoprotein gene control region which is active in liver (Krumlauf et al., *Mol. Cell. Biol.*, 5:1639-1648, 1985; Hammer et al., *Science*, 235:53-58, 1987; α1-antitrypsin gene control region which is active in the liver (Kelsey et al., Genes and Devel., 1:161-171, 1987), beta-globin gene control region which is active in myeloid cells (Mogram et al., *Nature*, 315:338-340, 1985; Kollias et al., *Cell*, 46:89-94, 1986; myelin basic protein gene control region which is active in oligodendrocyte cells in the brain (Readhead et al., *Cell*, 48:703-712, 1987); myosin light chain-2 gene control region which is active in skeletal muscle (Sani, *Nature*, 314:283-286, 1985); neuronal-specific enolase (NSE) which is active in neuronal cells (Morelli et al., *Gen. Virol.*, 80:571-83, 1999); brain-derived neurotrophic factor (BDNF) gene control region which is active in neuronal cells (Tabuchi et al., *Biochem. Biophysic. Res. Comprising.*, 253:818-823, 1998); glial fibrillary acidic protein (GFAP) promoter which is active in astrocytes (Gomes et al., Braz. J. Med. Biol. Res., 32(5): 619-631, 1999; Morelli et al., Gen. Virol., 80:571-83, 1999) and gonadotropic releasing hormone gene control region which is active in the hypothalamus (Mason et al., Science, 234:1372-1378, 1986).

In a specific embodiment, the expression of a fusion protein is regulated by a constitutive promoter. In another embodiment, the expression of a fusion protein is regulated by an inducible promoter. In accordance with these embodiments, the promoter may be a tissue-specific promoter.

In a specific embodiment, a vector is used that comprises a promoter operably linked to a fusion protein-encoding nucleic acid, one or more origins of replication, and, optionally, one or more selectable markers (e.g., an antibiotic resistance gene).

In mammalian host cells, a number of viral-based expression systems may be utilized. In cases where an adenovirus is used as an expression vector, the fusion protein coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan & Shenk, Proc. Natl. Acad. Sci. USA, 81:355-359, 1984). Specific initiation signals may also be required for efficient translation of inserted fusion protein coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bitter et al., Methods in Enzymol., 153:516-544, 1987).

Expression vectors containing inserts of a gene encoding a fusion protein can be identified by three general approaches: (a) nucleic acid hybridization, (b) presence or absence of "marker" gene functions, and (c) expression of inserted sequences. In the first approach, the presence of a gene encoding a fusion protein in an expression vector can be detected by nucleic acid hybridization using probes comprising sequences that are homologous to an inserted gene encoding the fusion protein. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of a nucleotide sequence encoding a fusion protein in the vector. For example, if the nucleotide sequence encoding the fusion protein is inserted within the marker gene sequence of the vector, recombinants containing the gene encoding the fusion protein insert can be identified by the absence of the marker gene function. In the third approach, recombinant expression vectors can be identified by assaying the gene product (i.e., fusion protein) expressed by the recombinant. Such assays can be based, for example, on the physical or functional properties of the fusion protein in in vitro assay systems, e.g., binding with anti-bioactive molecule antibody.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered fusion protein may be controlled. Furthermore, different host cells have characteristic and specific mechanisms for the translational and post-translational processing and modification (e.g., glycosylation, phosphorylation of proteins). Appropriate cell lines or host systems can be chosen to ensure the desired modification and processing of the foreign protein expressed. For example, expression in a bacterial system will produce an unglycosylated product and expression in yeast will produce a glycosylated product. Eukaryotic host cells which possess the cellular machinery for proper processing of the primary transcript, glycosylation, and phosphorylation of the gene product may be used. Such mammalian host cells include but are not limited to CHO, VERY, BHK, HeLa, COS, MDCK, 293, 3T3, WI38, and in particular, neuronal cell lines such as, for example, SK-N-AS, SK-N-FI, SK-N-DZ human neuroblastomas (Sugimoto et al., J. Natl. Cancer Inst., 73: 51-57, 1984), SK-N-SH human neuroblastoma (Biochim. Biophys. Acta, 704: 450-460, 1982), Daoy human cerebellar medulloblastoma (He et al., Cancer Res., 52: 1144-1148, 1992) DBTRG-05MG glioblastoma cells (Kruse et al., 1992, In Vitro Cell. Dev. Biol., 28A:609-614, 1992), IMR-32 human neuroblastoma (Cancer Res., 30: 2110-2118, 1970), 1321N1 human astrocytoma (Proc. Natl Acad. Sci. USA, 74: 4816, 1997), MOG-G-CCM human astrocytoma (Br. J. Cancer, 49: 269, 1984), U87MG human glioblastoma-astrocytoma (Acta Pathol. Microbiol. Scand., 74: 465-486, 1968), A172 human glioblastoma (Olopade et al., Cancer Res., 52: 2523-2529, 1992), C6 rat glioma cells (Benda et al., Science, 161: 370-371, 1968), Neuro-2a mouse neuroblastoma (Proc. Natl. Acad. Sci. USA, 65: 129-136, 1970), NB41A3 mouse neuroblastoma (Proc. Natl. Acad. Sci. USA, 48: 1184-1190, 1962), SCP sheep choroid plexus (Bolin et al., J. Virol. Methods, 48: 211-221, 1994), G355-5, PG-4 Cat normal astrocyte (Haapala et al., J. Virol., 53: 827-833, 1985), Mpf ferret brain (Trowbridge et al., In Vitro, 18: 952-960, 1982), and normal cell lines such as, for example, CTX TNA2 rat normal cortex brain (Radany et al., Proc. Natl. Acad. Sci. USA, 89: 6467-6471, 1992) such as, for example, CRL7030 and Hs578Bst. Furthermore, different vector/host expression systems may effect processing reactions to different degrees.

For long-term, high-yield production of recombinant proteins, stable expression is preferred. For example, cell lines which stably express the fusion protein may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched medium, and then are switched to a selective medium. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines that express the differentially expressed or pathway gene protein. Such engineered cell lines may be particularly useful in screening and evaluation of compounds that affect the endogenous activity of the differentially expressed or pathway gene protein.

A number of selection systems may be used, including but not limited to the herpes simplex virus thymidine kinase (Wigler, et al., *Cell*, 11:223, 1997), hypoxanthine-guanine phosphoribosyltransferase (Szybalska & Szybalski, *Proc. Natl. Acad. Sci. USA*, 48:2026, 1962), and adenine phosphoribosyltransferase (Lowy, et al., 1980, *Cell*, 22:817, 1980) genes can be employed in tk–, hgprt– or aprt– cells, respectively. Also, antimetabolite resistance can be used as the basis of selection for dhfr, which confers resistance to methotrexate (Wigler, et al., *Natl. Acad. Sci. USA*, 77:3567, 1980; O'Hare, et al., *Proc. Natl. Acad. Sci. USA*, 78:1527, 1981); gpt, which confers resistance to mycophenolic acid (Mulligan & Berg, *Proc. Natl. Acad. Sci. USA*, 78:2072, 1981); neo, which confers resistance to the aminoglycoside G-418 (Colberre-Garapin, et al., *J. Mol. Biol.*, 150:1, 1981); and hygro, which confers resistance to hygromycin (Santerre, et al., *Gene*, 30:147, 1984) genes.

Once a fusion protein of the invention has been produced by recombinant expression, it may be purified by any method known in the art for purification of a protein, for example, by chromatography (e.g., ion exchange, affinity, particularly by affinity for the specific antigen after Protein A, and sizing column chromatography), centrifugation, differential solubility, or by any other standard technique for the purification of proteins.

Prophylactic and Therapeutic Uses of Antibodies

The present invention encompasses antibody-based therapies which involve administering antibodies to an animal, such as a mammal, including but not limited to a human, for preventing, treating, or ameliorating symptoms associated with a disease, disorder, or infection. Prophylactic and therapeutic compounds of the invention include, but are not limited to, antibodies and nucleic acids encoding antibodies. Antibodies may be provided in pharmaceutically acceptable compositions as known in the art or as described herein.

Antibodies of the present invention that function as antagonists of a disease, disorder, or infection can be administered to an animal, such as a mammal, including but not limited to a human, to treat, prevent or ameliorate one or more symptoms associated with the disease, disorder, or infection. For example, antibodies which disrupt or prevent the interaction between a viral antigen and its host cell receptor may be administered to an animal, such as a mammal, including but not limited to a human, to treat, prevent or ameliorate one or more symptoms associated with a viral infection.

Antibodies which do not prevent a viral or bacterial antigen from binding its host cell receptor but inhibit or downregulate viral or bacterial replication can also be administered to an animal to treat, prevent or ameliorate one or more symptoms associated with a viral or bacterial infection. The ability of an antibody to inhibit or downregulate viral or bacterial replication may be determined by techniques described herein or otherwise known in the art. For example, the inhibition or downregulation of viral replication can be determined by detecting the viral titer in the animal.

Antibodies can also be used to prevent, inhibit or reduce the growth or metastasis of cancerous cells Examples of cancers include, but are not limited to, leukemia (e.g., acute leukemia such as acute lymphocytic leukemia and acute myelocytic leukemia), neoplasms, tumors (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma), heavy chain disease, metastases, or any disease or disorder characterized by uncontrolled cell growth.

Antibodies can also be used to reduce the inflammation experienced by animals, particularly mammals, with inflammatory disorders. Examples of inflammatory disorders include, but are not limited to, rheumatoid arthritis, spondyloarthropathies, inflammatory bowel disease and asthma.

Antibodies can also be used to prevent the rejection of transplants. Antibodies can also be used to prevent clot formation. Further, antibodies that function as agonists of the immune response can also be administered to an animal, such as a mammal, including but not limited to a human, to treat, prevent or ameliorate one or more symptoms associated with the disease, disorder, or infection.

One or more antibodies that immunospecifically bind to one or more antigens may be used locally or systemically in the body as a therapeutic. The antibodies of this invention may also be advantageously utilized in combination with other monoclonal or chimeric antibodies, or with lymphokines or hematopoietic growth factors (such as, e.g., IL-2, IL-3 and IL-7), which, for example, serve to increase the number or activity of effector cells which interact with the antibodies. The antibodies of this invention may also be advantageously utilized in combination with other monoclonal or chimeric antibodies, or with lymphokines or hematopoietic growth factors (such as, e.g., IL-2, IL-3 and IL-7), which, for example, serve to increase the immune response. The antibodies of this invention may also be advantageously utilized in combination with one or more drugs used to treat a disease, disorder, or infection such as, for example anti-cancer agents, anti-inflammatory agents or anti-viral agents. Examples of anti-cancer agents include, but are not limited to, isplatin, ifosfamide, paclitaxel, taxanes, topoisomerase I inhibitors (e.g., CPT-11, topotecan, 9-AC, and GG-211), gemcitabine, vinorelbine, oxaliplatin, 5-fluorouracil (5-FU), leucovorin, vinorelbine, temodal, and taxol. Examples of anti-viral agents include, but are not limited to, cytokines (e.g., IFN-α, IFN-β, IFN-γ), inhibitors of reverse transcriptase (e.g., AZT, 3TC, D4T, ddC, ddI, d4T, 3TC, adefovir, efavirenz, delavirdine, nevirapine, abacavir, and other dideoxynucleosides or dideoxyfluoronucleosides), inhibitors of viral mRNA capping, such as ribavirin, inhibitors of proteases such HIV protease inhibitors (e.g., amprenavir, indinavir, nelfinavir, ritonavir, and saquinavir), amphotericin B, castanospermine as an inhibitor of glycoprotein processing, inhibitors of neuraminidase such as influenza virus neuraminidase inhibitors (e.g., zanamivir and oseltamivir), topoisomerase I inhibitors (e.g., camptothecins and analogs thereof), amantadine, and rimantadine. Examples of anti-inflammatory agents include, but are not limited to, non-steroidal anti-inflammatory drugs such as COX-2 inhibitors (e.g., meloxicam, celecoxib, rofecoxib, flosulide, and SC-58635, and MK-966), ibuprofen and indomethacin, and steroids (e.g., deflazacort, dexamethasone and methylprednisolone).

In a specific embodiment, antibodies administered to an animal are of a species origin or species reactivity that is the same species as that of the animal. Thus, in one embodiment, human or humanized antibodies, or nucleic acids encoding human or human, are administered to a human patient for therapy or prophylaxis.

In some embodiments, immunoglobulins having extended in vivo half-lives are used in passive immunotherapy (for either therapy or prophylaxis). Because of the extended half-life, passive immunotherapy or prophylaxis can be accomplished using lower doses and/or less frequent administration of the therapeutic resulting in fewer side effects, better patient compliance, less costly therapy/prophylaxis, etc.

In a specific embodiment, fusion proteins administered to an animal are of a species origin or species reactivity that is the same species as that of the animal. Thus, in one embodiment, human fusion proteins or nucleic acids encoding human fusion proteins, are administered to a human subject for therapy or prophylaxis.

Prophylactic and Therapeutic Uses of Fusion Proteins and Conjugated Molecules

The present invention encompasses fusion protein-based and conjugated molecule-based therapies which involve administering fusion proteins or conjugated molecules to an animal, such as a mammal, including but not limited to a human, for preventing, treating, or ameliorating symptoms associated with a disease, disorder, or infection. Prophylactic and therapeutic compounds of the invention include, but are not limited to, fusion proteins and nucleic acids encoding fusion proteins and conjugated molecules. Fusion proteins and conjugated molecules may be provided in pharmaceutically acceptable compositions as known in the art or as described herein.

Fusion proteins and conjugated molecules of the present invention that function as antagonists of a disease, disorder, or infection can be administered to an animal, such as a mammal, including but not limited to a human, to treat, prevent or ameliorate one or more symptoms associated with the disease, disorder, or infection. Further, fusion proteins and conjugated molecules of the present invention that function as agonists of the immune response may be administered to an animal, such as a mammal, including but not limited to a human, to treat, prevent or ameliorate one or more symptoms associated with the disease, disorder, or infection.

One or more fusion proteins and conjugated molecules may be used locally or systemically in the body as a therapeutic. The fusion proteins and conjugated molecules of this invention may also be advantageously utilized in combination with monoclonal or chimeric antibodies, or with lymphokines or hematopoietic growth factors (such as, e.g., IL-2, IL-3 and IL-7), which, for example, serve to increase the number or activity of effector cells which interact with the antibodies. The fusion proteins and conjugated molecules of this invention may also be advantageously utilized in combination with monoclonal or chimeric antibodies, or with lymphokines or hematopoietic growth factors (such as, e.g., IL-2, IL-3 and IL-7), which, for example, serve to increase the immune response. The fusion proteins and conjugated molecules of this invention may also be advantageously utilized in combination with one or more drugs used to treat a disease, disorder, or infection such as, for example anti-cancer agents, anti-inflammatory agents or anti-viral agents. Examples of anti-cancer agents include, but are not limited to, isplatin, ifosfamide, paclitaxel, taxanes, topoisomerase I inhibitors (e.g., CPT-11, topotecan, 9-AC, and GG-211), gemcitabine, vinorelbine, oxaliplatin, 5-fluorouracil (5-FU), leucovorin, vinorelbine, temodal, and taxol. Examples of anti-viral agents include, but are not limited to, cytokines (e.g., IFN-α, IFN-β, IFN-γ), inhibitors of reverse transcriptase (e.g., AZT, 3TC, D4T, ddC, ddI, d4T, 3TC, adefovir, efavirenz, delavirdine, nevirapine, abacavir, and other dideoxynucleosides or dideoxyfluoronucleosides), inhibitors of viral mRNA capping, such as ribavirin, inhibitors of proteases such HIV protease inhibitors (e.g., amprenavir, indinavir, nelfinavir, ritonavir, and saquinavir,), amphotericin B, castanospermine as an inhibitor of glycoprotein processing, inhibitors of neuraminidase such as influenza virus neuraminidase inhibitors (e.g., zanamivir and oseltamivir), topoisomerase I inhibitors (e.g., camptothecins and analogs thereof), amantadine, and rimantadine. Examples of anti-inflammatory agents include, but are not limited to, nonsteroidal anti-inflammatory drugs such as COX-2 inhibitors (e.g., meloxicam, celecoxib, rofecoxib, flosulide, and SC-58635, and MK-966), ibuprofen and indomethacin, and steroids (e.g., deflazacort, dexamethasone and methylprednisolone).

Administration of Antibodies or Fusion Proteins

The invention provides methods of treatment, prophylaxis, and amelioration of one or more symptoms associated with a disease, disorder or infection by administrating to a subject of an effective amount of an antibody of the invention, or pharmaceutical composition comprising an antibody of the invention. The invention also provides methods of treatment, prophylaxis, and amelioration of one or more symptoms associated with a disease, disorder or infection by administering to a subject an effective amount of a fusion protein or conjugated molecule of the invention, or a pharmaceutical composition comprising a fusion protein or conjugated molecules of the invention. In one aspect, an antibody or fusion protein or conjugated molecule, is substantially purified (i.e., substantially free from substances that limit its effect or produce undesired side-effects). In a specific embodiment, the subject is an animal, for example a mammal such as non-primate (e.g., cows, pigs, horses, cats, dogs, rats etc.) and a primate (e.g., monkey such as a cynomolgus monkey and a human). In one embodiment, the subject is a human.

Various delivery systems are known and can be used to administer an antibody or fusion protein or conjugated molecule of the invention, e.g., encapsulation in liposomes, microparticles, microcapsules, recombinant cells capable of expressing the antibody or fusion protein, receptor-mediated endocytosis (see, e.g., Wu and Wu, *J. Biol. Chem.*, 262: 4429-4432, 1987), construction of a nucleic acid as part of a retroviral or other vector, etc. Methods of administering an antibody, a fusion protein or conjugated molecule, or pharmaceutical composition include, but are not limited to, parenteral administration (e.g., intradermal, intramuscular, intraperitoneal, intravenous and subcutaneous), epidural, and mucosal (e.g., intranasal and oral routes). In a specific embodiment, antibodies, fusion proteins, conjugated molecules, or pharmaceutical compositions are administered intramuscularly, intravenously, or subcutaneously. The compositions may be administered by any convenient route, for example by infusion or bolus injection, by absorption through epithelial or mucocutaneous linings (e.g., oral mucosa, rectal and intestinal mucosa, etc.) and may be administered together with other biologically active agents.

Administration can be systemic or local. In addition, pulmonary administration can also be employed, e.g., by use of an inhaler or nebulizer, and formulation with an aerosolizing agent. See, e.g., U.S. Pat. Nos. 6,019,968; 5,985, 320; 5,985,309; 5,934,272; 5,874,064; 5,855,913; 5,290,540; and 4,880,078; and PCT Publication Nos. WO 92/19244; WO 97/32572; WO 97/44013; WO 98/31346; and WO 99/66903, each of which is incorporated herein by reference in its entirety. In one embodiment, an antibody, a fusion protein, conjugated molecules, or a pharmaceutical composition is administered using Alkermes AIR™ pulmonary drug delivery technology (Alkermes, Inc., Cambridge, Mass.).

The invention also provides that an antibody, a fusion protein, or conjugated molecule is packaged in a hermetically sealed container such as an ampoule or sachette indicating the quantity of antibody, fusion protein, or conjugated molecule. In one embodiment, the antibody, fusion protein, or conjugated molecule is supplied as a dry sterilized lyophilized powder or water free concentrate in a hermetically sealed container and can be reconstituted, e.g., with water or saline to the appropriate concentration for administration to a subject. In one embodiment, the antibody, fusion protein, or conjugated molecule is supplied as a dry sterile lyophilized powder in a hermetically sealed container at a unit dosage of at least 5 mg, at least 10 mg, at least 15 mg, at least 25 mg, at least 35 mg, at least 45 mg, at least 50 mg, or at least 75 mg. The lyophilized antibody, fusion protein, or conjugated molecule should be stored at between 2 and 8° C. in its original container and the antibody, fusion protein, or conjugated molecules should be administered within 12 hours, within 6 hours, within 5 hours, within 3 hours, or within 1 hour after being reconstituted. In an alternative embodiment, an antibody, fusion protein, or conjugated molecule is supplied in liquid form in a hermetically sealed container indicating the quantity and concentration of the antibody, fusion protein, or conjugated molecule. In one embodiment, the liquid form of the antibody, fusion protein, or conjugated molecule is supplied in a hermetically sealed container at least 1 mg/ml, at least 2.5 mg/ml, at least 5 mg/ml, at least 8 mg/ml, at least 10 mg/ml, at least 15 mg/kg, or at least 25 mg/ml.

In a specific embodiment, it may be desirable to administer the pharmaceutical compositions of the invention locally to the area in need of treatment; this may be achieved by, for example, and not by way of limitation, local infusion, by injection, or by means of an implant, said implant being of a porous, non-porous, or gelatinous material, including membranes, such as sialastic membranes, or fibers. Optionally, when administering an antibody or a fusion protein, care is taken to use materials to which the antibody or the fusion protein does not absorb.

The composition can optionally be delivered in a vesicle, in particular a liposome (see Langer, *Science*, 249:1527-1533, 1990; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

The composition can optionally be delivered in a controlled release or sustained release system. Any technique known to one of skill in the art can be used to produce sustained release formulations comprising one or more antibodies, or one or more fusion proteins. See, e.g., U.S. Pat. No. 4,526,938; PCT publication WO 91/05548; PCT publication WO 96/20698; Ning et al., "Intratumoral Radioimmunotheraphy of a Human Colon Cancer Xenograft Using a Sustained-Release Gel," *Radiotherapy & Oncology*, 39:179-189, 1996; Song et al., "Antibody Mediated Lung Targeting of Long-Circulating Emulsions," *PDA Journal of Pharmaceutical Science & Technology*, 50:372-397, 1995; Cleek et al., "Biodegradable Polymeric Carriers for a bFGF Antibody for Cardiovascular Application," *Pro. Intl. Symp. Control. Rel. Bioact. Mater.*, 24:853-854, 1997; and Lam et al., "Microencapsulation of Recombinant Humanized Monoclonal Antibody for Local Delivery," *Proc. Int'l. Symp. Control Rel. Bioact. Mater.*, 24:759-760, 1997, each of which is incorporated herein by reference in its entirety. In one embodiment, a pump may be used in a controlled release system (see Langer, supra; Sefton, *CRC Crit. Ref. Biomed. Eng.*, 14:20, 1987; Buchwald et al., Surgery, 88:507, 1980; and Saudek et al., *N. Engl. J. Med.*, 321:574, 1989). Optionally, polymeric materials can be used to achieve controlled release of antibodies or fusion proteins (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, *J. Macromol. Sci. Rev. Macromol. Chem.*, 23:61, 1983; see also Levy et al., *Science*, 228:190, 1985; During et al., *Ann. Neurol.*, 25:351, 1989; Howard et al., *J. Neurosurg.*, 71:105, 1989); U.S. Pat. Nos. 5,679,377; 5,916,597; 5,912,015; 5,989,463; 5,128,326; PCT Publication No. WO 99/15154; and PCT Publication No. WO 99/20253). Optionally, a controlled release system can be placed in proximity of the therapeutic target (e.g., the lungs), thus requiring only a fraction of the systemic dose (see, e.g., Goodson, in Medical Applications of Controlled Release, supra, vol. 2, pp. 115-138 (1984)).

Other controlled release systems are discussed in the review by Langer, *Science*, 249:1527-1533, 1990).

In a specific embodiment where the composition of the invention is a nucleic acid encoding an antibody or fusion protein, the nucleic acid can be administered in vivo to promote expression of its encoded antibody or fusion protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., *Proc. Natl. Acad. Sci. USA*, 88:1864-1868, 1991), etc. Alternatively, a nucleic acid can be introduced intracellularly and incorporated within host cell DNA for expression by homologous recombination.

The present invention also provides pharmaceutical compositions. Such compositions comprise a prophylactically or therapeutically effective amount of an antibody, fusion protein or conjugated molecule, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's complete and incomplete, mineral gels such as aluminum hydroxide, surface active substances such as lysolecithin, pluronic polyols, polyanions, peptides, oil emulsions, keyhole limpet hemocyanins, dinitrophenol, and potentially useful adjuvants for humans such as BCG (Bacille Calmette-Guerin) and *Corynebacterium parvum*), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a suitable carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a prophylactically or therapeutically effective amount of the antibody or fragment thereof, or fusion protein or conjugated molecule, optionally in purified form, together with a suitable amount of carrier so as to provide the form for proper administration to the patient. The formulation should suit the mode of administration.

In one embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection.

Generally, the ingredients of compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the composition of the invention which will be effective in the treatment, prevention or amelioration of one or more symptoms associated with a disease, disorder, or infection can be determined by standard clinical techniques. The precise dose to be employed in the formulation will depend on the route of administration, the age of the subject, and the seriousness of the disease, disorder, or infection, and should be decided according to the judgment of the practitioner and each patient's circumstances. Effective doses may be extrapolated from dose-response curves derived from in vitro or animal model (e.g., the cotton rat or Cynomolgus monkey) test systems.

For fusion proteins, the therapeutically or prophylactically effective dosage administered to a subject ranges from about 0.001 to 50 mg/kg body weight, about 0.01 to 25 mg/kg body weight, about 0.1 to 20 mg/kg body weight, about 1 to 10 mg/kg, 2 to 9 mg/kg, 3 to 8 mg/kg, 4 to 7 mg/kg, or 5 to 6 mg/kg body weight. For antibodies, the therapeutically or prophylactically effective dosage administered to a subject is typically 0.1 mg/kg to 200 mg/kg of the subject's body weight. In one embodiment, the dosage administered to a subject is between 0.1 mg/kg and 20 mg/kg of the subject's body weight. For example, the dosage administered to a subject can be between 1 mg/kg to 10 mg/kg of the subject's body weight. The dosage will, however, depend upon the extent to which the in vivo half-life of the molecule has been increased. Generally, human antibodies and human fusion proteins have longer half-lives within the human body than antibodies of fusion proteins from other species due to the immune response to the foreign polypeptides. Thus, lower dosages of human antibodies or human fusion proteins and less frequent administration is often possible. Further, the dosage and frequency of administration of antibodies, fusion proteins, or conjugated molecules may be reduced also by enhancing uptake and tissue penetration (e.g., into the lung) of the antibodies or fusion proteins by modifications such as, for example, lipidation.

Treatment of a subject with a therapeutically or prophylactically effective amount of an antibody, fusion protein, or conjugated molecule can include a single treatment or can include a series of treatments. In one example, a subject is treated with an antibody, fusion protein, or conjugated molecule in the range of between about 0.1 to 30 mg/kg body weight, one time per week for between about 1 to 10 weeks, between 2 to 8 weeks, between about 3 to 7 weeks, or for about 4, 5, or 6 weeks. In some embodiments, the pharmaceutical composition of the invention is administered once a day, twice a day, or three times a day. In some embodiments, the pharmaceutical composition is administered once a week, twice a week, once every two weeks, once a month, once every six weeks, once every two months, twice a year or once per year. It will also be appreciated that the effective dosage of the antibody, fusion protein, or conjugated molecule used for treatment may increase or decrease over the course of a particular treatment.

Gene Therapy

In a specific embodiment, nucleic acids comprising sequences encoding antibodies or fusion proteins, are administered to treat, prevent or ameliorate one or more symptoms associated with a disease, disorder, or infection, by way of gene therapy. Gene therapy refers to therapy performed by the administration to a subject of an expressed or expressible nucleic acid. In this embodiment of the invention, the nucleic acids produce their encoded antibody or fusion protein that mediates a therapeutic or prophylactic effect.

Any of the methods for gene therapy available in the art can be used according to the present invention. Exemplary methods are described below.

For general reviews of the methods of gene therapy, see Goldspiel et al., *Clinical Pharmacy*, 12:488-505, 1993; Wu and Wu, *Biotherapy*, 3:87-95, 1991; Tolstoshev, *Ann. Rev. Pharmacol. Toxicol.*, 32:573-596, 1993; Mulligan, *Science*, 260:926-932, 1993; and Morgan and Anderson, *Ann. Rev. Biochem.* 62:191-217, 1993; *TIBTECH* 11(5):155-215, 1993. Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In one aspect, a composition of the invention comprises nucleic acids encoding an antibody, said nucleic acids being part of an expression vector that expresses the antibody in a suitable host. In particular, such nucleic acids have promoters, which can be heterologous or homologous promoters, operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, *Proc. Natl. Acad. Sci. USA*, 86:8932-8935, 1989; and Zijlstra et al., *Nature*, 342:435-438, 1989).

In another aspect, a composition of the invention comprises nucleic acids encoding a fusion protein, said nucleic acids being a part of an expression vector that expression the fusion protein in a suitable host. In particular, such nucleic acids have promoters, which can be heterologous or homologous promoters, operably linked to the coding region of a fusion protein, said promoter being inducible or constitutive, and optionally, tissue-specific. In another particular embodiment, nucleic acid molecules are used in which the coding sequence of the fusion protein and any other desired sequences are flanked by regions that promote homologous recombination at a desired site in the genome, thus providing for intrachromosomal expression of the fusion protein encoding nucleic acids.

Delivery of the nucleic acids into a subject may be either direct, in which case the subject is directly exposed to the nucleic acid or nucleic acid-carrying vectors, or indirect, in which case, cells are first transformed with the nucleic acids in vitro, then transplanted into the subject. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retroviral or other viral vectors (see U.S. Pat. No. 4,980, 286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, *J. Biol. Chem.*, 262:4429-4432, 1987) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO 92/20316; WO 93/14188; WO 93/20221). Alternatively, the nucleic acid can be introduced intracellularly and incorporated within host cell DNA for expression, by homologous recombination (Koller and Smithies, *Proc. Natl. Acad. Sci. USA*, 86:8932-8935, 1989; and Zijlstra et al., *Nature*, 342:435-438, 1989).

In a specific embodiment, viral vectors that contain nucleic acid sequences encoding an antibody or a fusion protein are used. For example, a retroviral vector can be used (see Miller et al., *Meth. Enzymol.*, 217:581-599, 1993). These retroviral vectors contain the components necessary for the correct packaging of the viral genome and integration into the host cell DNA. The nucleic acid sequences encoding the antibody or a fusion protein to be used in gene therapy are cloned into one or more vectors, which facilitates delivery of the nucleotide sequence into a subject. More detail about retroviral vectors can be found in Boesen et al., *Biotherapy*, 6:291-302, 1994, which describes the use of a retroviral vector to deliver the mdr 1 gene to hematopoietic stem cells in order to make the stem cells more resistant to chemotherapy. Other references illustrating the use of retroviral vectors in gene therapy are: Clowes et al., *J. Clin. Invest.*, 93:644-651, 1994; Klein et al., Blood 83:1467-1473, 1994; Salmons and Gunzberg, *Human Gene Therapy*, 4:129-141, 1993; and Grossman and Wilson, *Curr. Opin. in Genetics and Devel.*, 3:110-114, 1993.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, *Current Opinion in Genetics and Development*, 3:499-503, 1993, present a review of adenovirus-based gene therapy. Bout et al., *Human Gene Therapy*, 5:3-10, 1994, demonstrated the use of adenovirus vectors to transfer genes to the respiratory epithelia of rhesus monkeys. Other instances of the use of adenoviruses in gene therapy can be found in Rosenfeld et al., *Science*, 252:431-434, 1991; Rosenfeld et al., *Cell*, 68:143-155, 1992; Mastrangeli et al., *J. Clin. Invest.*, 91:225-234, 1993; PCT Publication WO 94/12649; and Wang et al., *Gene Therapy*, 2:775-783, 1995. In a one embodiment, adenovirus vectors are used.

Adeno-associated virus (AAV) has also been proposed for use in gene therapy (see, e.g., Walsh et al., *Proc. Soc. Exp. Biol. Med.*, 204:289-300, 1993, and U.S. Pat. No. 5,436, 146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a subject.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell mediated gene transfer, spheroplast fusion, etc. Numerous techniques are known in the art for the introduction of foreign genes into cells (see, e.g., Loeffler and Behr, *Meth. Enzymol.*, 217:599-618, 1993; Cohen et al., *Meth. Enzymol.*, 217:618-644, 1993; and *Clin. Pharma. Ther.*, 29:69-92, 1985) and may be used in accordance with the present invention, provided that the necessary developmental and physiological functions of the recipient cells are not disrupted. The technique should provide for the stable transfer of the nucleic acid to the cell, so that the nucleic acid is expressible by the cell and optionally heritable and expressible by its cell progeny.

The resulting recombinant cells can be delivered to a subject by various methods known in the art. For example, recombinant blood cells (e.g., hematopoietic stem or progenitor cells) can be administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a one embodiment, the cell used for gene therapy is autologous to the subject.

In an embodiment in which recombinant cells are used in gene therapy, nucleic acid sequences encoding an antibody or a fusion protein are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g., PCT Publication WO 94/08598; Stemple and Anderson, *Cell*, 71:973-985, 1992; Rheinwald, *Meth. Cell Bio.*, 21A: 229, 1980; and Pittelkow and Scott, *Mayo Clinic Proc.*, 61:771, 1986).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

Characterization and Demonstration of Therapeutic or Prophylactic Utility

Antibodies, fusion proteins, and conjugated molecules of the present invention may be characterized in a variety of ways. In particular, antibodies of the invention may be assayed for the ability to immunospecifically bind to an antigen. Such an assay may be performed in solution (e.g., Houghten, *Bio/Techniques*, 13:412-421, 1992), on beads (Lam, *Nature*, 354:82-84, 1991, on chips (Fodor, *Nature*, 364:555-556, 1993), on bacteria (U.S. Pat. No. 5,223,409), on spores (U.S. Pat. Nos. 5,571,698; 5,403,484; and 5,223, 409), on plasmids (Cull et al., *Proc. Natl. Acad. Sci. USA*, 89:1865-1869, 1992) or on phage (Scott and Smith, *Science*, 249:386-390, 1990; Devlin, *Science*, 249:404-406, 1990; Cwirla et al., *Proc. Natl. Acad. Sci. USA*, 87:6378-6382, 1990; and Felici, *J. Mol. Biol.*, 222:301-310, 1991) (each of these references is incorporated herein in its entirety by reference). Antibodies that have been identified to immunospecifically bind to an antigen or a fragment thereof can then be assayed for their specificity affinity for the antigen.

The antibodies of the invention or fragments thereof may be assayed for immunospecific binding to an antigen and cross-reactivity with other antigens by any method known in the art. Immunoassays which can be used to analyze immunospecific binding and cross-reactivity include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1 to 4 hours) at 40° C., adding protein A and/or protein G sepharose beads to the cell lysate, incubating for about an hour or more at 40° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}$P or $^{125}$I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., $^3$H or $^{125}$I) with the antibody of interest in the presence of increasing amounts of unlabeled antigen, and the detection of the antibody bound to the labeled antigen. The affinity of the antibody of the present invention or a fragment thereof for the antigen and the binding off-rates can be determined from the saturation data by scatchard analysis. Competition with a second antibody can also be determined using radioimmunoassays. In this case, the antigen is incubated with an antibody of the present invention or a fragment thereof conjugated to a labeled compound (e.g., $^3$H or $^{125}$I) in the presence of increasing amounts of an unlabeled second antibody.

In an embodiment, BIAcore kinetic analysis is used to determine the binding on and off rates of antibodies to an antigen. BIAcore kinetic analysis comprises analyzing the binding and dissociation of an antigen from chips with immobilized antibodies on their surface.

The antibodies of the invention as well as fusion proteins and conjugated molecules can also be assayed for their ability to inhibit the binding of an antigen to its host cell receptor using techniques known to those of skill in the art. For example, cells expressing the receptor for a viral antigen can be contacted with virus in the presence or absence of an antibody and the ability of the antibody to inhibit viral antigen's binding can measured by, for example, flow cytometry or a scintillation counter. The antigen or the antibody can be labeled with a detectable compound such as a radioactive label (e.g., $^{32}$P, $^{35}$S, and $^{125}$I) or a fluorescent label (e.g., fluorescein isothiocyanate, rhodamine, phycoerythrin, phycocyanin, allophycocyanin, o-phthaldehyde and fluorescamine) to enable detection of an interaction between the antigen and its host cell receptor. Alternatively, the ability of antibodies to inhibit an antigen from binding to its receptor can be determined in cell-free assays. For example, virus or a viral antigen (e.g., RSV F glycoprotein) can be contacted in a cell-free assay with an antibody and the ability of the antibody to inhibit the virus or the viral antigen from binding to its host cell receptor can be determined. Optionally, the antibody is immobilized on a solid support and the antigen is labeled with a detectable compound. Alternatively, the antigen is immobilized on a solid support and the antibody is labeled with a detectable compound. The antigen may be partially or completely purified (e.g., partially or completely free of other polypeptides) or part of a cell lysate. Further, the antigen may be a fusion protein comprising the viral antigen and a domain such as glutathionine-S-transferase. Alternatively, an antigen can be biotinylated using techniques well known to those of skill in the art (e.g., biotinylation kit, Pierce Chemicals; Rockford, Ill.).

The antibodies, fusion proteins, and conjugated molecules of the invention can also be assayed for their ability to inhibit or downregulate viral or bacterial replication using techniques known to those of skill in the art. For example, viral replication can be assayed by a plaque assay such as described, e.g., by Johnson et al., *Journal of Infectious Diseases,* 176:1215-1224, 1997. The antibodies, fusion proteins, and conjugated molecules of the invention of the invention can also be assayed for their ability to inhibit or downregulate the expression of viral or bacterial polypeptides. Techniques known to those of skill in the art, including, but not limited to, Western blot analysis, Northern blot analysis, and RT-PCR, can be used to measure the expression of viral or bacterial polypeptides. Further, the antibodies, fusion proteins, and conjugated molecules of the invention of the invention can be assayed for their ability to prevent the formation of syncytia.

The antibodies, fusion proteins, conjugated molecules, and compositions of the invention are optionally tested in vitro, and then in vivo for the desired therapeutic or prophylactic activity, prior to use in humans. For example, in vitro assays which can be used to determine whether administration of a specific antibody, a specific fusion protein, a specific conjugated molecule, or a composition of the present invention is indicated, include in vitro cell culture assays in which a subject tissue sample is grown in culture, and exposed to or otherwise administered an antibody, a fusion protein, conjugated molecule, or composition of the present invention, and the effect of such an antibody, a fusion protein, conjugated molecule, or a composition of the present invention upon the tissue sample is observed. In various specific embodiments, in vitro assays can be carried out with representative cells of cell types involved in a disease or disorder, to determine if an antibody, a fusion protein, conjugated molecule, or composition of the present invention has a desired effect upon such cell types. Optionally, the antibodies, the fusion proteins, the conjugated molecules, or compositions of the invention are also tested in in vitro assays and animal model systems prior to administration to humans.

Antibodies, fusion proteins, conjugated molecules, or compositions of the present invention for use in therapy can be tested for their toxicity in suitable animal model systems, including but not limited to rats, mice, cows, monkeys, and rabbits. For in vivo testing for the toxicity of an antibody, a fusion protein, a conjugated molecule, or a composition, any animal model system known in the art may be used.

Efficacy in treating or preventing viral infection may be demonstrated by detecting the ability of an antibody, a fusion protein, a conjugated molecule, or a composition of the invention to inhibit the replication of the virus, to inhibit transmission or prevent the virus from establishing itself in its host, or to prevent, ameliorate or alleviate one or more symptoms associated with viral infection. The treatment is considered therapeutic if there is, for example, a reduction is viral load, amelioration of one or more symptoms or a decrease in mortality and/or morbidity following administration of an antibody, a fusion protein, a conjugated molecule, or a composition of the invention. Antibodies, fusion proteins, conjugated molecules, or compositions of the invention can also be tested for their ability to inhibit viral replication or reduce viral load in in vitro and in vivo assays.

Efficacy in treating or preventing bacterial infection may be demonstrated by detecting the ability of an antibody, a fusion protein or a composition of the invention to inhibit the bacterial replication, or to prevent, ameliorate or alleviate one or more symptoms associated with bacterial infection.

The treatment is considered therapeutic if there is, for example, a reduction is bacterial numbers, amelioration of one or more symptoms or a decrease in mortality and/or morbidity following administration of an antibody, a fusion protein or a composition of the invention.

Efficacy in treating cancer may be demonstrated by detecting the ability of an antibody, a fusion protein, a conjugated molecule, or a composition of the invention to inhibit or reduce the growth or metastasis of cancerous cells or to ameliorate or alleviate one or more symptoms associated with cancer. The treatment is considered therapeutic if there is, for example, a reduction in the growth or metastasis of cancerous cells, amelioration of one or more symptoms associated with cancer, or a decrease in mortality and/or morbidity following administration of an antibody, a fusion protein, a conjugated molecule, or a composition of the invention. Antibodies, fusion proteins or compositions of the invention can be tested for their ability to reduce tumor formation in in vitro, ex vivo, and in vivo assays.

Efficacy in treating inflammatory disorders may be demonstrated by detecting the ability of an antibody, a fusion protein, a conjugated molecule, or a composition of the invention to reduce or inhibit the inflammation in an animal or to ameliorate or alleviate one or more symptoms associated with an inflammatory disorder. The treatment is considered therapeutic if there is, for example, a reduction is in inflammation or amelioration of one or more symptoms following administration of an antibody, a fusion protein, a conjugated molecule, or a composition of the invention.

Antibodies, fusion proteins, conjugated molecules, or compositions of the invention can be tested in vitro and in vivo for the ability to induce the expression of cytokines (e.g., IFN-α, IFN-β, IFN-γ, IL-2, IL-3, IL-4, IL-5, IL-6, IL10, IL-12, and IL-15) and activation markers (e.g., CD28, ICOS, and SLAM). Techniques known to those of skill in the art can be used to measure the level of expression of cytokines and activation markers. For example, the level of expression of cytokines can be measured by analyzing the level of RNA of cytokines by, for example, RT-PCR and Northern blot analysis, and by analyzing the level of cytokines by, for example, immunoprecipitation followed by Western blot analysis or ELISA.

Antibodies, fusion proteins, conjugated molecules, or compositions of the invention can be tested in vitro and in vivo for their ability to modulate the biological activity of immune cells, e.g., human immune cells (e.g., T-cells, B-cells, and Natural Killer cells). The ability of an antibody, a fusion protein, a conjugated molecule, or a composition of the invention to modulate the biological activity of immune cells can be assessed by detecting the expression of antigens, detecting the proliferation of immune cells, detecting the activation of signaling molecules, detecting the effector function of immune cells, or detecting the differentiation of immune cells. Techniques known to those of skill in the art can be used for measuring these activities. For example, cellular proliferation can be assayed by 3H-thymidine incorporation assays and trypan blue cell counts. Antigen expression can be assayed, for example, by immunoassays including, but are not limited to, competitive and non-competitive assay systems using techniques such as Western blots, immunohistochemistry, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays and FACS analysis. The activation of signaling molecules can be assayed, for example, by kinase assays and electrophoretic shift assays (EMSAs).

Antibodies, fusion proteins, conjugated molecules, or compositions of the invention can also be tested for their ability to increase the survival period of animals, such as mammals, including but not limited to humans, suffering from a disease, disorder, or infection by at least 25%, at least 50%, at least 60%, at least 75%, at least 85%, at least 95%, or at least 99%. Further, antibodies, fusion proteins, conjugated molecules, or compositions of the invention can be tested for their ability reduce the hospitalization period of animals, such as mammals including but not limited to humans, suffering from a disease, disorder, or infection by at least 60%, at least 75%, at least 85%, at least 95%, or at least 99%. Techniques known to those of skill in the art can be used to analyze the function of the antibodies or compositions of the invention in vivo.

Diagnostic Uses of Antibodies and Fusion Proteins

Labeled antibodies, fusion proteins, and conjugated molecules of the invention can be used for diagnostic purposes to detect, diagnose, or monitor diseases, disorders or infections. The invention provides for the detection or diagnosis of a disease, disorder or infection, comprising: (a) assaying the expression of an antigen in cells or a tissue sample of a subject using one or more antibodies that immunospecifically bind to the antigen; and (b) comparing the level of the antigen with a control level, e.g., levels in normal tissue samples, whereby an increase in the assayed level of antigen compared to the control level of the antigen is indicative of the disease, disorder or infection. The invention also provides for the detection or diagnosis of a disease, disorder or infection, comprising (a) assaying the expression of an antigen in cells or a tissue sample of a subject using one or fusion proteins or conjugated molecules of the invention that bind to the antigen; and (b) comparing the level of the antigen with a control level, e.g., levels in normal tissue samples, whereby an increase of antigen compared to the control level of the antigen is indicative of the disease, disorder or infection. Accordingly, the fusion protein or conjugated molecule comprises a bioactive molecule such as a ligand, cytokine or growth factor and the hinge-Fc region or fragments thereof, wherein the fusion protein or conjugated molecule is capable of binding to an antigen being detected.

Antibodies of the invention can be used to assay antigen levels in a biological sample using classical immunohistological methods as described herein or as known to those of skill in the art (e.g., see Jalkanen et al., *J. Cell. Biol.*, 101:976-985, 1985; Jalkanen et al., *J. Cell. Biol.*, 105:3087-3096, 1987). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, alkaline phosphatase, glucose oxidase; radioisotopes, such as iodine ($^{125}$I, $^{131}$I) carbon ($^{14}$C), sulfur ($^{35}$S), tritium ($^{3}$H), indium ($^{121}$In), and technetium ($^{99m}$Tc); luminescent labels, such as luminol; and fluorescent labels, such as fluorescein and rhodamine.

Fusion proteins can be used to assay antigen levels in a biological sample using, for example, SDS-PAGE and immunoassays known to those of skill in the art.

One aspect of the invention is the detection and diagnosis of a disease, disorder, or infection in a human. In one embodiment, diagnosis comprises: a) administering (for example, parenterally, subcutaneously, or intraperitoneally) to a subject an effective amount of a labeled antibody that immunospecifically binds to an antigen; b) waiting for a time interval following the administration for permitting the labeled antibody to preferentially concentrate at sites in the subject where the antigen is expressed (and for unbound labeled molecule to be cleared to background level); c) determining background level; and d) detecting the labeled antibody in the subject, such that detection of labeled antibody above the background level indicates that the subject has the disease, disorder, or infection. In accordance with this embodiment, the antibody is labeled with an imaging moiety which is detectable using an imaging system known to one of skill in the art. Background level can be determined by various methods including, comparing the amount of labeled molecule detected to a standard value previously determined for a particular system.

In another embodiment, diagnosis comprises: a) administering (for example, parenterally, subcutaneously, or intraperitoneally) to a subject an effective amount of a labeled fusion protein or conjugated molecule that binds to an antigen or some other molecule; b) waiting for a time interval following the administration for permitting the labeled fusion protein or conjugated molecule to preferentially concentrate at sites in the subject where the antigen or other molecule is expressed (and for unbound labeled molecule to be cleared to background level); c) determining background level; and d) detecting the labeled fusion protein or conjugated molecule in the subject, such that detection of labeled fusion protein above the background level indicates that the subject has the disease, disorder, or infection. In accordance with this embodiment, the fusion protein or conjugated molecule comprises a bioactive molecule such as a ligand, cytokine or growth factor, and a modified IgG or FcRn-binding fragment thereof (e.g., an Fc region or hinge-Fc region), wherein said fusion protein or conjugated molecule is labeled with an imaging moiety and is capable of binding to the antigen being detected.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99m}$Tc. The labeled antibody will then preferentially accumulate at the location of cells which contain the specific protein. In vivo tumor imaging is described in S. W. Burchiel et al., "Immunopharmacokinetics of Radiolabeled Antibodies and Their Fragments," Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In one embodiment, monitoring of a disease, disorder or infection is carried out by repeating the method for diagnosing the disease, disorder or infection, for example, one month after initial diagnosis, six months after initial diagnosis, one year after initial diagnosis, etc.

Presence of the labeled molecule can be detected in the subject using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patient using positron emission-tomography. In yet another embodiment, the molecule is labeled with a paramagnetic label and is detected in a patient using magnetic resonance imaging (MM).

Kits

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The present invention provides kits that can be used in the above methods. In one embodiment, a kit comprises an antibody, fusion protein, or conjugated molecule, of the invention, optionally in a purified form, in one or more containers. In a specific embodiment, the kits of the present invention contain a substantially isolated antigen as a control. Optionally, the kits of the present invention further comprise a control antibody, fusion protein, or conjugated molecule which does not react with the antigen included in the kit. In another specific embodiment, the kits of the present invention contain a means for detecting the binding of an antibody, fusion protein, or conjugated molecule, to an antigen (e.g., the antibody, fusion protein, or conjugated molecule, may be conjugated to a detectable substrate such as a fluorescent compound, an enzymatic substrate, a radioactive compound or a luminescent compound, or a second antibody which recognizes the first antibody may be conjugated to a detectable substrate). In specific embodiments, the kit may include a recombinantly produced or chemically synthesized antigen. The antigen provided in the kit may also be attached to a solid support. In a more specific embodiment the detecting means of the above-described kit includes a solid support to which antigen is attached. Such a kit may also include a non-attached reporter-labeled anti-human antibody. In this embodiment, binding of the antibody to the antigen can be detected by binding of the said reporter-labeled antibody.

In Vitro and in Vivo Assays for Half-Life of Modified IgG Constant Domains or FcRn-Binding Fragments Thereof The ability of modified IgGs and other molecules comprising a modified IgG constant domain or an FcRn-binding fragment thereof to bind to FcRn can be characterized by various in vitro assays, including those exemplified in the examples provided herein. PCT publications WO 97/34631 by Ward and WO 02/060919 by Dall'Acqua et al. also disclose various methods in detail and are incorporated herein in its entirety by reference.

For example, in order to compare the ability of the modified IgG or fragments thereof to bind to FcRn with that of the wild type IgG, the modified IgG or fragments thereof and the wild type IgG can be radio-labeled and reacted with FcRn-expressing cells in vitro. The radioactivity of the cell-bound fractions can be then counted and compared. The cells expressing FcRn to be used for this assay can be, for example, endothelial cell lines including mouse pulmonary capillary endothelial cells (B10, D2.PCE) derived from lungs of B10.DBA/2 mice and SV40 transformed endothelial cells (SVEC) (Kim et al., *J. Immunol.*, 40:457-465, 1994) derived from C3H/HeJ mice. However, other types of cells, such as intestinal brush borders isolated from 10- to 14-day old suckling mice, which express sufficient number of FcRn can be also used. Alternatively, mammalian cells which express recombinant FcRn of a species of choice can be also utilized. After counting the radioactivity of the bound fraction of modified IgG or that of wild type, the bound molecules can be then extracted with the detergent, and the percent release per unit number of cells can be calculated and compared.

Affinity of modified IgGs or fragments thereof for FcRn can be measured by surface plasmon resonance (SPR) measurement using, for example, a BIAcore 2000 (BIAcore Inc.) as described previously (Popov et al., *Mol. Immunol.*, 33:493-502, 1996; Karlsson et al., *J. Immunol. Methods*, 145:229-240, 1991, both of which are incorporated by reference in their entireties). In this method, FcRn molecules are coupled to a BIAcore sensor chip (e.g., CM5 chip by Pharmacia) and the binding of modified IgG to the immobilized FcRn is measured at a certain flow rate to obtain sensorgrams using BIA evaluation 2.1 software, based on which on- and off-rates of the modified IgG, constant domains, or fragments thereof, to FcRn can be calculated.

Relative affinities of modified IgGs or fragments thereof, and the wild type IgG for FcRn can be also measured by a simple competition binding assay. Unlabeled modified IgG or wild type IgG is added in different amounts to the wells of a 96-well plate in which FcRn is immobilize. A constant amount of radio-labeled wild type IgG is then added to each well. Percent radioactivity of the bound fraction is plotted against the amount of unlabeled modified IgG or wild type IgG and the relative affinity of the modified IgG or fragments thereof can be calculated from the slope of the curve.

Furthermore, affinities of modified IgGs or fragments thereof, and the wild type IgG for FcRn can be also measured by a saturation study and the Scatchard analysis.

Transfer of modified IgG or fragments thereof across the cell by FcRn can be measured by in vitro transfer assay using radiolabeled IgG or fragments thereof and FcRn-expressing cells and comparing the radioactivity of the one side of the cell monolayer with that of the other side. Alternatively, such transfer can be measured in vivo by feeding 10- to 14-day old suckling mice with radiolabeled, modified IgG and periodically counting the radioactivity in blood samples which indicates the transfer of the IgG through the intestine to the circulation (or any other target tissue, e.g., the lungs). To test the dose-dependent inhibition of the IgG transfer through the gut, a mixture of radiolabeled and unlabeled IgG at certain ratio is given to the mice and the radioactivity of the plasma can be periodically measured (Kim et al., *Eur. J. Immunol.*, 24:2429-2434, 1994).

The half-life of modified IgG or fragments thereof can be measure by pharmacokinetic studies according to the methods provided herein (see, Examples section). Optionally or alternative pharmacokinetic studies may be performed as described by Kim et al. (*Eur. J. Immunol.* 24:542, 1994), which is incorporated by reference herein in its entirety. According to this method, radiolabeled modified IgG or fragments thereof is injected intravenously into mice and its plasma concentration is periodically measured as a function of time, for example, at 3 minutes to 72 hours after the injection. The clearance curve thus obtained should be biphasic, that is, α-phase and β-phase. For the determination of the in vivo half-life of the modified IgGs or fragments thereof, the clearance rate in β-phase is calculated and compared with that of the wild type IgG.

EXAMPLES

The present invention is illustrated by the following examples. It is to be understood that the particular examples, materials, amounts, and procedures are to be interpreted broadly in accordance with the scope and spirit of the invention as set forth herein.

Example I

Modulating pH Dependency of the Fc/FcRn Interaction in Half-Life Enhanced Antibodies The interaction between IgG Fc and the neonatal Fc receptor (FcRn) is fundamental to IgG homeostasis, and facilitates the long serum half-life of IgGs. FcRn and IgG bind in a highly pH-dependent manner which is crucial for IgG recycling. The Fc domain of IgG has been the target of numerous mutational studies aimed at altering IgG/FcRn affinity. These studies have yielded variants with disparate pharmacokinetic (PK) characteristics in vivo, ranging from highly extended half-lives to extremely fast clearance. In the current study, we isolate an Fc variant (N3E-YTE), harboring the YTE mutation (Dall'Acqua et al. (2002) J. Immunol. 169, 5171-5180) with >50 fold affinity enhancement at pH 6.0 compared to YTE and >200 fold compared to wild type IgG. This variant also has greatly enhanced pH 7.4 binding and exhibits extremely fast clearance in a human FcRn transgenic mouse model. Using N3E-YTE as a starting point, we generated additional phage libraries designed to enhance pH dependency, yet maintain increased pH 6.0 binding. Through the use of a phage ELISA to assess pH dependency, we were able to isolate variants with pH 6.0 affinities greater than that of YTE alone with enhanced in vivo half-lives in both a human transgenic FcRn mouse model and cynomolgus monkeys. Our work suggests a steep affinity threshold for FcRn binding that leads to extremely fast clearance at very high affinities, and switches precipitously to low clearance/enhanced half-lives at slightly lower affinities.

Introduction

Current approaches to optimize PK parameters by altering FcRn binding leverage the generally accepted model of FcRn mediated IgG homeostasis (Ghetie et al. (2000) Annu. Rev. Immunol. 18, 739-766; Roopenian et al. (2007) Nat. Rev. Immunol. 7, 715-725), which indicates that IgG molecules (internalized via fluid phase pinocytosis) bind to FcRn in the acidic endosome (pH 6.0) protecting them from degradation in lysosome. IgG salvaged by FcRn in the endosome then is returned to circulation and released to cell surfaces at neutral pH, maintaining the high serum IgG level. One of the main strategies employed to improve serum persistence of therapeutic antibodies is to engineer Fc variants with enhanced affinity for FcRn at acidic pH (Strohl (2009) Curr. Opin. Biotechnol. 20, 685-691). This approach has met with some notable successes, with some isolated variants exhibiting in vivo half-life improvements >3 fold higher than wild type antibodies (Dall'Acqua et al. (2006) J. Biol. Chem. 281, 23514-23524; Deng et al. (2010) Drug Metab. Dispos. 38, 600-605; Hinton et al. (2004) J. Biol. Chem. 279, 6213-6216; Hinton et al. (2006) J. Immunol.

176, 346-356; Yeung et al. (2009) J. Immunol. 182, 7663-7671; Zalevsky et al. (2010) Nat. Biotechnol. 28, 157-159; Yeung et al. (2010) Cancer Res. 70, 3269-3277).

One property considered important for half-life enhanced IgG molecules is maintained pH dependency. Improved pH 6.0 binding to FcRn while maintaining a minimal amount of pH 7.4 binding is considered essential to yield improved PK parameters (Presta (2008) Current Opinion in Immunology 20, 460-470). Studies on IgG and FcRn binding demonstrated that the pH dependent recycling mechanism is facilitated by His-Glu or His-Asp salt bridges between the IgG Fc and FcRn formed at pH ~6 (Kim et al. (1999) Eur. J. Immunol. 29, 2819-2825; Martin et al. (2001) Mol. Cell 7, 867-877). The imidazole side chain of histidine (with a pKa of ~6-6.5) has a net neutral charge at pH 7.4, but gains a positive charge in lower pH environments. The positively charged, protonated histidine species can make a salt bridge with negatively charged residues on the FcRn surface, and it is this interaction that is thought to facilitate endosomal binding and salvage. In the human IgG Fc, His310 and His435 form salt bridges with acidic side chains on FcRn and are integral to pH dependent binding (Kim et al. (1999) Eur. J. Immunol. 29, 2819-2825). The three main regions of IgG Fc that interact with FcRn are the His435 loop located in CH3, the His310 loop located in CH2, and the M252-T256 loop in CH2 (Martin et al. (2001) Mol. Cell 7, 867-877). These regions at the CH2-CH3 juncture are often targeted to attain variants with altered pharmacokinetic (PK) properties. While multiple variants with enhanced in vivo half-life have been generated via this strategy (Dall'Acqua et al. (2006) J. Biol. Chem. 281, 23514-23524; Deng et al. (2010) Drug Metab. Dispos. 38, 600-605; Hinton et al. (2004) J. Biol. Chem. 279, 6213-6216; Hinton et al. (2006) J. Immunol. 176, 346-356; Yeung et al. (2009) J. Immunol. 182, 7663-7671; Zalevsky et al. (2010) Nat. Biotechnol. 28, 157-159; Yeung et al. (2010) Cancer Res. 70, 3269-3277; Petkova et al. (2006) Int. Immunol. 18, 1759-1769), seemingly improved in vitro FcRn binding properties do not always yield in vivo pharmacokinetic enhancement (Datta-Mannan et al. (2007) Drug Metab. Dispos. 35, 86-94; Datta-Mannan et al. (2007) J. Biol. Chem. 282, 1709-1717). Additionally, in mice, little correlation between FcRn affinity and half-life has been observed (Gurbaxani et al. (2006) Mol. Immunol. 43, 1462-1473). Furthermore, IgG with increased FcRn binding at both pH 6.0 and 7.4 can actually exhibit shorter than wild-type serum half-life, and enhance endogenous IgG degradation (Abdegs) (Vaccaro et al. (2005) Nat. Biotechnol. 23, 1283-1288). These examples illustrate the complex relationship between FcRn affinity, pH dependency and in vivo clearance. Although it is generally understood that enhancing pH 6.0 binding while maintaining pH dependency can lead to half-life enhanced molecules, and enhancing pH 6.0 binding without pH dependency can lead to abdegs, the threshold affinities and parameters governing which outcome will be achieved by a particular variant are unknown.

To better understand the mechanism of pH binding dependency and the relationship between pH 6.0 FcRn binding affinity and IgG serum half-life we targeted the His 435 loop, by mutagenesis in an Fc base structure containing the YTE mutations (M252Y/S254T/T256E) (Dall'Acqua et al. (2002) J. Immunol. 169, 5171-5180; Dall'Acqua et al. (2006) J. Biol. Chem. 281, 23514-23524; Oganesyan et al. (2009) Mol. Immunol. 46, 1750-1755). Screening of the initial phage display library yielded an Fc variant (N3E-YTE) with ultra-high affinity for FcRn, but poor pH dependency. IgG carrying the mutations exhibited a reduced half-life in a human FcRn mouse model (Roopenian et al. (2003) J. Immunol. 170, 3528-3533) analogous to Abdeg mutations (Vaccaro et al. (2005) Nat. Biotechnol. 23, 1283-1288). Using this mutant as a starting point, we designed additional libraries to identify new variants with improved FcRn binding and maintained pH dependency. Variants identified from these libraries were constructed as IgGs and assessed for FcRn binding and pharmacokinetic parameters. Variants with 3-4 fold improved FcRn affinity versus YTE were characterized and found to have enhanced PK properties. The data also suggest an apparent pH 7.4 binding threshold for high affinity FcRn binders where less binding at this threshold can yield enhanced serum persistence, but tighter binding, yields molecules with extremely fast clearance.

Materials and Experimental Procedures

Reagents and Illustrations

All chemicals were of analytical grade. Restriction enzymes and DNA-modifying enzymes were purchased from New England Biolabs, Inc. (Beverly, Mass.). Oligonucleotides were purchased from Integrated DNA Technologies Inc. (Coralville, Iowa). All HB20.3 (anti-CD20) and motavizumab (anti-RSV F protein) (Wu at al. (2007) J. Mol. Biol. 368, 652-665) variants were generated at MedImmune. Recombinant human FcRn was expressed and purified as previously described (Dall'Acqua et al. (2002) J. Immunol. 169, 5171-5180). Antibodies are numbered according to the EU numbering convention (Kabat et al., *Sequences of Proteins of Immunological Interest*, 5$^{th}$ ed., 1991 NIH Pub. No. 91-3242). Sequence Logo (Schneider et al. (1990) Nucleic Acids Research 18, 6097-6100) figures were generated using Weblogo (weblogo.berkeley.edu; Crooks et al. (2004) Genome Research 14, 1188-1190).

Construction of Phage Libraries

DNA encoding IgG1 Fc (including YTE mutations in CH2) starting from E216 (Kabat numbering) to the Fc C-terminus was cloned as a g3 fusion into a phagemid vector. The initial insertion the library was constructed in His 435 loop region by introducing NNS codons at positions 432, 433, 434, 436, 437 and randomized 1 amino acid insertion after 437. A reverse primer containing NNS codons at these positions was employed in generating the library insert.

The library was generated by overlapping PCR (HiFi platinum PCR mix Invitrogen), and electroporated into TG1 *E. coli* cells (Stratagene) in a 2.5 kV field using 200 ohm resistance. Cells were recovered in 10 ml SOC medium for 30 minutes at 37° C. at 250 rpm and then plated on Q-trays with 2×YT agar containing carbenicillin and 2% glucose. The next day, colonies were collected by scraping them into 2×YT media containing 100 ug/ml carbenicillin and 2% glucose. Cells were grown until the OD was around 0.5-1. Approximately $10^{11}$ M13KO7 helper phage (Invitrogen) were introduced and incubated for 30 min at 37° C. without shaking and 30 min with shaking. Subsequently cells were centrifuged and resuspended in 50 ml of 2YT/carb/kanamycin (50 ug/ml)/0.5 mM IPTG and incubated at 30° C. at 250 rpm for 12-16 hrs. At the end of the incubation, phage were precipitated with PEG 6000 and resuspended in 3 ml of 20 mM MES pH 6.0 buffer. The CXXXXCE (SEQ ID NO:10) library was constructed using N3E-YTE as template for library generation. A degenerate primer was designed by randomizing position 433, 434, 435 and 436 with NNS codon. For the ZXXHXZ (SEQ ID NO:14) library, IgG1 Fc-YTE was used as template for library construction. A degenerate primers was designed by to maintain a fixed histidine at position 435 while randomizing positions 433, 434 and 436 with NNS. At positions 432 and 437 the degenerate codon STE was used to incorporate either histidine, glutamic acid, aspartic acid, or glutamine at these positions.

Panning of Initial IgG YTE/Fc Library

An ELISA based panning approached was utilized with biotinylated FcRn as the target. Briefly, 2 ug/ml biotinylated human FcRn and biotinylated mouse FcRn were coated into 8 wells (respectively) of a 96-well Maxisorp neutravidin immunoplate (Pierce) and stored overnight at 4° C. The plate was then blocked with 3% milk for 1 hr at room temperature. Wells were washed with 20 mM MES buffer (pH 6) before phage was added. 100 ml of phage ($6 \times 10^{12}$ PFU) in 20 mM MES buffer, pH 6.0 with 0.05% Tween 20 and 3% milk were added to each well. The plate was incubated 2 hr at 37° C. Wells were washed 20 times with 20 mM MES buffer, pH 6.0 with 0.05% Tween 20 and 0.3M NaCl. The bound phage were eluted by 100 ml PBS pH 7.4 for 30 min at 37° C. Eluted phage were used to reinfect the culture of exponentially growing TG1 cells. Infection was allowed at 37° C. for 30 min. Then the infected cells were plated on 2YT/carbenicillin/glucose plates. The next day, cells were scraped from the plates and infected with M13KO7 helper phage once again for the next round. Panning on mouse and human FcRn were done in parallel for a total of 4 rounds. CXXXXCE (SEQ ID NO:10) and ZXXHXZ (SEQ ID NO:14) libraries were screened in a similar manner (for 4 rounds each) except an additional pH 7.4 depletion step was employed after each round. After pH 7.4 Elution, phage were incubated for an additional hour in plates coated with biotinylated FcRn at pH 7.4 and unbound phage were collected.

pH Dependent Phage ELISA

Plates were coated with 2 mg/ml human FcRn at 4° C. overnight. Plates were then washed three times with 100 mM sodium phosphate buffer and blocked with 3% milk in either pH6 or pH7.4 sodium phosphate buffer at room temperature for 1 hour. Blocking buffer was removed and $10^9$ phage in either pH 6.0 or 7.4 sodium phosphate buffer were added to respective wells and incubated at RT. After an hour, plates were washed 3× with pH6 or pH 7.4 sodium phosphate buffer (+0.2% tween). Anti-M13 HRP (1:5000 RT 30 min) was then added and washed 3× prior to detection with TMB substrate.

Differential Scanning Calorimetry Analysis

DSC experiments were carried out using a Microcal VP-DSC scanning microcalorimeter (Microcal). All solutions and samples used for DSC were filtered using a 0.22 μm filter prior to loading into the calorimeter. Antibodies used for the DSC studies were >98% monomeric as determined by analytical SEC. Prior to DSC analysis all samples were exhaustively dialyzed in reference buffer (PBS) for subsequent DSC experiments. Baseline measurements (buffer-versus-buffer) were obtained to be subtracted from the sample measurement. Dialyzed samples (at a concentration of 1 mg/mL) were added to the sample well and DSC measurements were performed at a 1° C./min scan rate. Data analysis and deconvolution were carried out using the Origin™ DSC software provided by Microcal. Deconvolution analysis was performed using a non-two-state model and best fits were obtained using 100 iteration cycles.

Surface Plasmon Resonance (SPR) Measurements

The interaction of soluble human FcRn with immobilized antibody variants was monitored by surface plasmon resonance with a ProteOn™ XPR36 (Bio-Rad, Hercules, Calif.) (Bravman et al. (2006) Analytical Biochemistry 358, 281-288). Antibodies were first coupled to a GLC sensor chip using a ProteOn™ Amine Coupling Kit according to the manufacturer's instructions. Excess reactive esters were blocked with a 6-min injection of 1 M ethanolamine. Antibodies were immobilized at a surface density between of >5000 RUs for equilibrium measurements and <200 RUs for kinetic binding experiments. Human FcRn was used at concentrations ranging from 0.45 nM to 3 μM at a flow rate of 25 μL/min for steady state measurements and 75 μL/min for kinetic measurements. One channel was always left unmodified to provide a blank reference surface. Dilutions and binding experiments were carried out at 25° C. in phosphate buffered saline (PBS) pH 6.0 or pH 7.4, containing 0.05% Tween 20. Steady-state binding data were collected for 10 min. Antibody surfaces were regenerated with a 15 sec injection of 5 mM HCl. Human FcRn was also allowed to flow over the reference channel which served as a blank to subtract from the antibody coated channels. Binding affinities were determined by using the ProteOn™ Manager software (BioRad). Dissociation constants ($K_d$s) were determined by fitting the corresponding binding isotherms for steady state data or by fitting the kinetics for association and dissociation employing a 1:1 Langmuir or a 1:1 Langmuir Mass Transfer model.

HFcRn Transgenic Mice and Pharmacokinetic Analyses

HFcRn transgenic mice used in this study are the F1 cross of mFcRn deficient B6.129X1-Fcgrt$^{tm1Dcr}$/DcrJ and hFcRn cDNA transgenic line B6.Cg-Fcgrt$^{tm1Dcr}$ Tg(CAG-FCGRT) 276Dcr/DcrJ (Roopenian et al. (2003) J. Immunol. 170, 3528-3533; Chaudhury et al. (2003) The Journal of Experimental Medicine 197, 315-322). Expression of hFcRn in these animals has been validated by reverse transcription (RT)-PCR, western blot and functional assays in vivo (Chaudhury et al. (2003) The Journal of Experimental Medicine 197, 315-322).

Sex matched (6- to 16-weeks old) HFcRn mice were given a bolus IV dose of 2.5 mg/kg antibody on day 0. Eight hFcRn Tg mice were used per antibody, with 4 mice (A group or B group) bled at alternate timepoints. Blood samples were obtained from the retro-orbital plexus using capillary pipettes at different timepoints throughout the 3 week study. A quantitative ELISA was used to monitor the serum concentrations of the antibodies. Briefly, 96-well plates were coated with 2 μg ml$^{-1}$ of AffiPure Goat anti-human f(ab)2 fragment specific (Jackson Immunoresearch). Plates were blocked with 3% BSA in PBS for an hour, and then incubated with appropriately diluted serum samples (1:200 for earlier time points and 1:50 or 1:100 for later timepoints). Goat anti-human Fd-specific HRP conjugated antibody (Southern Biotechnology Associates, Inc.) was used to detect the human antibody (dilution 1:10000). Absorbance at 405 nm was measured after development with TMB substrate (KPL Inc.) according to manufacturer's directions. Standard curves (starting at 10 ug/ml) were generated for each antibody variant diluted into 1:100 pre-bleed mouse serum (taken day −3). The linear portions of standard curves generated in Prizm (GraphPad Software, Inc.) were then used to quantify human IgG in the serum samples.

Pharmacokinetic Analyses in Cynomolgus Monkey

Sixteen female cynomolgus monkeys were randomized and assigned to one of 3 study groups. Each animal received one intravenous (i.v.) dose of Motavizumab, Motavizumab-YTE, Motavizumab-N3 or Motavizumab Y31-YTE at 10 mg/kg. Blood samples were drawn prior to dosing on day 0, at 1, 4, and 12 hours after dosing and at), Days 2, 3, 4, 8, 15, 22, 29, 43, 57, 71 and 85 after dosing. The serum concentrations of Motavizumab antibodies were determined using the anti-Motavizumab ELISA as described previously (Dall'Acqua et al. (2006) J. Biol. Chem. 281, 23514-23524) with a separate standard curve generated for each variant tested. For each i.v. infusion, a non-compartmental model was fitted for the serum concentration data of each animal using SAS 8.0 (SAS Institute, Cary, N.C.). Descriptive statistics for several pharmacokinetics parameters were then calculated.

Results

Identification of Binding Improved Fc Variants from an YTE Variant Library

Previous results have demonstrated amino acid mutations made in the Fc region of IgG that improve FcRn binding at pH 6.0, such as YTE, can greatly increase antibody serum half-life in experimental animals, including cynomolgus monkey (Dall'Acqua et al. (2006) J. Biol. Chem. 281, 23514-23524; Zalevsky et al. (2010) Nat. Biotechnol. 28, 157-159). However, the combination of YTE with additional mutations in the H435 loop (H433K/N434F) that enhance FcRn binding at both acidic and neutral pH resulted in Abdeg molecules with severely reduced serum half-life (Vaccaro et al. (2005) Nat. Biotechnol. 23, 1283-1288; Montoyo et al. (2009) Proc. Natl. Acad. Sci. U.S.A. 106, 2788-2793). YTE mutations maintains low FcRn binding at pH 7.4 as does wild type IgG (Dall'Acqua et al. (2002) J. Immunol. 169, 5171-5180), whereas Abdegs have increased FcRn binding at both acidic and neutral pH. To identify novel high affinity FcRn binding variants, we targeted amino acids in one of the key FcRn binding sites containing histidine 435 in Fc region of an IgG, and constructed a library of variants containing randomized sequences between amino acids 432-437 of CH3 leaving the 435 Histidine unchanged. Additionally, an extra random amino acid codon was inserted after position 437, (437*) to determine if additional FcRn binding contacts in the Fc fragment carrying YTE mutations would prove beneficial. The variant Fc library was then displayed on the M13 phage surface and FcRn binding variants were selected against recombinant human FcRn protein coated in ELISA wells in pH 6.0 buffer. Sequence analysis of panning outcomes revealed a unique group of variants containing cysteines at 432 and 437 positions. One variant, N3E-YTE (Table 1) and its derivatives were then converted to HB20.3 anti-CD20 IgG background. SPR binding analysis showed that an IgG carrying the double cysteine variant, e.g., N3E-YTE, improved FcRn binding greater than 50-fold over the YTE variant at pH 6.0 (Table 1). However, the pH 7.4 binding of the variant to FcRn also increased significantly, resulting in poor pH binding dependency.

TABLE 1

Human FcRn binding to various HB20.3 IgGs including CXXXXCE (SEQ ID NO: 10) and ZXXHXZ (SEQ ID NO: 14) library variants

| Clone | Sequence (432-437)[a] | SEQ ID NO: | YTE base structure | Human FcRn pH 6.0 KD[b] (nM) | Human FcRn pH 7.4 KD[b] (nM) | |
|---|---|---|---|---|---|---|
| Wt HB20.3 | LHNHYT | 8 | No | 880 | N.B. | Anti-CD20 IgG1 (HB20.3) |
| YTE | LHNHYT | 8 | Yes | 215 | 5800 | (M252Y, S254T, T256E) (Dall'Acqua et al. (2002) J. Immunol. 169, 5171-5180) |
| N3E-YTE | CSWHLCE[c] | 16 | Yes | 3.7 | 41 | Original construct identified from phage panning (contains glutamic acid insertion after residue 437) |
| N3-YTE | CSWHLC | 20 | Yes | 24 | 353 | Glutamic acid insertion removed from N3E-YTE |
| N3E | CSWHLCE | 16 | No | 41 | 855 | Glutamic acid insertion, no YTE |
| N3 | CSWHLC | 20 | No | 124 | 2000 | "N3" construct, no insertion, no YTE |
| SerN3-YTE | SSWHLS | 30 | Yes | 106 | 514 | N3-YTE with 432 and 437 cysteines replaced with serine |
| CwtC-YTE | CHNHYC | 31 | Yes | 367 | 7700 | L432C, T437C, YTE |
| YC33-YTE | CRRHLCE | 32 | Yes | 276 | 17500 | CXXXXCE Library |
| YC83-YTE | CRRHICE | 33 | Yes | 160 | 6650 | CXXXXCE Library |
| YC37-YTE | CSRHRCE | 34 | Yes | 225 | 10,000 | CXXXXCE Library |
| YC56-YTE | CRRHSCE | 35 | Yes | 364 | 30500 | CXXXXCE Library |
| YC59-YTE | CNRHRCE | 36 | Yes | 737 | 14400 | CXXXXCE Library |
| Y3-YTE | ERYHTQ | 26 | Yes | 36 | 2600 | ZXXHXZ library |
| Y31-YTE | ERFHRQ | 25 | Yes | 57 | 4700 | ZXXHXZ library |
| Y12-YTE | EAWHRQ | 27 | Yes | 34 | 7000 | ZXXHXZ library |
| Y83-YTE | EPYHRE | 37 | Yes | 120 | 14800 | ZXXHXZ library |
| Y53-YTE | ERSHRQ | 38 | Yes | 68 | 5500 | ZXXHXZ library |
| Y43-YTE | EPHHRQ | 39 | Yes | 152 | 13500 | ZXXHXZ library |
| Y34-YTE | HTHHRQ | 40 | Yes | 187 | 27400 | ZXXHXZ library |
| Y39-YTE | EPWHYQ | 41 | Yes | 25.4 | 947 | ZXXHXZ library |
| Y37-YTE | HRFHLQ | 28 | Yes | 179 | 1520 | ZXXHXZ library |
| Y38-YTE | EQFHRQ | 42 | Yes | 152 | 16500 | ZXXHXZ library |
| Y19-YTE | HHFHMQ | 43 | Yes | 170 | 1190 | ZXXHXZ library |
| Y6-YTE | QKYHNQ | 44 | Yes | 237 | 1880 | ZXXHXZ library |
| Y54-YTE | HRHHRQ | 45 | Yes | 165 | 566 | ZXXHXZ library |
| Y7-YTE | ELWHRQ | 46 | Yes | 141 | 1770 | ZXXHXZ library |
| Y56-YTE | ERHHRQ | 47 | Yes | 150 | 1110 | ZXXHXZ library |
| Y30-YTE | EPWHRE | 48 | Yes | 96 | 1220 | ZXXHXZ library |
| Y74-YTE | HRFHHQ | 49 | Yes | 190 | 670 | ZXXHXZ library |
| Y8-YTE | EAYHHQ | 50 | Yes | 197 | 250 | ZXXHXZ library |
| Y2-YTE | EQYHHQ | 51 | Yes | 92 | 1000 | ZXXHXZ library |
| Y38-YTE | EQFHRQ | 42 | Yes | 137 | 1010 | ZXXHXZ library |
| Y4-YTE | EPHHNQ | 52 | Yes | 203 | 1420 | ZXXHXZ library |
| Y14-YTE | ERYHHH | 53 | Yes | 259 | 1700 | ZXXHXZ library |
| Y45-YTE | ERYHNQ | 54 | Yes | 124 | 1260 | ZXXHXZ library |
| Y1-YTE | ETFHGH | 55 | Yes | 534 | 6000 | ZXXHXZ library |
| Y9-YTE | EAFHRE | 29 | Yes | 112 | 1900 | ZXXHXZ library |

TABLE 1-continued

Human FcRn binding to various HB20.3 IgGs including CXXXXCE (SEQ ID NO: 10) and ZXXHXZ (SEQ ID NO: 14) library variants

| Clone | Sequence (432-437)[a] | SEQ ID NO: | YTE base structure | Human FcRn pH 6.0 KD[b] (nM) | Human FcRn pH 7.4 KD[b] (nM) | |
|---|---|---|---|---|---|---|
| Y3 | ERYHTQ | 26 | No | 267 | 1700 | Y3 without YTE |
| Y2 | EQYHHQ | 51 | No | 200 | 2330 | Y2 without YTE |
| Y31 | ERFHRQ | 25 | No | 491 | N.B. | Y31 without YTE |
| Y12 | EAWHRQ | 27 | No | 254 | N.B. | Y12 without YTE |

[a]Residue numbering is according to Kabat et al. (*Sequences of Proteins of Immunological Interest*, 5th ed., 1991 NIH Pub. No. 91-3242)
[b]Steady state affinity measurements carried out by PROTEON as described under Experimental Procedures. Values in Italics were determined via Kinetic model (Langmuir with mass transfer)
[c]Bold indicates insertion after residue 437 (referred to herein as 437*)

We further dissected N3E-YTE mutation to understand which mutations contributed to FcRn binding. Removing the glutamic acid insertion residue 437* (N3-YTE). had a modest impact on pH 6.0 and pH 7.4 binding, suggesting the sequence variation from 432-437 are sufficient to confer the majority of the observed binding improvements. To assess the role of the cysteines at 432 and 437, they were replaced with serines (SerN3-YTE). The resultant variant showed reduced FcRn binding at both pH 6.0 and pH 7.4, suggesting disulfide bound between the Cysteine may form and contribute positively to the binding. An additional variant (CwtC-YTE) with wild type residues between L432C, T437C was generated to determine what role the cysteines alone had on FcRn binding. This construct bound to FcRn slightly less than the parent YTE construct indicating the cysteine mutations alone, do not confer enhanced binding. Our observation that the pH binding dependency of YTE can be altered by mutations at H435 loop is in agreement with previous studies (Dall'Acqua et al. (2002) J. Immunol. 169, 5171-5180; Vaccaro et al. (2005) Nat. Biotechnol. 23, 1283-1288) and supports the role of H435 and its loop in pH dependent binding of Fc to FcRn. In addition to separately removing the glutamic acid insertion (N3-YTE) and YTE mutations (N3E) from N3E-YTE, we also generated a construct with both removed (N3). N3 had improved pH dependency compared to N3E-YTE (Table 1).

L432C, T437C Stabilize the $C_H3$ Domain

Figure 3:
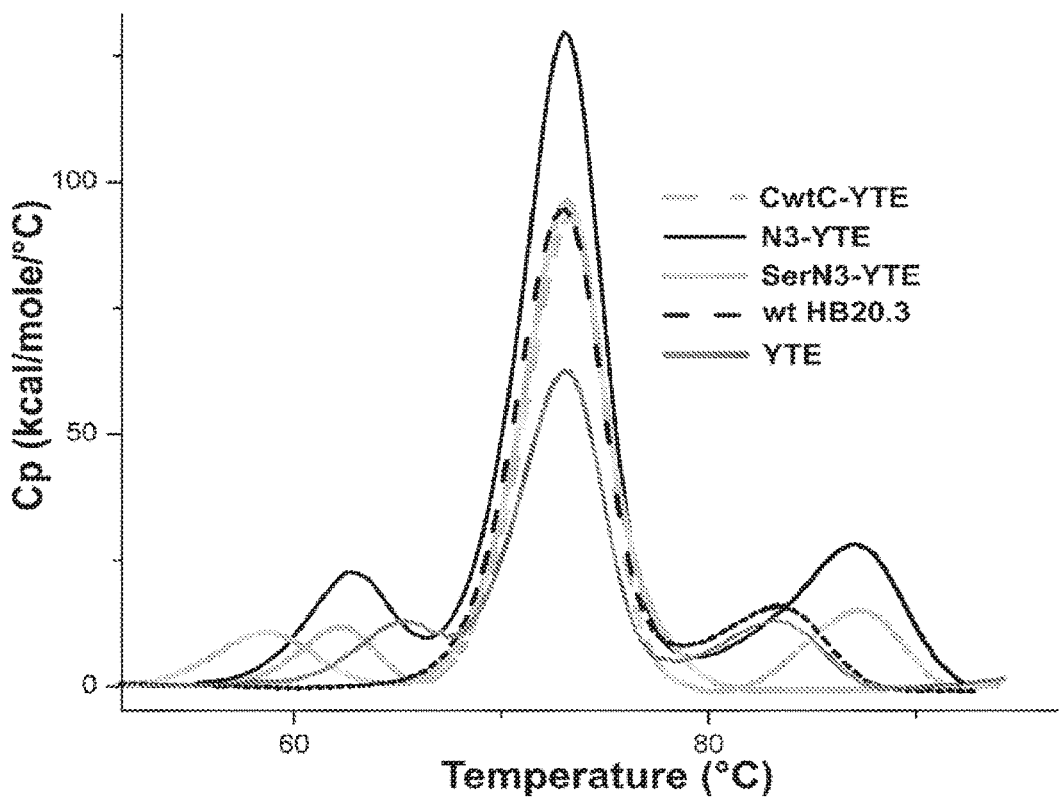
FIG. 3 shows differential scanning calorimetry (DSC) analysis of HB20.3 IgG and various Fc variants. All antibodies exhibit a Fab unfolding temperature of ~73° C. HB20.3 (black dashed line) has a $C_H3$ $T_m$ of 83.3° C.; the denaturation transition for HB20.3 $C_H2$ (normally ~69° C.) is likely buried within the Fab transition. YTE (dark grey line) has a $C_H3$ $T_m$ of 83.3° C. and a $C_H2$ of 65.1° C. N3-YTE (black line), and CwtC-YTE (light grey dashed line) exhibit similar $C_H2$ and $C_H3$ transitions, with the $C_H3$ $T_m$ at 87.1° C. for both variants and $C_H2$ transition reduced to 62.7° C. for N3-YTE and 62.3° C. for CwtC-YTE. SerN3-YTE (light grey line) had the lowest $C_H2$ transition of the antibodies shown at 58.7° C., with its $C_H3$ transition masked by the Fab unfolding at 73° C.

Cα distances and side chain orientation of L432 and T437 in Fc X-ray structures seem to be compatible with disulfide bond formation upon mutation to cysteines. Using the crystal structure of YTE-Fc (Oganesyan et al. (2009) Mol. Immunol. 46, 1750-1755) we determined the Cα distances between L432 and T437 to be 6.7 Å. This distance is within the observed Cα distance range (~4.6-7 Å) for cystines that has been reported based on analysis of multiple crystal structures (Petersen et al. (1999) Protein Engineering 12, 535-548). As the stabilizing effects of disulfide bond formation within proteins are well known, we performed differential scanning calorimetry (DSC) to examine whether the $C_H3$ domain is stabilized in variants containing L432C/T437C (FIG. 3). The DSC profile of HB20.3 consists of $C_H3$ $T_m$ of 83.3° C. with the Fab and $C_H2$ domains both unfolding as one peak at 73° C. YTE HB20.3, has nearly identical Fab and $C_H3$ unfolding as wild type, but with a slightly lower $C_H2$ $T_m$ at 65.1° C. CwtC-YTE (L432C/T437C with the YTE mutation) has a $C_H3$ $T_m$ at 87.1° C., nearly 4° C. higher than wild type $C_H3$. Interestingly, while $C_H3$ is stabilized greatly, $C_H2$ $T_m$ is reduced ~3° C. compared to YTE-HB20.3. Comparison of N3-YTE and SerN3-YTE (constructs that differ in having either cysteines or serines at 432 and 437) further illustrates the profound stabilization effect caused by L432C/T437C. SerN3-YTE lowest $T_m$ is 58.7° C. with $C_H3$ $T_m$ well below 80° C., whereas the DSC profile of N3-YTE nearly matches that of CwtC-YTE, with elevated $C_H3$ $T_m$ of 87.1° C.

Engineer and Select pH Binding Dependent YTE Variants

Figure 4A:
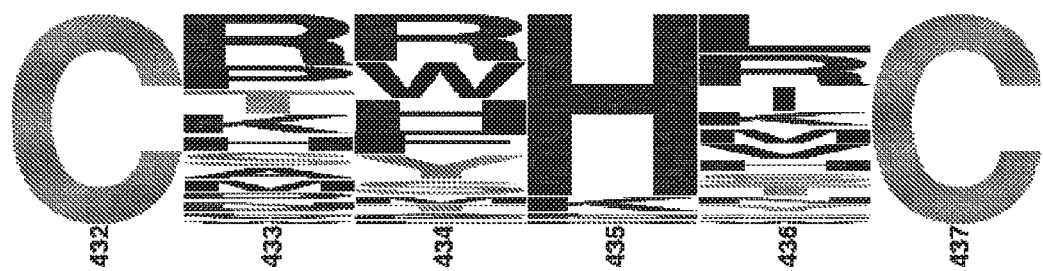
FIGS. 4A-C show sequence analysis for the CXXXXCE (SEQ ID NO:10) and ZXXHXZ (SEQ ID NO:14) libraries as graphic representations of the relative incidence of an amino acid to occur at a particular position in the represented position across all the sequences surveyed. The larger the letter the more frequently that amino acid is found in that position across the examined sequences.
Figure 4B:

We designed new libraries at the His435 loop with the goal of yielding variants with reduced pH 7.4 binding while maintaining high affinity binding at pH 6.0. We also modified our phage selection conditions to allow more stringent selection of pH dependent, high affinity FcRn binder in panning. We generated a library based on N3E-YTE by randomizing the intervening sequences in between Cys432 and Cys437 including H435 (CXXXXCE (SEQ ID NO:10) Library). To discouraging binding at neutral pH, a pH 7.4 depletion step was introduced after the pH 6.0 elution step. Unbound phage were then used to infect bacteria for amplification and characterization. A phage ELISA was also developed to characterize binding of clones following the pH dependent panning. In this assay, clonal phage were used to bind to coated FcRn wells under either pH 6.0 and 7.4 conditions. Binding at pH 6.0 and the binding ratio between pH 6.0 and 7.4 were compared to the parental N3E-YTE and YTE harboring phage. Phage clones selected after 4 rounds of panning were screened for pH binding dependency in the ELISA. While almost all showed expected high binding to FcRn similar or better than YTE control at pH 6.0 in the assay, several clones showed significantly reduced binding at pH 7.4, or higher pH 6.0 to 7.4 binding ratio, indicating improved pH binding dependency vs. N3E-YTE. Sequence analysis of over 56 clones isolated after 4 rounds of panning showed His435 was highly enriched (FIG. 4A). Most round 5 clones contained H435, confirming the key role of Histidine at this position in FcRn binding. Sequence analysis shows these clones also contained positively charged residues at 433, 434 or 436. A subset of round 4 clones with improved pH 6/7.4 binding ratios via phage ELISA were even further enriched for positively charged residues adjacent to 435 (FIG. 4B).

Figure 4C:
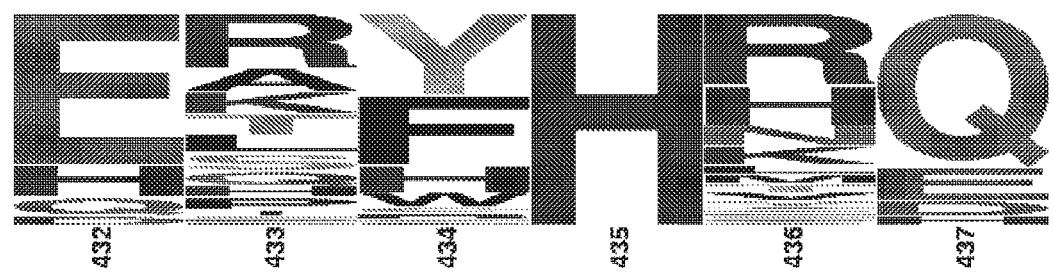

An additional library was designed to replace the cysteine residues at positions 432 and 437 with charged residues including histidine. As Cys432 and Cys437 are likely forming disulfide bonds in N3E-YTE, we reasoned that replacing the rigid cysteine loop constrain in N3E-YTE with the charged amino acids at the cysteine positions may introduce pH dependent changes in the loop position that could be beneficial to pH dependent FcRn binding. To test the hypothesis, we designed a library replacing Cys432 and Cys437 with Glutamic acid (E), Aspartic acid (D) Histidine (H) and random amino acids at position 433, 434 and 436 while leaving H435 unchanged (ZXXHXZ (SEQ ID NO:14) library). In this scheme, "Z" can be glutamic acid, aspartic acid, histidine, or glutamine. Glutamic acid (E), Aspartic acid (D) or Histidine (H) were introduced at 432 and 437 to allow for the potential formation of a pH dependent salt-bridge between Glutamic acid or Aspartic acid and Histidine or the introduction of negatively charged residues that may be sensitive to local electrostatic changes. Glutamine (Q) was also encoded at these positions 432 and 437 due to the use of degenerate oligonucleotides in cloning. The ZXXHXZ (SEQ ID NO:14) library was subjected 4 rounds of panning with the additional pH 7.4 binding depletion step following each panning elution. Individual phage clones following the 4 rounds of panning were sequenced as well as subjected binding screen in the phage ELISA, as described for CXXXXCE (SEQ ID NO:10) library panning and screen. Unlike the CXXXXCE (SEQ ID NO:10) library results, the majority of the clones selected from the ZXXHXZ (SEQ ID NO:14) library exhibited improved pH binding dependency compared to N3E-YTE, demonstrated by the high ratio of pH 6.0 vs pH 7.4 binding in the phage ELISA. Furthermore, a sequence pattern was revealed in the clones identified as pH dependent by phage ELISA (FIG. 4C). The pH dependency was subsequently confirmed by SPR analysis when converted to IgG (Table 1). The results showed that positively charged amino acids, (usually arginine), are preferable at position 433 and 436; and hydrophobic amino acids, tyrosine, or phenylalanine, are preferable at position 434 in the clones that acquired high affinity, pH dependent binding to FcRn. Intriguingly, the pH dependent binding clones from this library were highly enriched for Glutamic acid (E) and Glutamine (Q) encoded at position 432 and 437, respectively. The results indicated that engineering of surface charge potential near H435 are effective to identify high affinity and pH dependent FcRn binding Fc variants. Adaptation of a balanced charging surface near H435 appears beneficial for FcRn binding, despite a lack of histidine residues in these positions which may have been susceptible to pH dependent changes.

SPR Binding Characterization of FcRn Binding Variants as IgG.

A panel of variants from the CXXXXCE (SEQ ID NO:10) and ZXXHXZ (SEQ ID NO:14) libraries that showed pH binding dependency in phage screens were selected and expressed as IgG1 (HB20.3, anti-CD20) for further characterizations. Surface Plasmon Resonance (SPR) was used to measure binding of purified mAbs to Human FcRn at both pH 6.0 and pH 7.4. Table 1 summarizes sequences and the binding results of the selected mAbs. The pH 7.4 binding of all tested variants derived from either CXXXXCE (SEQ ID NO:10) or ZXXHXZ (SEQ ID NO:14) library showed expected reduced binding to FcRn comparing to N3E-YTE, and with many binding levels similar to YTE IgG (approximate 5 µM). CXXXXCE (SEQ ID NO:10) variants showing pH dependency in phage ELISA maintained pH dependent binding as IgGs however, these variants did not exhibit improved affinity compared to YTE at pH 6. Many ZXXHXZ (SEQ ID NO:14) variants did show significant pH 6.0 affinity improvements versus YTE while also maintaining pH dependent binding. Multiple variants, e.g., Y3-YTE, Y12-YTE and Y31-YTE, showed 3-9 fold higher binding affinity for FcRn at pH 6.0 than YTE while binding at pH 7.4 remains similar or weaker than the benchmark. These results confirm the effectiveness of the library and panning strategy used to select and identify the clones.

Figure 5A:
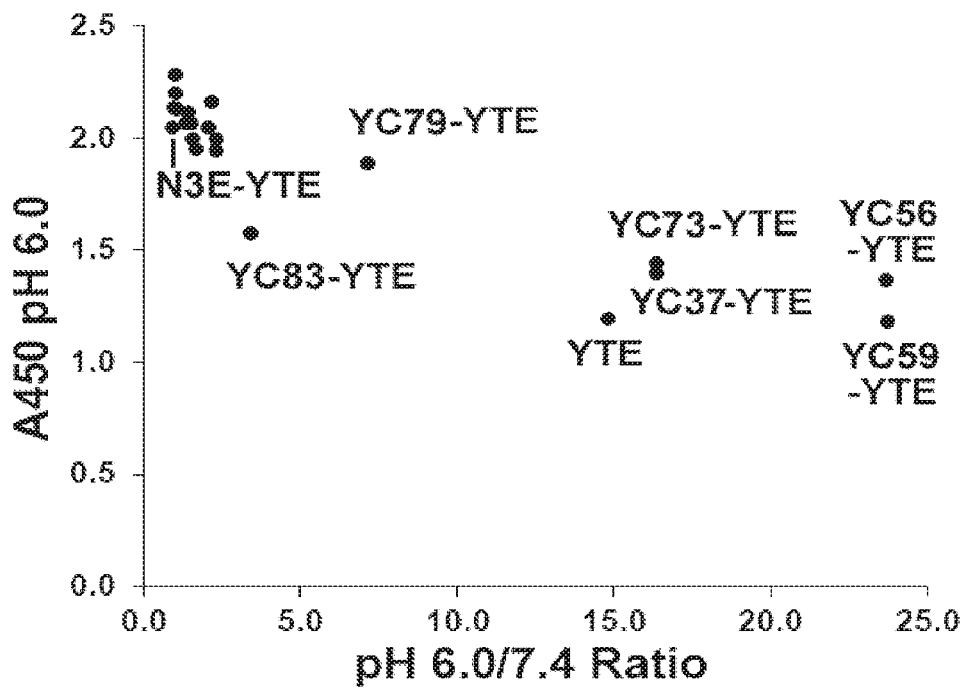
FIGS. 5A and B show phage ELISA data for the CXXXXCE (SEQ ID NO:10) and ZXXHXZ (SEQ ID NO:14) libraries.
Figure 5B:
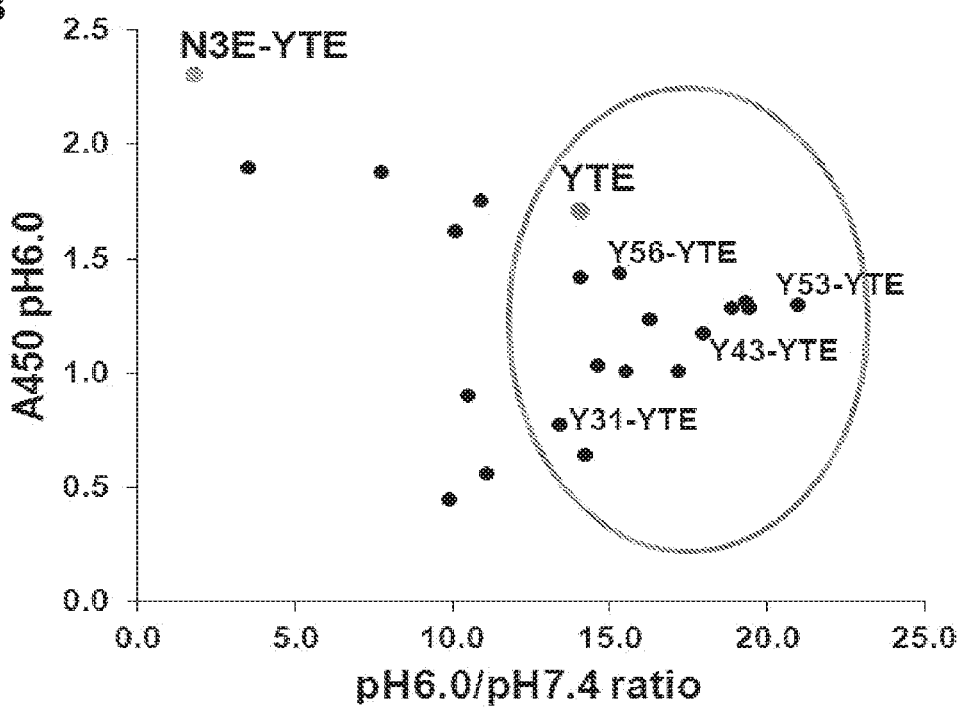
FIG. 5B shows representative phage ELISA results for individual clones isolated after round 4 of panning for the ZXXHXZ (SEQ ID NO:14) library. Phage clones exhibiting pH dependent binding in a preferred region are circled. Some of these clones were converted to full length IgG and reassessed for FcRn binding.

The pH 6.0 and 7.4 binding affinity of CXXXXCE (SEQ ID NO:10) and ZXXHXZ (SEQ ID NO:14) clones as well as N3E-YTE variants and derivatives were grouped into quadrants (FIG. 5A, 5B, 5C). Quadrant I contains variants with high pH 6.0 binding and low pH 7.4 binding likely exhibiting "YTE-like" properties. Quadrant II contains clones with low pH 6.0 and pH 7.4 binding likely exhibiting "wild type-like" properties. Quadrant III contains antibodies with high pH 6.0 and 7.4 binding likely exhibiting "Abdeg-like" properties. Quadrant IV contains high pH 7.4 and low pH 6.0 binders, none of which were isolated in these studies.

FcRn Binding in an Additional IgG Background: Motavizumab

A small number of clones found to have desirable FcRn binding properties in the anti-CD20 IgG1 background were moved to an additional IgG1 background, motavizumab (Wu at al. (2007) J. Mol. Biol. 368, 652-665), to confirm the clones FcRn binding characteristics in the context of different variable domains. As previous studies have shown that variable domains can contribute to FcRn binding variability in wt Fc backgrounds (Suzuki et al. (2010) J. Immunol. 184, 1968-1976; Wang et al. (2011) Drug Metab. Dispos. 39, 1469-1477; Datta-Mannan et al. (2012) Drug Metab. Dispos. 40, 1545-1555), we wanted to confirm that the FcRn binding properties of our variants were transferable. ZXXHXZ (SEQ ID NO:14) library clones Y12-YTE, Y31-YTE and Y3-YTE were generated as IgGs with Motavizumab variable domains. The pH 6.0 binding of these clones as well as YTE and N3E-YTE, are consistent with those in the anti-CD20 background (Table 2). Interestingly, pH 7.4 binding varies when clones were shifted to different antibody variable domains with either increased binding (Y31-YTE) or decreased binding (YTE). Additionally, for Y12-YTE and Y31-YTE, clones were also generated in the wild type Mota Fc background (lacking YTE) e.g. Y12 and Y31. These constructs were generated to show the contribution the H435 loop mutations alone made to FcRn binding. Y12 and Y31 did maintained enhanced FcRn binding at pH 6.0 and pH dependency (low binding at pH 7.4). These data indicate that YTE and the H435 mutations such as Y12 and Y31 have an additive effect on pH dependent binding. N3 with pH 6.0 KD of 89 nM and a pH 7.4 KD of 1630 nM had similar binding in the motavizumab background as in the anti-CD20 background.

TABLE 2A

FcRn binding to various Motavizumab IgGs

| Clone | Sequence from Residue 432-437 (insertion residue in BOLD) | SEQ ID NO: | YTE? | Human FcRn(nM) | | Cyno FcRn (nM) | |
| --- | --- | --- | --- | --- | --- | --- | --- |
| | | | | pH 6.0 Kd | pH 7.4 Kd | pH 6.0 Kd | pH 7.4 Kd |
| Wildtype Motavizumab | LHNHYT | 8 | No | 2140 | N.B. | 1920 | >10000 |
| YTE | LHNHYT | 8 | Yes | 314 | 10000 | 275 | 8000 |
| N3E-YTE | CSWHLCE | 16 | Yes | 3.4 | 24.6 | 3.9 | 37 |
| N3E | CSWHLCE | 16 | No | 41 | 865 | 37.9 | 685 |

TABLE 2A-continued

FcRn binding to various Motavizumab IgGs

| Clone | Sequence from Residue 432-437 (insertion residue in BOLD) | SEQ ID NO: | YTE? | Human FcRn(nM) pH 6.0 Kd | Human FcRn(nM) pH 7.4 Kd | Cyno FcRn (nM) pH 6.0 Kd | Cyno FcRn (nM) pH 7.4 Kd |
|---|---|---|---|---|---|---|---|
| N3 | CSWHLC | 20 | No | 89 | 1630 | 76.4 | 1240 |
| Y3-YTE | ERYHTQ | 26 | Yes | 53 | 2710 | 44 | 7000 |
| Y31-YTE | ERFHRQ | 25 | Yes | 84 | 1150 | 76 | 1190 |
| Y12-YTE | EAWHRQ | 27 | Yes | 86 | 5040 | 89.5 | >10000 |
| Y31 | ERFHRQ | 25 | No | 491 | N.B. | 567 | >10000 |
| Y12 | EAWHRQ | 27 | No | 254 | N.B. | 312 | >10000 |

TABLE 2B

Effector binding to various Motavizumab IgGs values nM

| Clone | Fcγ IIIa (158V) | Fcγ IIIa (158F) | Fcγ IIa | Fcγ IIb | Fcγ RIa | C1q |
|---|---|---|---|---|---|---|
| Wildtype Motavizumab | 146 | 4140 | 506 | 782 | 45.8 | 328 |
| YTE | 245 | 6060 | 1280 | 1950 | 39.2 | 482 |
| N3E-YTE | 803 | 17300 | 2780 | 3420 | 47 | 123 |
| N3E | 608 | N.B. | 2060 | 2540 | 61.2 | 324 |
| N3 | 144 | 5340 | 622 | 950 | 43.7 | 165 |
| Y3-YTE | 4460 | 10600 | 4080 | 7000 | 280 | 230 |
| Y31-YTE | 814 | N.B. | 2110 | 2890 | 65.6 | 381 |
| Y12-YTE | N.B. | N.B. | N.B. | N.B. | 80.8 | 832 |
| Y31 | 311 | N.B. | 863 | 1490 | 55.8 | 267 |
| Y12 | 1030 | N.B. | 5070 | N.B. | 51 | 512 |

TABLE 2C

DSC and hFcRn transgenic mouse pharmacokinetic data

| Clone | DSC Tm1 (° C.) | HuFcRn transgenic mouse PK data: Dose (mg/kg) | Half-life day | AUCinf ug * day/mL | CL mL/day * kg |
|---|---|---|---|---|---|
| *Wildtype Motavizumab* | 69 | 2.5 | 0.73 | 41.67 | 60.03 |
| *YTE* | 63.9 | 2.5 | 3.61 | 108.73 | 23.01 |
| *N3E-YTE* | 53.3 | 2.5 | 0.78 | 6.7 | 373.2 |
| *N3E* | 63 | 2.5 | 2.16 | 75 | 33.3 |
| N3 | 64.6 | 2.5 | 5.66 | 99 | 25.2 |
| Y3-YTE | 51 | 2.5 | 2.07 | 94.6 | 26.4 |
| Y31-YTE | 53 | 2.5 | 3.65 | 105 | 23.8 |
| Y12-YTE | 51 | 2.5 | 2.75 | 96.6 | 26.4 |
| Y31 | 55.6 | 2.5 | 2.99 | 67 | 37.5 |
| Y12 | 53.8 | 2.5 | 2.43 | 71 | 35.1 |

Serum Clearance in a Human FcRn Transgenic Mouse Model

Next, we examined the serum clearance of various pH sensitive, FcRn binding variants using the human FcRn transgenic mice (Roopenian et al. (2003) J. Immunol. 170, 3528-3533; Chaudhury et al. (2003) The Journal of Experimental Medicine 197, 315-322). In the PK studies, hFcRn Tg mice were given 2.5 mg/kg bolus IV dose at time zero, and the blood were drawn at varies time points ranging from 30 min to 21 days post antibody injection. The human antibody concentration in the mouse serum was quantified by ELISA.

Table 2 summarized the PK results, lowest DSC Tm as well as the sequence and binding properties of Motavizumab and its Fc variants. Serum concentration-time profiles of selected antibodies are presented (FIG. 6A). As expected, YTE mutation reduced the serum clearance by approximately 2.4 fold compared to the Motavizumab. YTE consistently confers low antibody clearance rates in the hFcRn Tg mice model, suggesting this variant satisfies the conditions necessary and sufficient for enhanced recycling through FcRn binding. N3E-YTE, the variant with high affinity pH 6.0 binding but lack of pH binding dependency, showed an extreme fast serum clearance of 373 ml/day/kg, about six times faster than Motavizumab, reiterating the importance of the pH dependent binding in FcRn mediated antibody recycling. Clone Y31-YTE also shows about 2.4 fold reduction of clearance compared to Motavizumab on par with YTE. N3, with a clearance of 25.2 ml/day*kg was also on par with YTE for half-life extension. Interestingly, all pH binding engineered variants (except N3E-YTE) tested, with or without YTE, significantly reduced the serum clearance comparing to wild type Motavizumab, validating our approach to identify new variants with enhanced pharmacokinetics (FIG. 6B). Variants with improved PK parameters had pH 6.0 affinities varying from ~4 to 40 fold tighter compared to Motavizumab. Intriguingly, a pH 7.4 affinity of 25 nM yielded extremely poor clearance rates (N3E-YTE), whereas variants with pH 7.4 binding at ~1 μM affinity still exhibited enhanced half-life.

The FcγR and C1q binding of the motavizumab variants were also assessed. Interestingly, most variants, with the exception of N3 had reduced binding to certain FcγRs compared to motavizumab. These changes in binding ranged from minor (<2 fold decrease) to totally oblated binding to several receptors (as in the case of Y12-YTE). Interestingly, even the YTE mutation alone caused deceased binding in FcγRIII, FcγRIIa, and FcγRIIb suggesting that some effector functions may be diminished in the YTE background, but not in the N3 background.

Pharmacokinetics of N3 & Y31-YTE in Cynomolgus Monkeys

A novel Fc variant exhibiting low clearance in hFcRn mice, Y31-YTE was then compared to YTE and wild-type Motavizumab in cynomolgus monkeys. Four animals in each group received a single bolus injection of Motavizumab or Motavizumab-Fc variants; serum samples were taken over the next 85 days. In agreement with a previous study (Dall'Acqua et al. (2006) J. Biol. Chem. 281, 23514-23524), YTE-Motavizumab had improved pharmacokinetic properties versus wild-type Motavizumab. Y31-YTE also had improved pharmacokinetic properties versus motavizumab (Table 3). Three animals in the Y31-YTE group had abrupt drop offs of Y31-YTE serum concentrations between 500 and 1000 hour time periods, likely indicating anti-drug antibodies were clearing Y31-YTE motavizumab. Similar drop offs in the wild type and YTE group were not seen during this period.

TABLE 3

Cynomolgus pharmacokinetic data

| | T½ day | Cmax ug/mL | Cmax/Dose ug/mL * mg | AUClast ug * day/mL | AUCinf ug * day/mL | CL mL/day | CL mL/day * kg |
|---|---|---|---|---|---|---|---|
| Motavizumab | 5.8 ± 1.4 | 334 ± 20 | 9.2 ± 1.0 | 1360 ± 400 | 1420 ± 440 | 28.2 ± 8.4 | 8.5 ± 3.4 |
| YTE Motavizumab | 11.6 ± 6.5 | 344 ± 67 | 8.7 ± 1.4 | 3630 ± 370 | 3720 ± 380 | 10.7 ± 1.7 | 3.0 ± 0.3 |
| N3 Motavizumab | 14.3 ± 8.4 | 330 ± 59 | 9.0 ± 1.1 | 2990 ± 1170 | 3210 ± 1330 | 13.5 ± 5.2 | 3.9 ± 1.5 |
| Y31-YTE Motavizumab | 10.6 ± 5.0 | 279 ± 28 | 8.5 ± 0.5 | 2240 ± 450 | 2510 ± 630 | 13.9 ± 3.7 | 4.6 ± 1.2 |

Immunogenicity Assessment of N3

To evaluate whether the N3 mutation introduced immunogenic T-cell epitopes, N3-motavizumab and motavizumab were compared in ex vivo t-cell proliferation experiments. PBMCs from over 200 donors representing a wide breadth of HLA haplotypes were used in these experiments. PBMCs were incubated with either motavizumab, N3-motavizumab, buffer alone or the immunogenic KLH protein. T-cell proliferation was measured and results are quantified as a stimulation index (SI) comparing the T-cell proliferation of the donor PBMCs to the buffer alone control (SI=1). KLH protein had a significant increase in SI, whereas both motavizumab and N3-motavizumab did not (FIG. 7A, 7B). These data suggest that the N3 mutation has low immunogenicity when measured in this manner.

Opsonophagocytic Killing of N3 Variants Compared to YTE Variants

Figure 8:
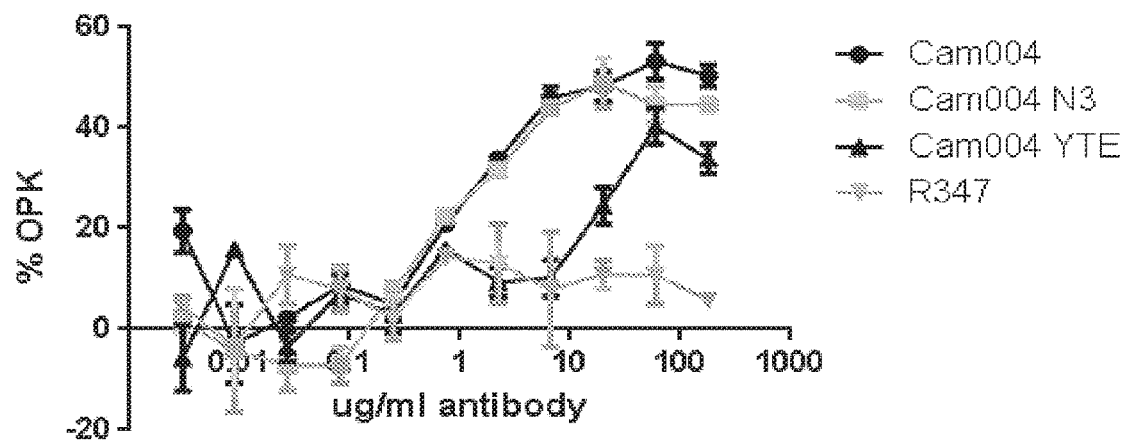
FIG. 8 depicts opsonophagocytic killing of *Pseudomonas aeruginosa*. (strain PA01:lux containing the luciferase gene) by patient derived polymorphonuclear cells. Cam004 wt (black circles) effectively facilitated OPK, whereas Cam004 YTE had reduced OPK (black triangles). Cam440 N3 (grey squares) has OPK similar to the parental Cam004. A non-specific antibody is also shown as a negative control (R347; grey triangles).

Fcγ receptor binding data with N3 and YTE suggested that N3 retains parental Fcγ receptor binding whereas YTE has reduced FcγR binding (Table 2). We assess whether the different FcγR binding affinity of these variants could lead to different effector functions in vitro, we generated both YTE and N3 variants of the anti-pseudomonas anti-psl antibody Cam004 (DiGiandomenico (2012) J. Exp. Med. 209 (7): 1273-87). These constructs were tested in an opsonophagocytic killing assay using patient derived polymorphonuclear cells as effectors, and a luciferase expressing *Pesudomonas* strain (PAO1:lux) as the target antibody. Results show that N3 displayed OPK similar to that of the parental antibody Cam004, whereas YTE had decreased OPK (FIG. 8).

Stability of N3 Variants.

Figure 9:
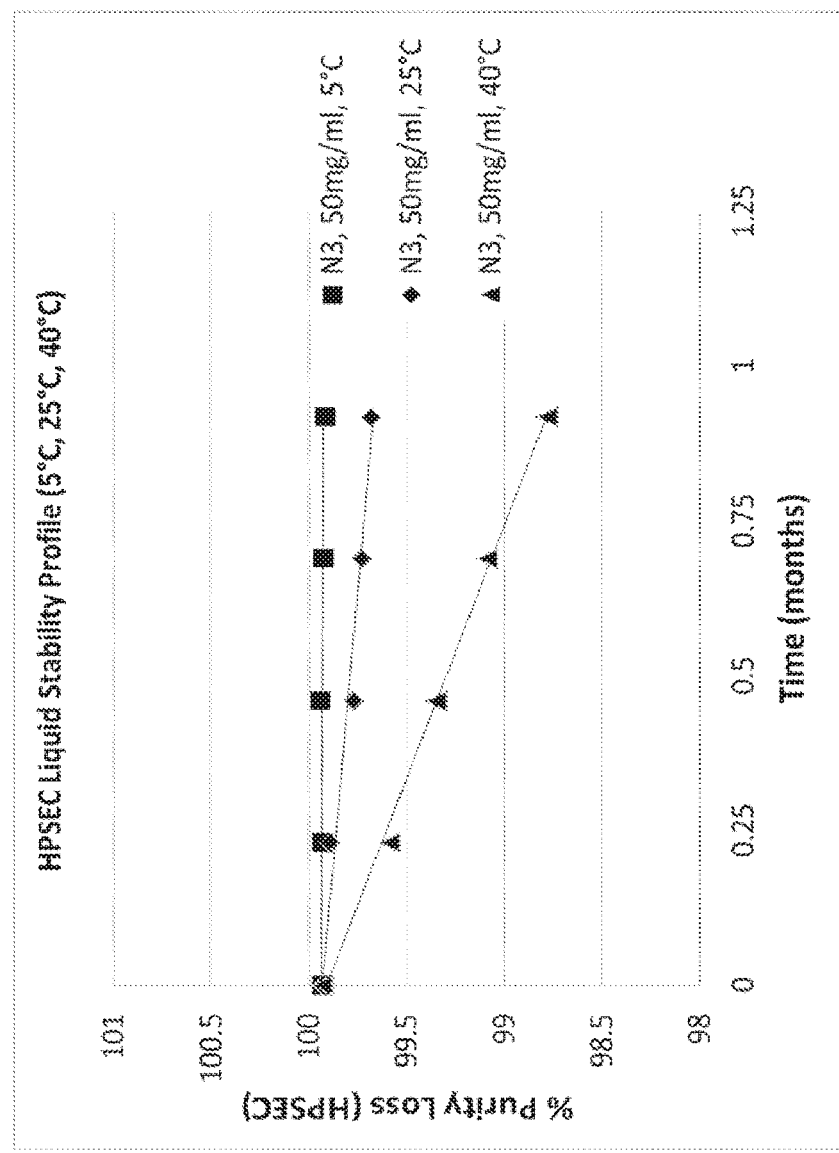
FIG. 9 depicts the results of a month long stability stress test with an N3 variant antibody (N3 Motavizumab) at 50 mg/ml incubated at 4° C. (black squares), 25° C. (black diamonds), or 40° C. (black triangles) for one month.

Accelerated stability studies were performed with N3 Motavizumab in a liquid formulation (50 mg/ml in PBS pH 7.2 buffer). The antibody formulation was incubated at 4° C., 25° C., or 40° C. for one month. At weekly time points, aliquots were taken and analyzed by HPSEC to determine monomeric content as well as any fragmentation or aggregation. The data in FIG. 9 depicts monomer loss versus time and shows the N3 variant to be quite stable, with a 1.2% loss per month at 40° C. and only a 0.3% per month at 25° C. These data indicate that the N3 mutations do not impact the stability of the Fc region.

Discussion

The Fc region of IgG is fertile ground for mutations that can alter the potency and efficacy of therapeutic antibodies. A myriad of different studies have identified Fc variants with altered in vivo half-life or effector functions (Strohl (2009) Curr. Opin. Biotechnol. 20, 685-691; Presta (2008) Current Opinion in Immunology 20, 460-470; Lazar et al. (2006) Proc. Natl. Acad. Sci. U.S.A. 103, 4005-4010). The possible benefits of antibodies with extended pharmacokinetic parameters include better tailoring to fit specific therapeutic windows which could result in reduced dosing frequency while maintaining or even improving efficacy (Zalevsky et al. (2010) Nat. Biotechnol. 28, 157-159). At the opposite end of the spectrum are Fc variants with reduced half-lives. These antibodies may be useful for imaging purposes such as positron emission tomography (PET) imaging where fast clearance rates are desirable for imaging clarity and to reduce toxicity (Kenanova et al. (2010) Engineering of the Fc Region for Improved PK (FcRn Interaction). pp 411-430; Olafsen et al. (2006) Nature Protocols 1, 2048-2060). Abdegs are a third class of Fc variants with altered FcRn binding (Vaccaro et al. (2005) Nat. Biotechnol. 23, 1283-1288). The ability of Abdegs to lower endogenous IgG levels could possibly be used to ameliorate certain autoimmune diseases characterized by destructive autoantibodies (Killock (2011) Nat Rev Rheumatol 7, 496-496; Patel et al. (2011) J. Immunol. 187, 1015-1022; Challa et al. (2013) mAbs 5, 655-659 Epub). To better understand the parameters that separate the disparate in vivo pharmacokinetic outcomes that come from engineering the Fc-FcRn interaction, we used Fc phage display to select for high affinity binders.

Our first attempt to select for high affinity FcRn binding variants in the YTE background yielded N3E-YTE which bound >50 fold tighter to FcRn than the already affinity enhanced YTE variant at pH 6. The glutamic acid insertion mutation after position 437 did contribute to the affinity increase as evidenced by a 6 fold decrease in binding upon its removal (Table 1). In addition to the insertion and hydrophobic residues at positions 434 and 436, N3E-YTE contains two cysteines at positions 432 and 437. The positioning of the cysteines at the base of the His 435 loop, the proximity and directions of their side chains, and the stabilizing effect of these mutations lead us to believe they form a disulfide bond with each other. We have subsequently confirmed this by peptide mapping. Differential scanning calorimetry confirms the stabilizing effect of L432C and T437C on CH3, at the expense of a slight destabilizing effect of CH2 (FIG. 3). These data indicate that both the cysteines are likely important for stability of the loop and intervening sequences confer most of the increased affinity and loss of pH sensitivity. The poor pH dependency seen with N3E-YTE was not unexpected. N434W alone has been reported to have increased FcRn binding at both pH 6.0 and 7.4 (Yeung et al. (2009) J. Immunol. 182, 7663-7671). Additionally, the MST-HN mutant (M252Y, S254T, T256E, H433K, N434F), combining the YTE mutation with two additional H435 loop mutants, also exhibits reduced pH dependency resulting in an abdeg (Dall'Acqua et al. (2002) J. Immunol. 169, 5171-5180; Vaccaro et al. (2005) Nat. Biotechnol. 23, 1283-1288.

This initial data spurred the creation of 2 additional libraries, CXXXXCE (SEQ ID NO:10) and ZXXHXZ (SEQ ID NO:14). These libraries were then panned with a pH 7.4 depletion step to eliminate pH insensitive binders, and isolated clones were evaluated by phage ELISA (FIGS. 5A and 5B). The ZXXHXZ (SEQ ID NO:14) library yielded the more high affinity pH dependent binders via phage ELISA, suggesting that easing the restraints caused by the 432 and 437 cysteines in the CXXXXCE (SEQ ID NO:10) library may have been beneficial to reintroducing pH dependency. Of note, the CXXXXCE (SEQ ID NO:10) library also contained the glutamic acid insertion after residue 437 (which ZXXHXZ (SEQ ID NO:14) lacked) and this could also account for some of the disparate binding profiles of variants identified from these libraries. Interestingly, the mutations identified from ZXXHXZ (SEQ ID NO:14) library that maintained higher affinity than YTE alone with pH sensitive binding consisted of charged residues at either positions 433, 436 or both, with a hydrophobic residue at 434 (Table 1). The increase in positive charges may contribute to pH dependency of these variants.

The variant N3 was shown to have similar pharmacokinetics to YTE in HuFcRn mice and cynomolgus, and additionally, unlike YTE, to retain Fcγ and C1q binding similar to wild-type IgG. Moreover, again unlike YTE, N3 was found to have OPK activity equivalent to parental IgG in Pseudomonas PA01 lux system (FIG. 8). In addition, the N3 variant does not impact the stability of the Fc region upon storage. N3 is accordingly expected to have utility, for example, as a modified IgG for use in antibody-mediated clearance applications that target an infectious agent, where a longer half-life and robust effector function is desirable.

Figure 6A:
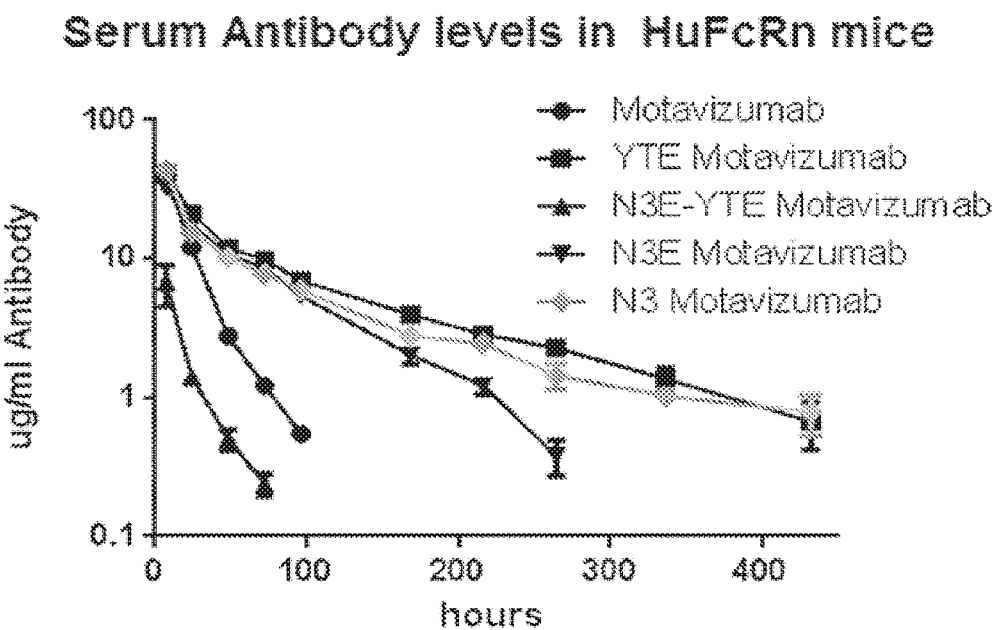
FIGS. 6A and B show pharmacokinetic (PK) analysis of Motavizumab variants in hFcRn transgenic mice.
Figure 6B:
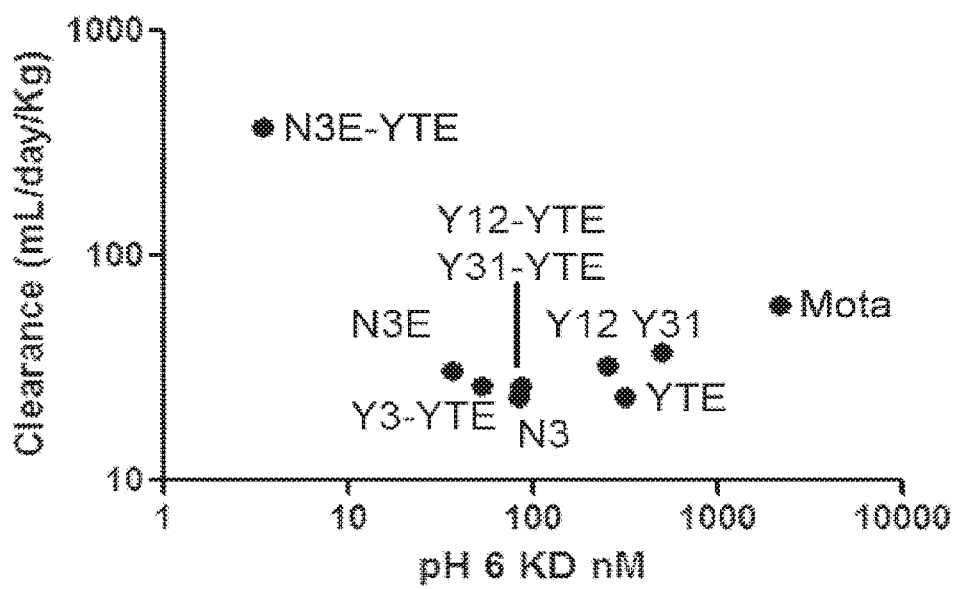
FIG. 6B shows clearance rates of all antibody variants tested in Table 2 are plotted against their pH 6.0 hFcRn binding affinity.

Our data suggest that there is likely a threshold level for FcRn mediated half-life extension (FIG. 6B) and that delving beyond this threshold will not yield further PK improvements. Indeed, increasing FcRn affinity too much beyond this threshold will result in molecules like N3E-YTE or MST-HN that exhibit shorter than wild-type half-lives (Montoyo et al. (2009) Proc. Natl. Acad. Sci. U.S.A. 106, 2788-2793) and may perturb normal IgG recycling (Vaccaro et al. (2005) Nat. Biotechnol. 23, 1283-1288). Unexpectedly, we found that variants with pH 7.4 binding as low as 1 uM still maintained enhanced in vivo half-life on par with that of YTE alone (Table 2). N3E-YTE with a pH 7.4 $K_D$ of 24 nM exhibited extremely fast clearance. We propose that below this ~1 uM threshold there seems to be a critical point for determining whether variants with enhanced binding at pH 6.0 become either PK enhanced or Abdeg-like exhibiting faster than wild type clearance.

The variants with the longest half-life in HuFcRn mice, N3 and Y31-YTE, had almost 3 fold better clearance than wild type Motavizumab and ~5 fivefold longer half-life. These variants rank among the top PK improved variants described (Presta (2008) Current Opinion in Immunology 20, 460-470). Approximately 3-5 fold enhancement in half-life or clearance rates compared to the parental antibody are the highest reported improvements achieved by altering FcRn binding (Dall'Acqua et al. (2006) J. Biol. Chem. 281, 23514-23524; Zalevsky et al. (2010) Nat. Biotechnol. 28, 157-159). Pharmacokinetic data in Cynomolgus monkeys also showed improvements for Y31-YTE and N3 vs. wild type Motavizumab as well. In light of our data and others it is difficult to envision there is room for significant improvement beyond 3-4 fold PK enhancement purely by further altering FcRn binding. We do envision that even longer In vivo half-lives for Fc containing molecules could be achieved by combining FcRn binding mutations with FcRn independent half-life extending technologies such as pI engineering (Dahiyat et al. (2012) U.S. Pat. Pub. 20120028304 published Feb. 2, 2012), PEGylation (Jevsevar et al. (2010) Biotechnol. J. 5, 113-128), PASylation (Schlapschy et al. (2013) Protein Eng. Des. Sel. 26, 489-501), pH dependent antigen binding (to reduce the effects of antigen sinks) (Igawa et al. (2010) Nat. Biotechnol. 28, 1203-1207; Igawa et al. (2011) Protein Eng. Des. Sel. 23, 385-392).

Example II

Antibody Format for Therapeutic Strategies Relying on Antibody Mediated Clearance with pH-Dependent Antigen Binding Antibodies have been engineered for pH-dependent binding of their antigen. The engineered antibody binds the antigen in circulation (pH 7.4) to mediate the clearance, but releases it in the sorting endosome (pH 6), thereby enabling recycling of the antibody via FcRn while the antigen left behind is degraded in the endosome.

Figure 10A:
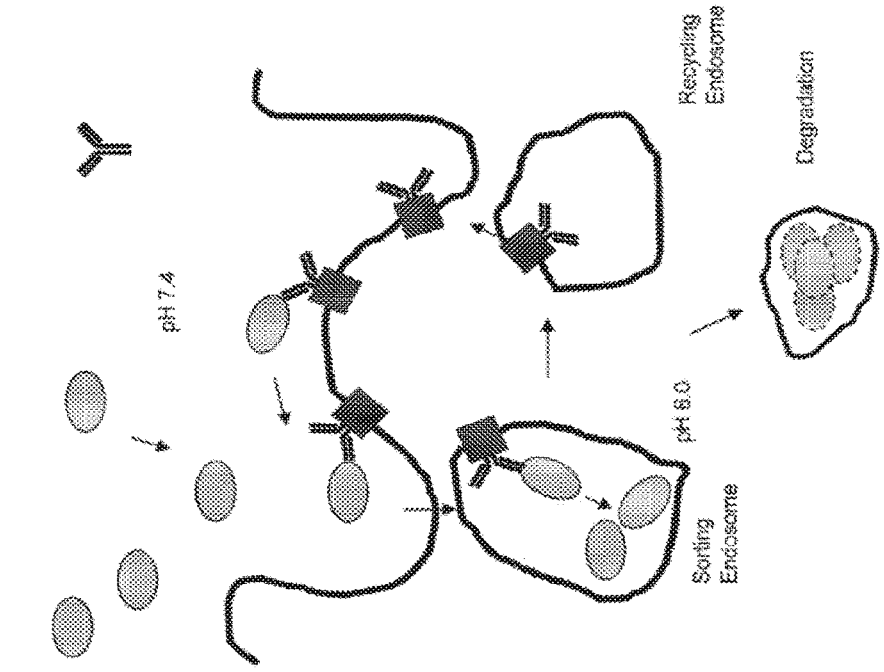
FIGS. 10A and B are schematic representations of antigen clearance with an antibody exhibiting pH-dependent antigen binding.
Figure 10B:
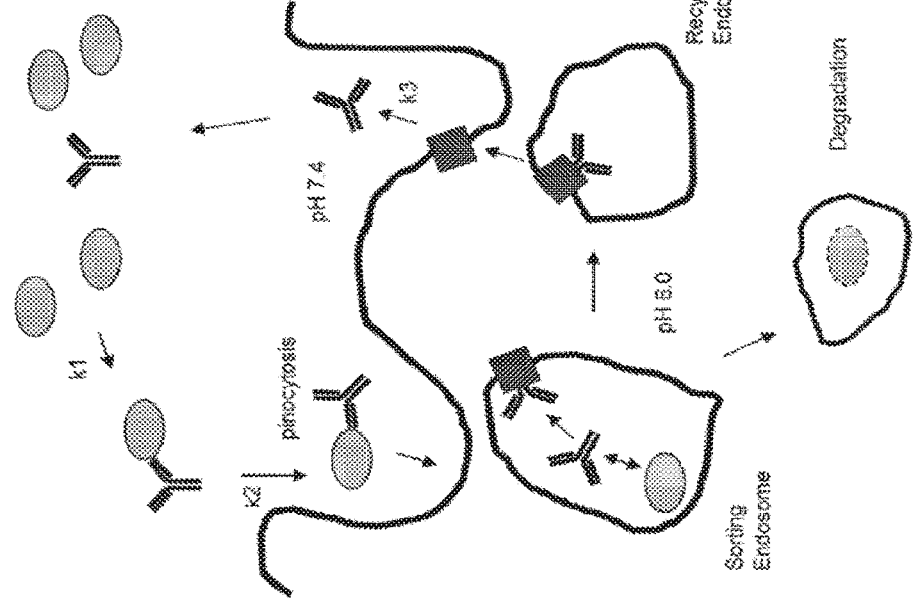
FIG. 10B shows possible endocytosis using an antibody exhibiting high affinity for FcRn at 7.4 as well as pH 6.0.

Antibody formats with high affinity for FcRn at both pH 7.4 and 6.0 are described herein. One example is N3E-YTE, described in Example I, which exhibits a shorter half-life than comparable wild-type antibodies. A possible explanation for the shorter half-life of N3E-YTE and others like it may be that these antibodies remain bound to FcRn at the cell surface, and consequently are not detected in serum samples. If they are cycled into endosomes in complex with FcRn, this format is expected to be much more efficient for antigen clearance (see FIG. 10).

A more efficient antibody mediated clearance is therefore envisioned. An antibody format with high affinity for FcRn at both physiological pH (pH 7.4) and low pH (pH 6) may be bound to FcRn in both the endosomal compartments and at the cell surface. As a result it would bind antigens at the cell surface and actively mediate the internalization into the endosomes, which would be much more efficient for antigen clearance. Furthermore, antibody driven endocytosis is a mechanism that may support sampling of serum content of the immune system (Kuo T T et al, J Clin Immunol (2010) 30:777-789). Increasing the efficiency should therefore be possible by increasing the FcRn affinity at physiological pH, as described herein.

The efficacy of such antibodies can be tested in vivo. A model system with clinical relevance is PCSK-9. An anti-PCSK-9 antibody with pH dependent binding is known (Chaparro-Riggers et al., 2012, JBC 287:11090-11097). The variable region of an anti-PCSK-9 antibody that is engineered for pH-dependent binding to its antigen can be engineered into any of the antibody base structures falling into quadrants I and III have altered FcRn binding. In some cases, those based structures falling into quadrant III may be preferred. Generation of such antibodies can be accomplished using the procedures described herein, enabling a side by side comparison with wild-type anti-PCSK-9. The rate of clearance of exogenous PCSK9 at various time points can be readily measured. Any other antibody with pH dependent binding can be used for similar studies. This system offers increased efficacy for all applications relying on antibody clearance where antibodies with pH-dependent antigen binding can be engineered.

The complete disclosures of all patents, patent applications including provisional patent applications, publications including patent publications and nonpatent publications, and electronically available material (including, for example, nucleotide sequence submissions in, e.g., Gen-Bank and RefSeq, and amino acid sequence submissions in, e.g., SwissProt, PIR, PRF, PDB, and translations from annotated coding regions in GenBank and RefSeq) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A modified human or humanized IgG1 comprising an Fc region wherein
   (i) positions 432 and 437 are each substituted with cysteine,
   (ii) position 433 is substituted with serine;
   (iii) position 434 is substituted with tryptophan or tyrosine;
   (iv) position 435 is histidine;
   (v) position 436 is substituted with leucine;
   numbered according to the EU numbering index of Kabat, relative to a human wild-type Fc region;
   and wherein the modified human or humanized IgG1 has an increased half-life compared to the half-life of an IgG1 having the human wild-type Fc region.

2. The modified human or humanized IgG1 of claim 1, wherein position 434 is substituted with tyrosine.

3. The modified human or humanized IgG1 of claim 1, wherein the binding affinity of the modified human or humanized IgG1 for FcRn at pH 6.0 is higher than the binding affinity of the IgG1 having the human wild-type Fc region for FcRn at pH 6.

4. The modified human or humanized IgG1 of claim 1, wherein the binding affinity of the modified human or humanized IgG1 for FcRn at pH 7.4 is higher than the binding affinity of the IgG1 having the human wild-type Fc region for FcRn at pH 7.4.

5. The modified human or humanized IgG1 of claim 1, wherein the modified human or humanized IgG1 exhibits increased pH dependence of binding affinity for FcRn compared to the IgG1 having the human wild-type Fc region.

6. The modified human or humanized IgG1 of claim 1, wherein the modified human or humanized IgG1 exhibits decreased pH dependence of binding affinity for FcRn compared to the IgG1 having the wild-type Fc region.

7. The modified human or humanized IgG1 of claim 1, selected from the group consisting of N3 defined by SEQ ID NO: 20 or N3E defined by SEQ ID NO: 16.

8. A polypeptide comprising an FcRn-binding portion of an Fc region of a human IgG1 molecule, wherein positions 432 and 437 of said FcRn-binding portion are each substituted with cysteine, position 433 is substituted with serine; position 434 is substituted with tryptophan or tyrosine; position 435 is histidine; and position 436 is substituted with leucine; numbered according to the EU numbering index of Kabat, relative to a wild-type human FcRn-binding portion.

9. The polypeptide of claim 8, wherein the FcRn binding portion of the Fc region comprises from about amino acid residues 231-446 of a human IgG1 molecule according to the EU numbering index of Kabat.

10. The polypeptide of claim 8, wherein the FcRn binding portion of the Fc region comprises from about amino acid residues 216-446 of a human IgG1 molecule according to the EU numbering index of Kabat.

11. A fusion protein comprising a non-IgG polypeptide covalently linked to at least an FcRn-binding portion of an Fc region of a human IgG1 molecule, wherein positions 432 and 437 of said FcRn-binding portion are each substituted with cysteine, position 433 is substituted with serine; position 434 is substituted with tryptophan or tyrosine; position 435 is histidine; and position 436 is substituted with leucine; numbered according to the EU numbering index of Kabat, relative to a wild-type human Fc region; and wherein said fusion protein has a longer in vivo half life than the non-IgG polypeptide.

12. The fusion protein of claim 11, wherein the FcRn binding portion of the Fc region comprises from about amino acid residues 231-446 of a human IgG1 molecule according to the EU numbering index of Kabat.

13. The fusion protein of claim 11, wherein the FcRn binding portion of the Fc region comprises from about amino acid residues 216-446 of a human IgG1 molecule according to the EU numbering index of Kabat.

14. The fusion protein of claim 11 wherein the non-IgG polypeptide is an immunomodulator, a receptor, a hormone or a drug.

15. A molecule comprising a non-protein agent conjugated to an FcRn-binding portion of an Fc region of a human IgG1 molecule, wherein positions 432 and 437 of said FcRn-binding portion are each substituted with cysteine, position 433 is substituted with serine; position 434 is substituted with tryptophan or tyrosine; position 435 is histidine; and position 436 is substituted with leucine; numbered according to the EU numbering index of Kabat, relative to a wild-type human Fc region; and wherein said molecule has a longer in vivo half life than the non-protein agent.

16. The molecule of claim 15, wherein the FcRn binding portion of the Fc region comprises from about amino acid residues 231-446 of a human IgG1 molecule according to the EU numbering index of Kabat.

17. The molecule of claim 15, wherein the FcRn binding portion of the Fc region comprises from about amino acid residues 216-446 of a human IgG1 molecule according to the EU numbering index of Kabat.

18. A pharmaceutical composition comprising the modified human or humanized IgG1 according to claim 1, and a pharmaceutically acceptable carrier.

19. A kit comprising the modified human or humanized IgG1, according to claim 1.

20. The fusion protein of claim 11, wherein position 434 is substituted with tyrosine.

21. The molecule of claim 15, wherein position 434 is substituted with tyrosine.

22. The modified human or humanized IgG1 of claim 1, wherein position 434 is substituted with tryptophan.

23. The polypeptide of claim 8, wherein position 434 is substituted with tyrosine.

24. The polypeptide of claim 8, wherein position 434 is substituted with tryptophan.

25. The fusion protein of claim 11, wherein position 434 is substituted with tryptophan.

26. The molecule of claim 15, wherein position 434 is substituted with tryptophan.

\* \* \* \* \*